(12) United States Patent
Harris et al.

US009079900B2

(10) Patent No.: US 9,079,900 B2
(45) Date of Patent: Jul. 14, 2015

(54) METHODS OF SYNTHESIS AND PURIFICATION OF HETEROARYL COMPOUNDS

(71) Applicant: SIGNAL PHARMACEUTICALS, LLC, San Diego, CA (US)

(72) Inventors: Roy L. Harris, San Diego, CA (US); John Sapienza, Chula Vista, CA (US); Graziella Shevlin, Lima (PE); Patrick Papa, Carlsbad, CA (US); Branden Gingsee Lee, San Diego, CA (US); Garrick Packard, Minneapolis, MN (US); Jingjing Zhao, San Diego, CA (US); Patrick Anthony Jokiel, Yarmouth, ME (US); Deborah Mortensen, San Diego, CA (US); Jennifer Riggs, Cardiff, CA (US); Juan Antonio Gamboa, New York, NY (US); Marie Georges Beauchamps, Madison, NJ (US); Matthew Michael Kreilein, Watchung, NJ (US); Mohit Atul Kothare, Bridgewater, NJ (US); Sophie Perrin-Ninkovic, La Jolla, CA (US); Philip Pye, Kasterlee (BE); William Wei-Hwa Leong, Westfield, NJ (US); Jan Elsner, San Diego, CA (US); Anusuya Choudhury, Churchville, PA (US)

(73) Assignee: Signal Pharmaceuticals, LLC, San Diego, CA (US)

(*) Notice: Subject to any disclaimer, the term of this patent is extended or adjusted under 35 U.S.C. 154(b) by 0 days.

(21) Appl. No.: 14/174,896

(22) Filed: Feb. 7, 2014

(65) Prior Publication Data
US 2014/0155593 A1 Jun. 5, 2014

Related U.S. Application Data

(60) Continuation of application No. 13/873,662, filed on Apr. 30, 2013, now Pat. No. 8,686,135, which is a division of application No. 12/910,920, filed on Oct. 25, 2010, now Pat. No. 8,569,494.

(60) Provisional application No. 61/328,480, filed on Apr. 27, 2010, provisional application No. 61/254,917, filed on Oct. 26, 2009.

(51) Int. Cl.
*A61K 31/497* (2006.01)
*C07D 241/00* (2006.01)
*C07D 471/04* (2006.01)
*C07D 487/04* (2006.01)
*C07D 498/14* (2006.01)
*C07D 519/00* (2006.01)

(52) U.S. Cl.
CPC .......... *C07D 471/04* (2013.01); *C07D 487/04* (2013.01); *C07D 498/14* (2013.01); *C07D 519/00* (2013.01)

(58) Field of Classification Search
USPC ........................................ 514/252.1; 544/336
See application file for complete search history.

(56) References Cited

U.S. PATENT DOCUMENTS

| | | | |
|---|---|---|---|
| 3,507,866 | A | 4/1970 | Jones et al. |
| 3,567,725 | A | 3/1971 | Grabowski et al. |
| 4,294,836 | A | 10/1981 | Lesher et al. |
| 4,294,837 | A | 10/1981 | Lesher et al. |
| 4,309,537 | A | 1/1982 | Lesher et al. |

(Continued)

FOREIGN PATENT DOCUMENTS

| | | |
|---|---|---|
| CA | 2 458 699 A1 | 3/2003 |
| DE | 262 026 | 11/1988 |

(Continued)

OTHER PUBLICATIONS

Barlin 1982, "Purine analogs as amplfiers of phleomycin. VII. Some 1H-inidazo[4,5-b]pyrazines and related compound," Australian Journal of Chemistry, vol. 35:2299-2306.

(Continued)

*Primary Examiner* — James O Wilson
*Assistant Examiner* — Oluwafemi Masha
(74) *Attorney, Agent, or Firm* — Jones Day

(57) ABSTRACT

Provided herein are methods to prepare Heteroaryl Compounds having the following structure:

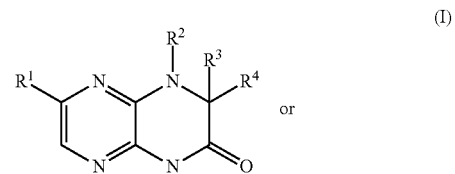

(I)

or

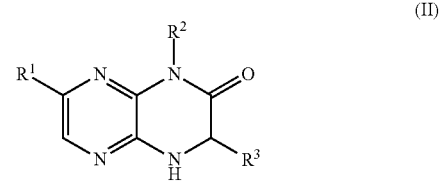

(II)

wherein $R^1$-$R^4$ are as defined herein. The Heteroaryl compounds are useful for treating or preventing cancer, inflammatory conditions, immunological conditions, neurodegenerative diseases, diabetes, obesity, neurological disorders, age-related diseases, or cardiovascular conditions.

27 Claims, No Drawings

(56) References Cited

U.S. PATENT DOCUMENTS

| | | | |
|---|---|---|---|
| 4,317,909 | A | 3/1982 | Lesher et al. |
| 4,898,872 | A | 2/1990 | Campbell et al. |
| 4,963,561 | A | 10/1990 | Lesher et al. |
| 5,424,311 | A | 6/1995 | Billhardt-Troughton |
| 5,869,659 | A | 2/1999 | Stolle et al. |
| 6,031,105 | A | 2/2000 | Wright |
| 6,093,728 | A | 7/2000 | McMahon et al. |
| 6,372,740 | B1 | 4/2002 | Murata et al. |
| 6,566,367 | B2 | 5/2003 | Bakthavatchalam et al. |
| 6,855,723 | B2 | 2/2005 | McMahon et al. |
| 2003/0036652 | A1 | 2/2003 | Bakthavatchalam et al. |
| 2003/0162968 | A1 | 8/2003 | Ciriillo et al. |
| 2004/0023921 | A1 | 2/2004 | Hong et al. |
| 2004/0063658 | A1 | 4/2004 | Roberts et al. |
| 2004/0097485 | A1 | 5/2004 | Burkitt et al. |
| 2005/0009737 | A1 | 1/2005 | Clark |
| 2006/0004014 | A1 | 1/2006 | Hoffmann et al. |
| 2006/0106022 | A1 | 5/2006 | Liu et al. |
| 2006/0135511 | A1 | 6/2006 | Burgey |
| 2006/0142269 | A1 | 6/2006 | Dykes |
| 2008/0214580 | A1 | 9/2008 | Neagu et al. |
| 2009/0023724 | A1 | 1/2009 | Mortensen et al. |
| 2009/0042890 | A1 | 2/2009 | Mortensen et al. |
| 2009/0069289 | A1 | 3/2009 | Neagu et al. |
| 2009/0163545 | A1 | 6/2009 | Goldfard |
| 2009/0281075 | A1 | 11/2009 | Roughton et al. |
| 2010/0144738 | A1 | 6/2010 | Bornmann et al. |
| 2010/0216781 | A1 | 8/2010 | Perrin-Ninkovic et al. |
| 2010/0249122 | A1 | 9/2010 | Kalman |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002100363 | 4/2002 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/48152 | 6/2002 |
| WO | WO 02/076954 | 10/2002 |
| WO | WO 03/032989 | 4/2003 |
| WO | WO 03/093290 | 11/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/003147 | 1/2005 |
| WO | WO 2006/050076 | 5/2005 |
| WO | WO 2005/120511 | 12/2005 |
| WO | WO 2006/001266 | 1/2006 |
| WO | WO 2006/030031 | 3/2006 |
| WO | WO 2006/036883 | 4/2006 |
| WO | WO 2006/045828 | 5/2006 |
| WO | WO 2006/065703 | 6/2006 |
| WO | WO 2006/087530 A1 | 8/2006 |
| WO | WO 2006/091737 | 8/2006 |
| WO | WO 2006/108103 | 10/2006 |
| WO | WO 2008/016669 | 2/2008 |
| WO | WO 2008/051493 | 5/2008 |
| WO | WO 2008/051494 | 5/2008 |
| WO | WO 2010/062571 | 6/2010 |
| WO | WO 2010/068483 | 6/2010 |

OTHER PUBLICATIONS

Beresnev et al., 2000, "Interaction of 5-methoxy-1,2,4-traizines with uras as a new route to 6-azapurines," Medeleev Commu., vol. 2:58-59.

Bergmann et al., 1963, "2-Phenylpurines, their chemical and enzumological reactivity," J. Chem Org., pp. 3729-3735.

Booth et al., 1992, "Synthesis of 9-Hydroxyalkyl-substituted purines from the corresponding 4-(C-Cyanoformimidoyl)imidazole-5-amines," J, Chem Society, Perkin Transactions 1: Organic and Bio-Organic Chemstry, vol. 2119-26.

Booth et al., 1995, "Synthesis of [1 α, 2β,3α-2,3-bis(benzyloxymethyl)cyclobutl]imidazol-5-amines: important precursors to cyclobut-A derivatives," J. Chem Society, Perkin Tranactions 1: Organic and Bio-Organic Chemistry, vol. 6, pp. 669-675.

Booth et al., 2001, "The Reactions of Diaminomaleonitrile with Isocyanates and Either Aldehydes or Ketones Revisited," J. Org Chem, vol. 66:8436-8441.

Booth, et al., 1994, "Synthesis of 4- and 5-Disubstituted 1-Benzylimidazoles, Important Precursors of Purine Analogs," J. of Heterocyclic of Chemistry, vol. 31(2):345-50.

Chupakhin et al., 2001, "A simple one pot synthesis of condensed 1,2,4-triazines by using the tandem $A_N$-$S_N$ipso and $S_N^H$—$S_N$ispo reactions," J. of Heterocyclic Chemistry, vol. 38(4):901-907.

Cohen, P. 2001, "The role of protein phosphorylation in human health and disease," Eur. J. Biochem, vol. 268:5001-5010.

Cohen, P. 2002, "Protein kinases—the major drug targets or the twenty-first century?" Nature Reviews/Drug Discovery, vol. 1:309-315.

Coish, et al., 2006, "Small molecule inhibitors of IKK kinase activity," Expert Opin. Ther. Patents, vol. 16(1):1-12.

Crofts et al., 1997 "Metabolism of 2-amino-1-methyl-6-phenylimidazo[4,5-b] pyridine (PhIP) by human cytochrome P4501B1," Carcinogenesis, vol. 18(9):1793-1798.

Dang et al., 1999, "Efficient synthesis of purines and purine nucelosides via an inverse electron demand diels—alder reaction," J. Am Chem Soc., vol. 121(24):5833-5834.

Database CAPLUS Online Chemical Abstracts Service, Columbus, Ohio, Database Accession No. 1951:49974 (XP-002472261) (1951).

Database CAPLUS Online Chemical Abstracts Service, Columbus, Ohio, Database Accession No. 1978:433195 (XP-002472262) (1978).

Database CAPLUS Online Chemical Abstracts Service, Columbus, Ohio, Database Accession No. 1966:26849 (XP-002472263) (1965).

Dornow et al., 1957, "Synthese von2-Oxy-imidazolo-(5',4':2,3)-pyridinen)," Arch Pharm. vol. 290, pp. 20-31 (w/English language abstract).

Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47, pp. 5783-5790.

Fabbro et al., 2002, "Protein kinasesas targets for anticancer agents: from inhibitors to useful drugs," Pharm & Therapeutics, vol. 93:79-98.

Farhadi et al., 2006, "The role of protein kinase C isoforms in modulating injury and repair of the intestinal barrier," J. Pharm Exp. Ther., vol. 316(1):1-7.

Frandsen et al., 1992, "Reaction of the N2-acetoxy derivative of 2-amino-l-methyl-6-phenylimidazo[4,5,b]pyridine . . . ," Carcinogenesis, vol. 13(4):629-635.

Georgakis and Younes, 2006, "From rapi nui to rapamycin: targeting PI3K/Akt/mTOR for cancer therapy," Expert Rev. Anticancer Ther., vol. 6(1):131-140.

Hamad, 2001, "A new synthesis of 4-cyano-1,3-dihydro-2-oxo-2H-imidazole-5-($N^1$-tosyl)carboxamide: Reactive precursor for thiopurine analogues," J of Heterocyclic Chemistry, vol. 38(4):939-944.

Irie et al., 2005, "Toward the development of new medicinal leads with selectivity for protein kinase C isozymes," The Chemical Record, vol. 5:185-195.

Itoh et al., 2004, "A novel practical synthesis of C-2-arylpurines," Advanced Synthesis & Catalysis, vol. 346:1859-1867.

Jones et al., 1973, "6-Substituted-5-chloro-1,3-dihydro-2H-imidazo(4,5-b)pyrazin-2-ones with hypotensive activity," J. Med. Chem., vol. 16(5):537-542.

Kazaoka et al., 2003, "Synthesis of 6-substituted 9-benzyl-8-hydroxypurines with potential interferon-indcuing activity," Chemical & Pharmaceutical Bulletin, vol. 51(5):608-611.

Killday et al., 2001, "Microxine, a new cdc2 kinase inhibitor from the Australian marine sponge Microxina species," J. of Natural Products, vol. 64(4):525-526.

(56) References Cited

OTHER PUBLICATIONS

Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.

Nagashima et al., 2004, "Solution-Phase parallel synthesis of an N-Alkylated dihydropteridinone library from fluorous amino acids," J of Comb. Chemistry, vol. 6(6):942-949.

Park et al., 2000, "A novel mechanism of TRAF signaling revealed by structural and functional analyses of the TRADD-TRAF2 interaction," Cell, vol. 101:777-787.

Patani et al., 1998, "Bioisosterim: A rational approach in drug design," Chemical Reviews, vol. 96:3147-3176.

Registry File Document for RN 863501-03-5, 863502-39-0 and others (Sep. 20, 2005).

Seela et al., 2004, "Product Class 17: Purines," Science of Synthesis, vol. 16, pp. 945-1108.

Singh et al., 1994, "Novel cAMP PDE III Inhibitors: Imidazo[4,5-b]pyridin-2(3H)-ones and Thiazolo[4,5-b]pyridin-2(3h)-ones and Their Analogs," J. Med. Chem, vol. 37(2):248-54.

Sridhar et al., 2000, "Proteinkinases as therapeutic targets," Pharm Research, vol. 17(11):1345-1353.

Westover et al., 1981, "Synthesis and antiviral activity of certain 9-β-D-Riofuranoaylpurine-6-carboxamides," J.Med. Chem., vol. 24(8):941-46.

Yoneda et al., 1976, "A transformationof 7-azapteridines into 6-azapurines (Imidazo[4,5-e]- as-triazines)," Heterocycles, vol. 4(9):1503-1508.

Yoneda et al., 1978, "Synthesis of imadazo[4,5-e]-as-triazine (6-Azapurine) Deriviatives," Chem & Pharm Bulletin, vol. 26(10):3154-60.

Yoneda et al., 1978, "Synthesis of imadazo[4,5-e]-as-triazine (6-Azapurine) Deriviatives," Chem & Pharm Bulletin, vol. 26(10):3154-3160.

Zaki et al., 2007, "The synthesis of imidazol[4,5-*d*]pyridines from a substituted imidazole and acyl or sulfonyl acetonitrile," Tetrahedron, vol. 63(18):3745-3753.

Wallace 2008, "Palladium-catalyzed synthesis of quinoxaline derivatives," Tetrahedron, vol. 64:9675-9684.

http://www.sigmaaldrich.com/catalog/product/aldrich/697230?lang=en&region=US, last accessed Nov. 1, 2012.

http://www.sigmaaldrich.com/catalog/product/ALDRICH/701602?lang=en&region=US#, last accessed Nov. 1, 2012.

http://www.sigmaaldrich.com/catalog/product/ALDRICH/678740?lang=en&region=US, last accessed Nov. 1, 2012.

http://www.sigmaaldrich.com/chemistry/chemical-synthesis/technology-spotlights/catalysisapplicationguide.html, last accessed Nov. 1, 2012.

METHODS OF SYNTHESIS AND PURIFICATION OF HETEROARYL COMPOUNDS

This application is a continuation of U.S. patent application Ser. No. 13/873,662, filed Apr. 30, 2013, currently allowed, which is a divisional of U.S. patent application Ser. No. 12/910,920, filed Oct. 25, 2010, now U.S. Pat. No. 8,569,494, which claims the benefit of U.S. Provisional Application No. 61/254,917, filed Oct. 26, 2009 and U.S. Provisional Application No. 61/328,480, filed Apr. 27, 2010, the entire contents of each of which are incorporated herein by reference.

1. FIELD

Provided herein are processes generally pertaining to the field of chemical synthesis and purification, and more specifically to methods of synthesis and/or purification of certain heteroaryl compounds.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. mTORC1 is sensitive to rapamycin analogs (such as temsirolimus or everolimus) and mTORC2 is largely rapamycin-insensitive. Several mTOR inhibitors have been or are being evaluated in clinical trials for the treatment of cancer. Temsirolimus was approved for use in renal cell carcinoma in 2007 and everolimus was approved in 2009 for renal cell carcinoma patients that have progressed on vascular endothelial growth factor receptor inhibitors. In addition, sirolimus was approved in 1999 for the prophylaxis of renal transplant rejection. The interesting but limited clinical success of these mTORC1 compounds demonstrates the usefulness of mTOR inhibitors in the treatment of cancer and transplant rejection, and the increased potential for compounds with both mTORC1 and mTORC2 inhibitory activity.

Citation or identification of any reference in Section 2 of this application is not to be construed as an admission that the reference is prior art to the present application.

3. SUMMARY

Provided herein are methods of preparing compounds having the following formula (I):

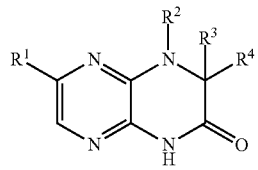

and pharmaceutically acceptable salts, tautomers, and stereoisomers thereof, wherein $R^1$-$R^4$ are as defined herein.

Further provided herein are methods of preparing compounds having the following formula (II):

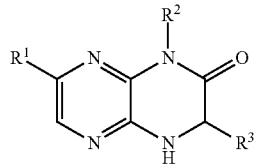

and pharmaceutically acceptable salts, tautomers, and stereoisomers thereof, wherein $R^1$, $R^2$ and $R^3$ are as defined herein.

Further provided herein are chemical intermediates useful in the methods provided herein.

Compounds of formula (I) and (II), or pharmaceutically acceptable salts, tautomers, and stereoisomers thereof (each being referred to herein as "Heteroaryl Compounds"), are useful for treating or preventing cancer, inflammatory conditions, immunological conditions, neurodegenerative diseases, diabetes, obesity, neurological disorders, age-related diseases, and cardiovascular conditions, and conditions treatable or preventable by inhibition of a kinase pathway, for example, the mTOR/PI3K/Akt pathway.

The present embodiments can be understood more fully by reference to the detailed description and examples, which are intended to exemplify non-limiting embodiments.

4. DETAILED DESCRIPTION

4.1. Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturated alkyl groups include, but are not limited to, vinyl, allyl, —CH═CH(CH₃), —CH═C(CH₃)₂, —C(CH₃)═CH₂, —C(CH₃)═CH(CH₃), —C(CH₂CH₃)═CH₂, —C≡CH, —C≡C(CH₃), —C≡C(CH₂CH₃), —CH₂C≡CH, —CH₂C≡C(CH₃) and —CH₂C≡C(CH₂CH₃), among others. When the alkyl groups described herein are said to be "substituted," they may be substituted with any substituent or substituents as those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, or O(alkyl) aminocarbonyl. An alkyl group can be substituted or unsubstituted.

A "cycloalkyl" group is a saturated, partially saturated, or unsaturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocyclylalkyl groups include but are not limited to 4-ethyl-morpholinyl, 4-propylmorpholinyl, furan-2-yl methyl, furan- 3-yl methyl, pyrdine-3-yl methyl, (tetrahydro-2H-pyran-4-yl)methyl, (tetrahydro-2H-pyran-4-yl)ethyl, tetrahydrofuran-2-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: —$NH_2$.

An "alkylamino" group is a radical of the formula: —NH-alkyl or —N(alkyl)$_2$, wherein each alkyl is independently as defined above.

A "carboxy" group is a radical of the formula: —C(O)OH.

An "aminocarbonyl" group is a radical of the formula: —C(O)N($R^{\#}$)$_2$, —C(O)NH($R^{\#}$) or —C(O)$NH_2$, wherein each $R^{\#}$ is independently a substituted or unsubstituted alkyl, cycloalkyl, aryl, aralkyl, heterocyclyl or heterocyclyl group as defined herein.

An "acylamino" group is a radical of the formula: —NHC(O)($R^{\#}$) or —N(alkyl)C(O)($R^{\#}$), wherein each alkyl and $R^{\#}$ are independently as defined above.

An "alkylsulfonylamino" group is a radical of the formula: —$NHSO_2$($R^{\#}$) or —N(alkyl)$SO_2$($R^{\#}$), wherein each alkyl and $R^{\#}$ are defined above.

A "urea" group is a radical of the formula: —N(alkyl)C(O)N($R^{\#}$)$_2$, —N(alkyl)C(O)NH($R^{\#}$), —N(alkyl)C(O)$NH_2$, —NHC(O)N($R^{\#}$)$_2$, —NHC(O)NH($R^{\#}$), or —NH(CO)NH$R^{\#}$, wherein each alkyl and $R^{\#}$ are independently as defined above.

When the groups described herein, with the exception of alkyl group, are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxygen (=O); B(OH)$_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Heteroaryl Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18$^{th}$ eds., Mack Publishing, Easton Pa. (1990) or *Remington: The Science and Practice of Pharmacy*, 19$^{th}$ eds., Mack Publishing, Easton Pa. (1995).

As used herein and unless otherwise indicated, the term "stereoisomer" or "stereomerically pure" means one stereoisomer of a Heteroaryl Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Heteroaryl Compounds can have chiral centers and can occur as racemates, individual enantiomers or diastereomers, and mixtures thereof. All such isomeric forms are included within the embodiments disclosed herein, including mixtures thereof. The use of stereomerically pure forms of such Heteroaryl Compounds, as well as the use of mixtures of those forms are encompassed by the embodiments disclosed herein. For example, mixtures comprising equal or unequal amounts of the enantiomers of a particular Heteroaryl Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Heteroaryl Compounds can include E and Z isomers, or a mixture thereof, and cis and trans isomers or a mixture thereof. In certain embodiments, the Heteroaryl Compounds are isolated as either the cis or trans isomer. In other embodiments, the Heteroaryl Compounds are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

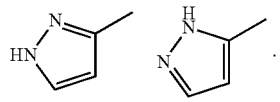

As readily understood by one skilled in the art, a wide variety of functional groups and other structures may exhibit tautomerism and all tautomers of compounds of formula (I) and formula (II) are within the scope of the present invention.

It should also be noted the Heteroaryl Compounds can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Heteroaryl Compounds as described herein, whether radioactive or not, are intended to be encompassed within the scope of the embodiments provided herein. In some embodiments, there are provided isotopologues of the Heteroaryl Compounds, for example, the isotopologues are deuterium, carbon-13, or nitrogen-15 enriched Heteroaryl Compounds.

"Treating" as used herein, means an alleviation, in whole or in part, of the disease or disorder, or symptoms associated with the disease or disorder, or slowing or halting of further progression or worsening of the disease or disorder, or symptoms associated with the disease or disorder.

"Preventing" as used herein, means prevention of the onset, recurrence, or spread of the disease or disorder, or symptoms associated with the disorder or disease, in a patient at risk for developing the disease or disorder.

The term "effective amount" in connection with an Heteroaryl Compound means, in one embodiment, an amount capable of alleviating, in whole or in part, symptoms associated with a disorder or disease, or slowing or halting further progression or worsening of those symptoms, or, in another embodiment, an amount capable of preventing or providing prophylaxis for the disease or disorder in a subject at risk for developing the disease or disorder as disclosed herein, such as cancer, inflammatory conditions, immunological conditions, neurodegenerative diseases, diabetes, obesity, neurological disorders, age-related diseases, or cardiovascular conditions, and conditions treatable or preventable by inhibition of a kinase pathway, for example, the mTOR/PI3K/Akt pathway. In one embodiment an effective amount of a Heteroaryl Compound is an amount that inhibits a kinase in a cell, such as, for example, in vitro or in vivo. In one embodiment the kinase is mTOR, DNA-PK, PI3K or a combination thereof. In some embodiments, the effective amount of the Heteroaryl Compound inhibits the kinase in a cell by 10%, 20%, 30%, 40%, 50%, 60%, 70%, 80%, 90% or 99%, compared to the activity of the kinase in an untreated cell. The effective amount of the Heteroaryl Compound, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of an Heteroaryl Compound disclosed herein may vary depending on the indication being treated, e.g., the effective amount of an Heteroaryl Compound would likely be different for treating patients suffering from, or at risk for, inflammatory conditions relative to the effective amount of the Compound for treating patients suffering from, or at risk of, a different disorder, e.g., cancer or a metabolic disorder.

The term "patient" includes an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

4.2 Synthesis of Heteroaryl Compounds

Provided herein are methods of preparing compounds having the following formula (I):

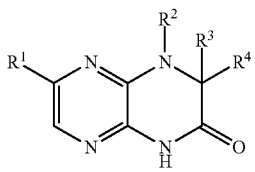
(I)

and pharmaceutically acceptable salts, tautomers, and stereoisomers thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ and $R^4$ are each independently H, substituted or unsubstituted $C_{1-8}$ alkyl, substituted or unsubstituted aryl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl, or $R^3$ and $R^4$, together with the atoms to which they are attached, form a substituted or unsubstituted cycloalkyl or substituted or unsubstituted heterocyclyl;

or $R^2$ and one of $R^3$ and $R^4$, together with the atoms to which they are attached, form a substituted or unsubstituted heterocyclyl;

provided the compound is not the compounds depicted below, namely:

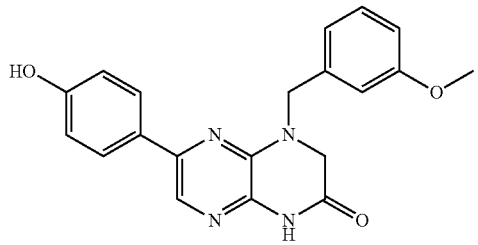 [SMILES: COc1cccc(CN2CC(=O)Nc3ncc(-c4ccc(O)cc4)nc32)c1]

6-(4-hydroxyphenyl)-4-(3-methoxybenzyl)-3,4-dihydropyrazino[2,3-b]pyrazin-2(1H)-one;

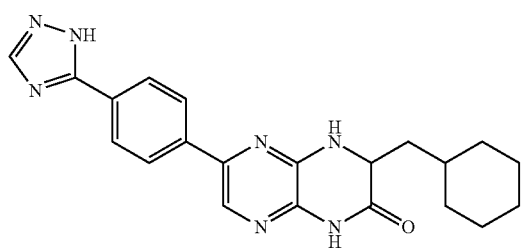 [SMILES: O=C1Nc2ncc(-c3ccc(-c4ncn[nH]4)cc3)nc2NC1CC1CCCCC1]

6-(4-(1H-1,2,4-triazol-5-yl)phenyl)-3-(cyclohexylmethyl)-3,4-dihydropyrazino[2,3-b]pyrazin-2(1H)-one;

or,

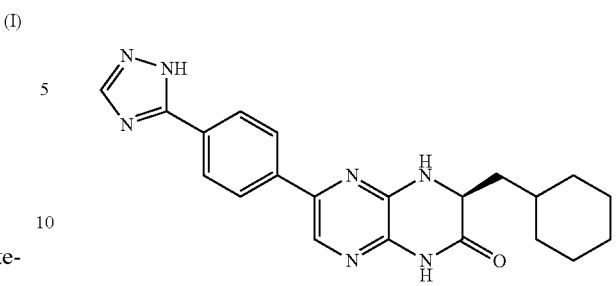

(R)-6-(4-(1H-1,2,4-triazol-5-yl)phenyl)-3-(cyclohexylmethyl)-3,4-dihydropyrazino[2,3-b]pyrazin-2(1H)-one.

Provided herein are methods of preparing a compound of formula (I),

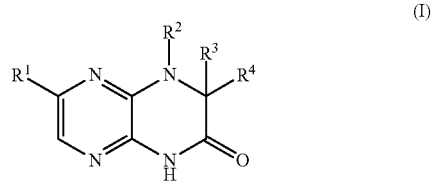
(I)

the method comprising contacting a compound of formula (III)

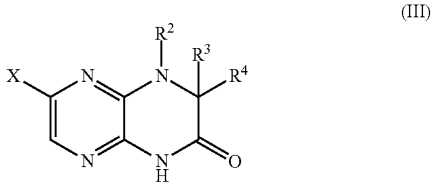
(III)

with $R^1$—Y in a solvent, in the presence of a palladium catalyst, wherein said contacting occurs under conditions suitable to provide a compound of formula (I), wherein $R^1$, $R^2$, $R^3$ and $R^4$ are as defined herein, and X is halogen, $B(OR^+)_2$ or $Sn(R^{++})_3$;
Y is halogen, triflate, $B(OR^+)_2$ or $Sn(R^{++})_3$; wherein
a) when X is halogen (for example Br, Cl, or I), then Y is $B(OR^+)_2$ or $Sn(R^{++})_3$; or
b) when Y is halogen (for example Br, Cl, or I) or triflate, then X is $B(OR^+)_2$ or $Sn(R^{++})_3$;
wherein each $R^+$ is independently hydrogen or substituted or unsubstituted $C_{1-3}$ alkyl, or each $R^+$, together with the boron atom and the atoms to which they are attached, form a cyclic boronate; and $R^{++}$ is a $C_{1-4}$ alkyl.

Typically the solvent is dimethylformamide, isopropanol, dioxane, toluene, dimethylacetamide, tetrahydrofuran, acetonitrile, isopropyl acetate, dimethyl sulfoxide, acetone, methanol, methyl t-butyl ether or a combination thereof, with or without the presence of water, and the palladium catalyst is dichloro[1,1'-bis(diphenylphosphino)-ferrocene]palladium (II)dichloro-methane), palladium(dba)$_2$/tri-o-tolylphosphine, dichloro[1,1'-bis(ditert-butylphosphino)ferrocene]palladium, dichlorobis(p-dimethylamino phenylditbutylphosphine)palladium(II), tetrakis(triphenylphosphine)palladium(0), or palladium (II) acetate/4,5-bis (diphenylphosphino)-9,9-dimethylxanthene. In some embodiments when X or Y is a halogen, the halogen is Br. In some embodiments when X or Y is $B(OR^+)_2$, the contacting occurs in the presence of a base such as sodium carbonate, triethyl amine, diisopropylethyl amine, piperidine, pyridine, cesium carbonate, potassium carbonate, potassium phosphate, or sodium hydroxide. In some such embodiments, $B(OR^+)_2$ is $B(OH)_2$ or $B(—OC(CH_3)_2C(CH_3)_2O—)$. In other embodiments, when X or Y is $Sn(R^{++})_3$ the contacting optionally occurs in the presence of a base such as triethylamine, sodium carbonate, diisopropylethyl amine, piperidine, pyridine, cesium carbonate, potassium carbonate, potassium phosphate, or sodium hydroxide. In some such embodiments, $R^{++}$ is methyl or n-butyl.

Also provided are methods of preparing a compound of formula (III),

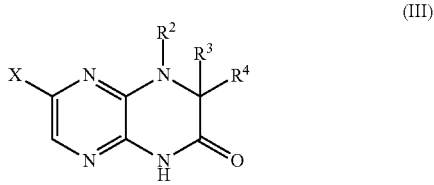

the method comprising contacting a compound of formula (IV)

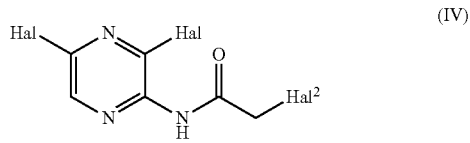

with $R^2$—$NH_2$ in a solvent, such as acetonitrile or tetrahydrofuran, in the presence of a base, such as triethylamine or diisopropylethylamine, wherein said contacting occurs under conditions suitable to provide a compound of formula (III), wherein $R^2$ is as defined herein, $R^3$ and $R^4$ are H, X is a halogen such as Br, Hal is a halogen such as Br, and $Hal^2$ is Br or I.

Also provided are methods of preparing a compound of formula (III),

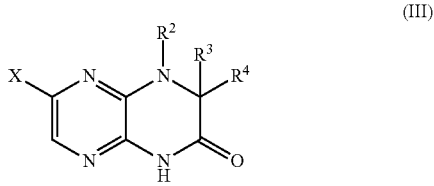

the method comprising cyclizing a compound of formula (V)

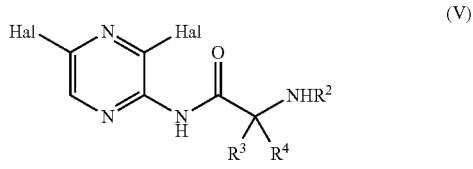

in a solvent, such as acetonitrile, in the presence of a palladium catalyst, such as palladium(II)acetate, a ligand, such as 4,5-bis-(diphenylphosphino)-9,9-dimethylxanthene, and a base, such as sodium bicarbonate, wherein said cyclization occurs under conditions suitable to provide a compound of formula (III), wherein $R^2$ is as defined herein, $R^3$ and $R^4$ are as described herein, X is a halogen such as Br, and Hal is a halogen such as Br.

In certain embodiments, provided herein are salts (including pharmaceutically acceptable salts), solvates and hydrates of compounds of formula (III), formula (IV) and formula (V).

In some embodiments of compounds of formula (I), $R^1$ is substituted or unsubstituted aryl or substituted or unsubstituted heteroaryl. In one embodiment, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, substituted or unsubstituted triazolyl or pyrazolyl), halogen (for example, fluorine), aminocarbonyl, cyano, hydroxyalkyl (for example, hydroxypropyl), and hydroxy. In other embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, cyano, hydroxyalkyl, —OR, and —$NR_2$, wherein each R is independently H, or a substituted or unsubstituted $C_{1-4}$ alkyl. In yet other embodiments, $R^1$ is 1H-pyrrolo[2,3-b]pyridyl or benzimidazolyl, each optionally substituted with one or more substituents independently selected from the group consisting of substituted or unsubstituted $C_{1-8}$ alkyl, and —$NR_2$, wherein each R is independently H, or a substituted or unsubstituted $C_{1-4}$ alkyl.

In some embodiments of compounds of formula (I), $R^1$ is

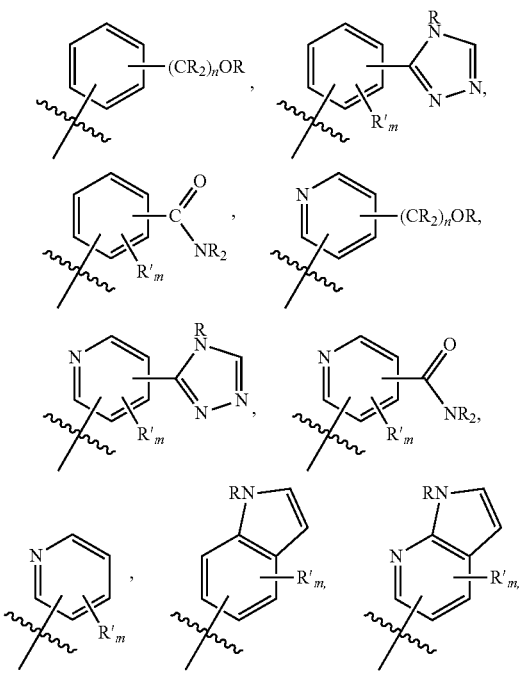

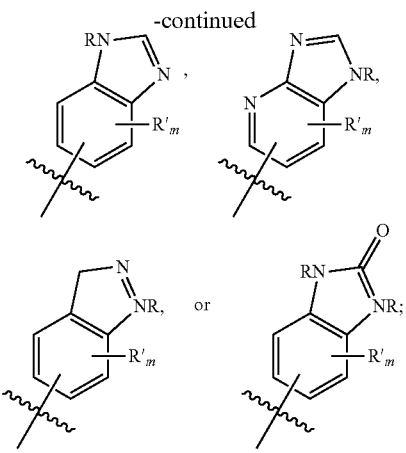

wherein R is at each occurrence independently H, or a substituted or unsubstituted $C_{1-4}$ alkyl (for example, methyl); R' is at each occurrence independently a substituted or unsubstituted $C_{1-4}$ alkyl, halogen (for example, fluorine), cyano, —OR, or —NR$_2$; m is 0-3; and n is 0-3. It will be understood by those skilled in the art that any of the substituents R' may be attached to any suitable atom of any of the rings in the fused ring systems. It will also be understood by those skilled in the art that the connecting bond of $R^1$ (designated by the bisecting wavy line) may be attached to any of the atoms in any of the rings in the fused ring systems.

In some embodiments of compounds of formula (I), $R^1$ is

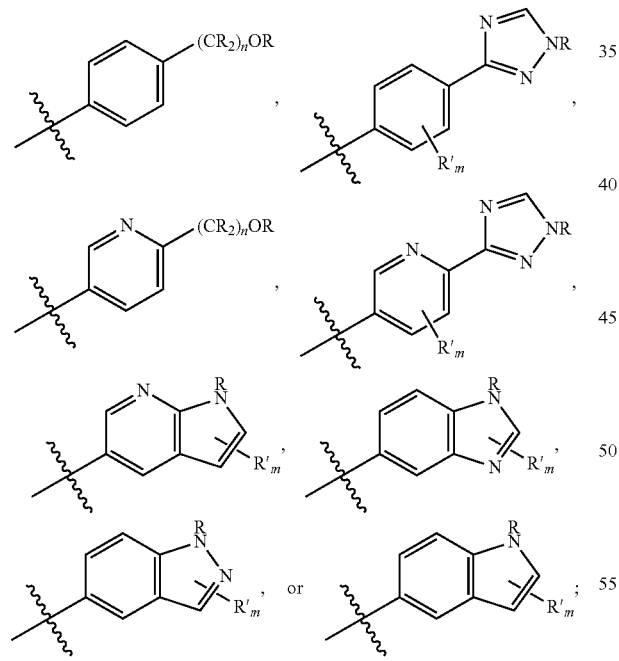

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR, or —NR$_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

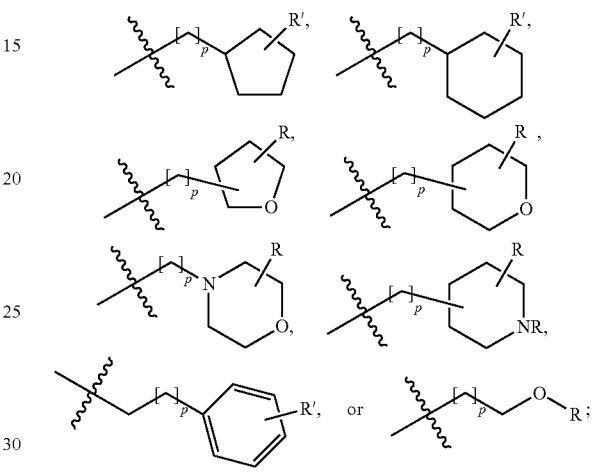

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In some such embodiments, $R^2$ is H, $C_{1-4}$ alkyl, ($C_{1-4}$alkyl) (OR),

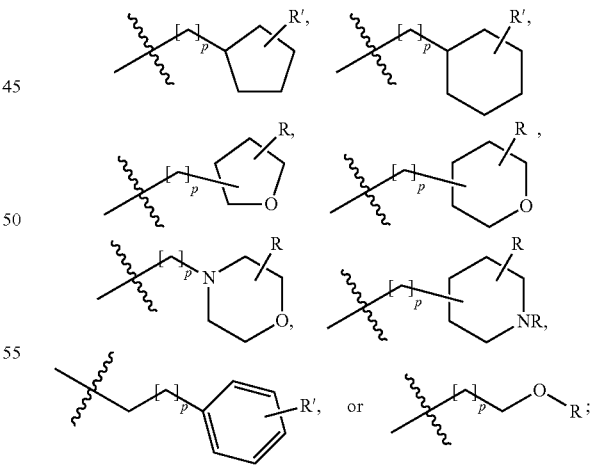

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In some other embodiments of compounds of formula (I), $R^2$ and one of $R^3$ and $R^4$ together with the atoms to which they are attached form a substituted or unsubstituted heterocyclyl. For example, in some embodiments, the compound of formula (I) is

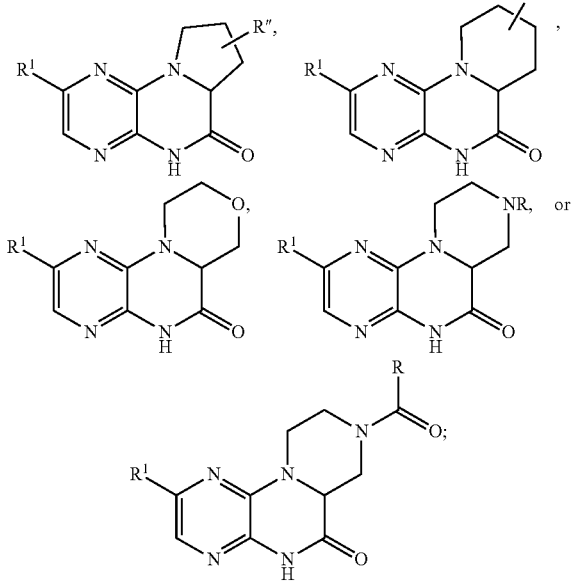

wherein R is at each occurrence independently H, or a substituted or unsubstituted $C_{1-4}$ alkyl; R" is H, OR, or a substituted or unsubstituted $C_{1-4}$ alkyl; and $R^1$ is as defined herein.

In some embodiments of compounds of formula (I), $R^3$ and $R^4$ are both H. In others, one of $R^3$ and $R^4$ is H and the other is other than H. In still others, one of $R^3$ and $R^4$ is $C_{1-4}$ alkyl (for example, methyl) and the other is H. In still others, both of $R^3$ and $R^4$ are $C_{1-4}$ alkyl (for example, methyl).

In some such embodiments described above, $R^1$ is substituted or unsubstituted aryl, or substituted or unsubstituted heteroaryl. For example, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, halogen, aminocarbonyl, cyano, hydroxyalkyl and hydroxy. In others, $R^1$ is pyridyl substituted with one or more substituents independently selected from the group consisting of cyano, substituted or unsubstituted $C_{1-8}$ alkyl, substituted or unsubstituted heterocyclyl, hydroxyalkyl, halogen, aminocarbonyl, —OR, and —$NR_2$, wherein each R is independently H, or a substituted or unsubstituted $C_{1-4}$ alkyl. In others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl In certain embodiments, the compounds of formula (I) have an $R^1$ group set forth herein and an $R^2$ group set forth herein.

In some embodiments of compounds of formula (I), the compound at a concentration of 10 μM inhibits mTOR, DNA-PK, or PI3K or a combination thereof, by at least about 50%. Compounds of formula (I) may be shown to be inhibitors of the kinases above in any suitable assay system, such as those described in the Examples herein.

In some embodiments of compounds of formula (I), the compound is
 6-(1H-pyrrolo[2,3-b]pyridin-3-yl)-4-(2-(tetrahydro-2H-pyran-4-yl)ethyl)-3,4-dihydropyrazino[2,3-b]pyrazin-2 (1H)-one;
 6-(4-methyl-6-(1H-1,2,4-triazol-3-yl)pyridin-3-yl)-4-((tetrahydro-2H-pyran-4-yl)methyl)-3,4-dihydropyrazino[2, 3-b]pyrazin-2(1H)-one;
 6-(5-fluoro-2-methyl-4-(1H-1,2,4-triazol-3-yl)phenyl)-4-((trans-4-methoxycyclohexyl)methyl)-3,4-dihydropyrazino[2,3-b]pyrazin-2(1H)-one;
 6-(5-fluoro-2-methyl-4-(1H-1,2,4-triazol-3-yl)phenyl)-4-((cis-4-methoxycyclohexyl)methyl)-3,4-dihydropyrazino [2,3-b]pyrazin-2(1H)-one;
 6-(6-(1H-1,2,4-triazol-3-yl)pyridin-3-yl)-4-((trans-4-methoxycyclohexyl)methyl)-3,4-dihydropyrazino[2,3-b] pyrazin-2(1H)-one;
 6-(5-fluoro-2-methyl-4-(1H-1,2,4-triazol-3-yl)phenyl)-4-((trans-4-hydroxycyclohexyl)methyl)-3,4-dihydropyrazino[2,3-b]pyrazin-2(1H)-one;
 6-(6-(1H-1,2,4-triazol-3-yl)pyridin-3-yl)-4-((cis-4-methoxycyclohexyl)methyl)-3,4-dihydropyrazino[2,3-b] pyrazin-2(1H)-one;
 6-(6-(1H-1,2,4-triazol-3-yl)pyridin-3-yl)-4-((trans-4-hydroxycyclohexyl)methyl)-3,4-dihydropyrazino[2,3-b] pyrazin-2(1H)-one;
 6-(6-(1H-1,2,4-triazol-3-yl)pyridin-3-yl)-4-(cis-4-hydroxycyclohexyl)-3,4-dihydropyrazino[2,3-b]pyrazin-2(1H)-one;
 6-(6-(1H-1,2,4-triazol-3-yl)pyridin-3-yl)-4-((cis-4-hydroxycyclohexyl)methyl)-3,4-dihydropyrazino[2,3-b]pyrazin-2 (1H)-one;
 6-(5-fluoro-2-methyl-4-(1H-1,2,4-triazol-3-yl)phenyl)-4-(trans-4-methoxycyclohexyl)-3,4-dihydropyrazino[2,3-b] pyrazin-2(1H)-one;
 6-(6-(1H-1,2,4-triazol-3-yl)pyridin-3-yl)-4-(trans-4-methoxycyclohexyl)-3,4-dihydropyrazino[2,3-b]pyrazin-2 (1H)-one;
 6-(6-(1H-1,2,4-triazol-3-yl)pyridin-3-yl)-4-(trans-4-hydroxycyclohexyl)-3,4-dihydropyrazino[2,3-b]pyrazin-2 (1H)-one;
 6-(5-fluoro-2-methyl-4-(1H-1,2,4-triazol-3-yl)phenyl)-4-((cis-4-hydroxycyclohexyl)methyl)-3,4-dihydropyrazino [2,3-b]pyrazin-2(1H)-one;
 6-(6-(1H-1,2,4-triazol-3-yl)pyridin-3-yl)-4-(cis-4-methoxycyclohexyl)-3,4-dihydropyrazino[2,3-b]pyrazin-2(1H)-one;
 6-(6-(1H-1,2,4-triazol-3-yl)pyridin-3-yl)-4-(2-methoxyethyl)-3,4-dihydropyrazino[2,3-b]pyrazin-2(1H)-one;
 6-(6-(1H-1,2,4-triazol-3-yl)pyridin-3-yl)-4-isopropyl-3,4-dihydropyrazino[2,3-b]pyrazin-2(1H)-one;
 6-(5-fluoro-2-methyl-4-(1H-1,2,4-triazol-3-yl)phenyl)-4-(cis-4-hydroxycyclohexyl)-3,4-dihydropyrazino[2,3-b] pyrazin-2(1H)-one;
 6-(5-fluoro-2-methyl-4-(1H-1,2,4-triazol-3-yl)phenyl)-4-(cis-4-methoxycyclohexyl)-3,4-dihydropyrazino[2,3-b] pyrazin-2(1H)-one;
 6-(5-fluoro-2-methyl-4-(1H-1,2,4-triazol-3-yl)phenyl)-4-(2-methoxyethyl)-3,4-dihydropyrazino[2,3-b]pyrazin-2 (1H)-one;
 6-(6-(1H-1,2,4-triazol-3-yl)pyridin-3-yl)-4-(tetrahydro-2H-pyran-4-yl)-3,4-dihydropyrazino[2,3-b]pyrazin-2(1H)-one;
 6-(6-(1H-1,2,4-triazol-3-yl)pyridin-3-yl)-4-ethyl-3,4-dihydropyrazino[2,3-b]pyrazin-2(1H)-one;

6-(5-fluoro-2-methyl-4-(1H-1,2,4-triazol-3-yl)phenyl)-4-(trans-4-hydroxycyclohexyl)-3,4-dihydropyrazino[2,3-b]pyrazin-2(1H)-one;
6-(5-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;
6-(5-fluoro-2-methyl-4-(1H-1,2,4-triazol-3-yl)phenyl)-4-isopropyl-3,4-dihydropyrazino[2,3-b]pyrazin-2(1H)-one;
4-ethyl-6-(5-fluoro-2-methyl-4-(1H-1,2,4-triazol-3-yl)phenyl)-3,4-dihydropyrazino[2,3-b]pyrazin-2(1H)-one;
6-(3-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;
6-(3-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;
6-(3-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;
4-(2-methoxyethyl)-6-(4-methyl-6-(1H-1,2,4-triazol-3-yl)pyridin-3-yl)-3,4-dihydropyrazino[2,3-b]pyrazin-2(1H)-one;
6-(3-(1H-1,2,4-triazol-5-yl)phenyl)-4-(2-(tetrahydro-2H-pyran-4-yl)ethyl)-3,4-dihydropyrazino[2,3-b]pyrazin-2(1H)-one;
5-(8-(2-methoxyethyl)-6-oxo-5,6,7,8-tetrahydropyrazino[2,3-b]pyrazin-2-yl)-4-methylpicolinamide;
3-(6-oxo-8-(2-(tetrahydro-2H-pyran-4-yl)ethyl)-5,6,7,8-tetrahydropyrazino[2,3-b]pyrazin-2-yl)benzamide;
3-(6-oxo-8-(2-(tetrahydro-2H-pyran-4-yl)ethyl)-5,6,7,8-tetrahydropyrazino[2,3-b]pyrazin-2-yl)benzonitrile;
5-(8-(trans-4-methoxycyclohexyl)-6-oxo-5,6,7,8-tetrahydropyrazino[2,3-b]pyrazin-2-yl)-4-methylpicolinamide;
6-(1H-imidazo[4,5-b]pyridin-6-yl)-4-(2-(tetrahydro-2H-pyran-4-yl)ethyl)-3,4-dihydropyrazino[2,3-b]pyrazin-2(1H)-one;
6-(1H-indazol-6-yl)-4-(2-(tetrahydro-2H-pyran-4-yl)ethyl)-3,4-dihydropyrazino[2,3-b]pyrazin-2(1H)-one;
4-((1R,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-((1S,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-((1R,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-((1S,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;
4-ethyl-6-(2-methyl-6-(4H-1,2,4-triazol-3-yl)pyridin-3-yl)-3,4-dihydropyrazino[2,3-b]pyrazin-2(1H)-one;
6-(1H-pyrrolo[2,3-b]pyridin-5-yl)-4-(2-(tetrahydro-2H-pyran-4-yl)ethyl)-3,4-dihydropyrazino[2,3-b]pyrazin-2(1H)-one;
6-(1H-indol-6-yl)-4-(2-(tetrahydro-2H-pyran-4-yl)ethyl)-3,4-dihydropyrazino[2,3-b]pyrazin-2(1H)-one;
6-(1H-indol-5-yl)-4-(2-(tetrahydro-2H-pyran-4-yl)ethyl)-3,4-dihydropyrazino[2,3-b]pyrazin-2(1H)-one;
4-(((1R,3S)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;
4-(((1S,3R)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;
6-(3-fluoro-2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
6-(3-fluoro-2-methyl-4-(4H-1,2,4-triazol-3-yl)phenyl)-4-(2-methoxyethyl)-3,4-dihydropyrazino[2,3-b]pyrazin-2(1H)-one;
3,3-dimethyl-6-(4-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;
6-(6-(2-hydroxypropan-2-yl)pyridin-3-yl)-4-((1R,3S)-3-methoxycyclopentyl)-3,4-dihydropyrazino[2,3-b]pyrazin-2(1H)-one;
6-(6-(2-hydroxypropan-2-yl)pyridin-3-yl)-4-((1S,3R)-3-methoxycyclopentyl)-3,4-dihydropyrazino[2,3-b]pyrazin-2(1H)-one;
6-(6-(2-hydroxypropan-2-yl)pyridin-3-yl)-4-(((1S,3S)-3-methoxycyclopentyl)methyl)-3,4-dihydropyrazino[2,3-b]pyrazin-2(1H)-one;
6-(6-(2-hydroxypropan-2-yl)pyridin-3-yl)-4-(((1R,3R)-3-methoxycyclopentyl)methyl)-3,4-dihydropyrazino[2,3-b]pyrazin-2(1H)-one;
6-(6-(2-hydroxypropan-2-yl)pyridin-3-yl)-4-((1S,3S)-3-methoxycyclopentyl)-3,4-dihydropyrazino[2,3-b]pyrazin-2(1H)-one;
6-(6-(2-hydroxypropan-2-yl)pyridin-3-yl)-4-((1R,3R)-3-methoxycyclopentyl)-3,4-dihydropyrazino[2,3-b]pyrazin-2(1H)-one;
6-(6-(2-hydroxypropan-2-yl)pyridin-3-yl)-4-(((1R,3S)-3-methoxycyclopentyl)methyl)-3,4-dihydropyrazino[2,3-b]pyrazin-2(1H)-one;
6-(6-(2-hydroxypropan-2-yl)pyridin-3-yl)-4-(((1S,3R)-3-methoxycyclopentyl)methyl)-3,4-dihydropyrazino[2,3-b]pyrazin-2(1H)-one;
6-(3-fluoro-4-(4H-1,2,4-triazol-3-yl)phenyl)-4-(2-methoxyethyl)-3,4-dihydropyrazino[2,3-b]pyrazin-2(1H)-one;
6-(3-fluoro-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
7'-(2-methyl-4-(4H-1,2,4-triazol-3-yl)phenyl)-1'-((tetrahydro-2H-pyran-4-yl)methyl)-1'H-spiro[cyclopentane-1,2'-pyrazino[2,3-b]pyrazin]-3'(4'H)-one;
7'-(2-methyl-4-(4H-1,2,4-triazol-3-yl)phenyl)-1'-((tetrahydro-2H-pyran-4-yl)methyl)-1'H-spiro[cyclobutane-1,2'-pyrazino[2,3-b]pyrazin]-3'(4'H)-one;
4-(cyclopropylmethyl)-6-(6-(2-hydroxypropan-2-yl)pyridin-3-yl)-3,4-dihydropyrazino[2,3-b]pyrazin-2(1H)-one;
7'-(2-methyl-4-(4H-1,2,4-triazol-3-yl)phenyl)-1'H-spiro[cyclopentane-1,2'-pyrazino[2,3-b]pyrazin]-3'(4'H)-one;
7'-(2-methyl-4-(4H-1,2,4-triazol-3-yl)phenyl)-1'H-spiro[cyclobutane-1,2'-pyrazino[2,3-b]pyrazin]-3'(4'H)-one;
7'-(2-methyl-4-(4H-1,2,4-triazol-3-yl)phenyl)-1'H-spiro[cyclopropane-1,2'-pyrazino[2,3-b]pyrazin]-3'(4'H)-one;
(R)-6-(4-(4H-1,2,4-triazol-3-yl)phenyl)-4-((tetrahydrofuran-2-yl)methyl)-3,4-dihydropyrazino[2,3-b]pyrazin-2(1H)-one;
(S)-6-(4-(4H-1,2,4-triazol-3-yl)phenyl)-4-((tetrahydrofuran-2-yl)methyl)-3,4-dihydropyrazino[2,3-b]pyrazin-2(1H)-one;
6-(1H-indazol-5-yl)-4-(2-(tetrahydro-2H-pyran-4-yl)ethyl)-3,4-dihydropyrazino[2,3-b]pyrazin-2(1H)-one;
4-(6-oxo-8-(2-(tetrahydro-2H-pyran-4-yl)ethyl)-5,6,7,8-tetrahydropyrazino[2,3-b]pyrazin-2-yl)benzamide;
4-(2-methoxyethyl)-3,3-dimethyl-6-(2-methyl-4-(4H-1,2,4-triazol-3-yl)phenyl)-3,4-dihydropyrazino[2,3-b]pyrazin-2(1H)-one;
4-ethyl-3,3-dimethyl-6-(2-methyl-4-(4H-1,2,4-triazol-3-yl)phenyl)-3,4-dihydropyrazino[2,3-b]pyrazin-2(1H)-one;

6-(2-methyl-4-(4H-1,2,4-triazol-3-yl)phenyl)-3,4-dihydropyrazino[2,3-b]pyrazin-2(1H)-one;

3,3-dimethyl-6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

(R)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;

3,3-dimethyl-6-(2-methyl-4-(4H-1,2,4-triazol-3-yl)phenyl)-4-((tetrahydro-2H-pyran-4-yl)methyl)-3,4-dihydropyrazino[2,3-b]pyrazin-2(1H)-one;

6-(6-(2-hydroxypropan-2-yl)-4-methylpyridin-3-yl)-4-(trans-4-methoxycyclohexyl)-3,4-dihydropyrazino[2,3-b]pyrazin-2(1H)-one;

6-(6-(2-hydroxypropan-2-yl)-4-methylpyridin-3-yl)-4-((tetrahydro-2H-pyran-4-yl)methyl)-3,4-dihydropyrazino[2,3-b]pyrazin-2(1H)-one;

3,3-dimethyl-6-(2-methyl-4-(4H-1,2,4-triazol-3-yl)phenyl)-3,4-dihydropyrazino[2,3-b]pyrazin-2(1H)-one;

3,3-dimethyl-6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

6-(6-(2-hydroxypropan-2-yl)-2-methylpyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)-2-methylpyridin-3-yl)-4-(trans-4-methoxycyclohexyl)-3,4-dihydropyrazino[2,3-b]pyrazin-2(1H)-one;

(S)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;

3,3-dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(6-(2-hydroxypropan-2-yl)pyridin-3-yl)-3,3-dimethyl-4-(2-(tetrahydro-2H-pyran-4-yl)ethyl)-3,4-dihydropyrazino[2,3-b]pyrazin-2(1H)-one;

6-(4-(2-hydroxypropan-2-yl)phenyl)-4-(trans-4-methoxycyclohexyl)-3,4-dihydropyrazino[2,3-b]pyrazin-2(1H)-one;

6-(4-(2-hydroxypropan-2-yl)phenyl)-4-((trans-4-methoxycyclohexyl)methyl)-3,4-dihydropyrazino[2,3-b]pyrazin-2(1H)-one;

4-(cis-4-methoxycyclohexyl)-6-(2-methyl-6-(4H-1,2,4-triazol-3-yl)pyridin-3-yl)-3,4-dihydropyrazino[2,3-b]pyrazin-2(1H)-one;

4-(trans-4-methoxycyclohexyl)-6-(2-methyl-6-(4H-1,2,4-triazol-3-yl)pyridin-3-yl)-3,4-dihydropyrazino[2,3-b]pyrazin-2(1H)-one;

6-(4-(2-hydroxypropan-2-yl)phenyl)-4-((tetrahydro-2H-pyran-4-yl)methyl)-3,4-dihydropyrazino[2,3-b]pyrazin-2(1H)-one;

4-(2-methoxyethyl)-6-(2-methyl-6-(4H-1,2,4-triazol-3-yl)pyridin-3-yl)-3,4-dihydropyrazino[2,3-b]pyrazin-2(1H)-one;

9-(6-(4H-1,2,4-triazol-3-yl)-3-pyridyl)-6,11,4a-trihydromorpholino[4,3-e]pyrazino[2,3-b]pyrazin-5-one;

6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

5-(8-(cis-4-methoxycyclohexyl)-6-oxo-5,6,7,8-tetrahydropyrazino[2,3-b]pyrazin-2-yl)-6-methylpicolinonitrile;

6-(6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

9-(4-(4H-1,2,4-triazol-3-yl)-2-methylphenyl)-3-(2-methoxyacetyl)-6,11,4a-trihydropiperazino[1,2-e]pyrazino[2,3-b]pyrazin-5-one;

9-(4-(4H-1,2,4-triazol-3-yl)-2-methylphenyl)-6,11,4a-trihydropiperazino[1,2-e]pyrazino[2,3-b]pyrazin-5-one;

9-(4-(4H-1,2,4-triazol-3-yl)-2-methylphenyl)-3-(2-methoxyethyl)-6,11,4a-trihydropiperazino[1,2-e]pyrazino[2,3-b]pyrazin-5-one;

4-(cyclopentylmethyl)-6-(2-methyl-6-(4H-1,2,4-triazol-3-yl)pyridin-3-yl)-3,4-dihydropyrazino[2,3-b]pyrazin-2(1H)-one;

9-(6-(4H-1,2,4-triazol-3-yl)-2-methyl-3-pyridyl)-6,11,4a-trihydromorpholino[4,3-e]pyrazino[2,3-b]pyrazin-5-one;

4-(trans-4-hydroxycyclohexyl)-6-(6-(2-hydroxypropan-2-yl)pyridin-3-yl)-3,4-dihydropyrazino[2,3-b]pyrazin-2(1H)-one;

4-(cis-4-hydroxycyclohexyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-((tetrahydrofuran-3-yl)methyl)-3,4-dihydropyrazino[2,3-b]pyrazin-2(1H)-one;

4-(cyclopentylmethyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-neopentyl-3,4-dihydropyrazino[2,3-b]pyrazin-2(1H)-one;

6-(6-(2-hydroxypropan-2-yl)pyridin-3-yl)-4-isobutyl-3,4-dihydropyrazino[2,3-b]pyrazin-2(1H)-one;

3-methyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(6-(2-hydroxypropan-2-yl)pyridin-3-yl)-4-(piperidin-4-yl)-3,4-dihydropyrazino[2,3-b]pyrazin-2(1H)-one;

6-(6-(2-hydroxypropan-2-yl)pyridin-3-yl)-4-(2-(tetrahydro-2H-pyran-3-yl)ethyl)-3,4-dihydropyrazino[2,3-b]pyrazin-2(1H)-one;

8-(4-(4H-1,2,4-triazol-3-yl)-2-methylphenyl)(3aS,2R)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2R,3aR)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2S,3aR)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2S,3aS)-2-methoxy-5,10,3a-trihydropyrazino[2,3-b]pyrrolidino[1,2-e]pyrazin-4-one;

6-(6-(2-hydroxypropan-2-yl)pyridin-3-yl)-4-(3-methoxypropyl)-3,4-dihydropyrazino[2,3-b]pyrazin-2(1H)-one;

(S)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;

(R)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;

6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

9-(4-(4H-1,2,4-triazol-3-yl)-2-methylphenyl)-3-methyl-6,11,4a-trihydropiperazino[1,2-e]pyrazino[2,3-b]pyrazin-5-one;

9-(4-(4H-1,2,4-triazol-3-yl)phenyl)-6,11,4a-trihydromorpholino[4,3-e]pyrazino[2,3-b]pyrazin-5-one;

9-(4-(4H-1,2,4-triazol-3-yl)-2-methylphenyl)-6,11,4a-trihydropiperidino[1,2-e]pyrazino[2,3-b]pyrazin-5-one;

6-(6-(2-hydroxypropan-2-yl)pyridin-3-yl)-4-(trans-4-methoxycyclohexyl)-3,4-dihydropyrazino[2,3-b]pyrazin-2(1H)-one;

6-(6-(2-hydroxypropan-2-yl)pyridin-3-yl)-4-(cis-4-methoxycyclohexyl)-3,4-dihydropyrazino[2,3-b]pyrazin-2(1H)-one;
6-(6-(2-hydroxypropan-2-yl)pyridin-3-yl)-4-(2-morpholinoethyl)-3,4-dihydropyrazino[2,3-b]pyrazin-2(1H)-one;
6-(6-(2-hydroxypropan-2-yl)pyridin-3-yl)-4-phenethyl-3,4-dihydropyrazino[2,3-b]pyrazin-2(1H)-one;
6-(6-(2-hydroxypropan-2-yl)pyridin-3-yl)-4-(tetrahydro-2H-pyran-4-yl)-3,4-dihydropyrazino[2,3-b]pyrazin-2(1H)-one;
4-(cyclohexylmethyl)-6-(6-(2-hydroxypropan-2-yl)pyridin-3-yl)-3,4-dihydropyrazino[2,3-b]pyrazin-2(1H)-one;
6-(6-(2-hydroxypropan-2-yl)pyridin-3-yl)-4-((trans-4-methoxycyclohexyl)methyl)-3,4-dihydropyrazino[2,3-b]pyrazin-2(1H)-one;
6-(6-(2-hydroxypropan-2-yl)pyridin-3-yl)-4-((cis-4-methoxycyclohexyl)methyl)-3,4-dihydropyrazino[2,3-b]pyrazin-2(1H)-one;
(R)-6-(6-(2-hydroxypropan-2-yl)pyridin-3-yl)-4-(tetrahydrofuran-3-yl)-3,4-dihydropyrazino[2,3-b]pyrazin-2(1H)-one;
(S)-6-(6-(2-hydroxypropan-2-yl)pyridin-3-yl)-4-(tetrahydrofuran-3-yl)-3,4-dihydropyrazino[2,3-b]pyrazin-2(1H)-one;
6-(6-(2-hydroxypropan-2-yl)pyridin-3-yl)-4-phenyl-3,4-dihydropyrazino[2,3-b]pyrazin-2(1H)-one;
(S)-6-(6-(2-hydroxypropan-2-yl)pyridin-3-yl)-3-methyl-4-(2-(tetrahydro-2H-pyran-4-yl)ethyl)-3,4-dihydropyrazino[2,3-b]pyrazin-2(1H)-one;
9-[6-(1-hydroxy-isopropyl)-3-pyridyl]-6,11,4a-trihydromorpholino[4,3-e]pyrazino[2,3-b]pyrazin-5-one;
6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one;
6-(6-(2-hydroxypropan-2-yl)pyridin-3-yl)-4-(2-methoxyethyl)-3,4-dihydropyrazino[2,3-b]pyrazin-2(1H)-one;
6-(2-amino-7-methyl-1H-benzo[d]imidazol-5-yl)-4-(3-(trifluoromethyl)benzyl)-3,4-dihydropyrazino[2,3-b]pyrazin-2(1H)-one;
6-(6-(2-hydroxypropan-2-yl)pyridin-3-yl)-4-(3-(trifluoromethyl)benzyl)-3,4-dihydropyrazino[2,3-b]pyrazin-2(1H)-one;
9-(4-(4H-1,2,4-triazol-3-yl)-2-methylphenyl)-6,11,4a-trihydromorpholino[4,3-e]pyrazino[2,3-b]pyrazin-5-one;
6-(4-methyl-2-(methylamino)-1H-benzo[d]imidazol-6-yl)-4-(2-(tetrahydro-2H-pyran-4-yl)ethyl)-3,4-dihydropyrazino[2,3-b]pyrazin-2(1H)-one;
8-(4-(4H-1,2,4-triazol-3-yl)-2-methylphenyl)-5,10,3a-trihydropyrazino[2,3-b]pyrrolidino[1,2-e]pyrazin-4-one;
6-(4-(4H-1,2,4-triazol-3-yl)phenyl)-4-ethyl-3,4-dihydropyrazino[2,3-b]pyrazin-2(1H)-one;
6-(4-(4H-1,2,4-triazol-3-yl)phenyl)-4-((tetrahydro-2H-pyran-4-yl)methyl)-3,4-dihydropyrazino[2,3-b]pyrazin-2(1H)-one;
6-(6-(2-hydroxypropan-2-yl)pyridin-3-yl)-4-(2-(tetrahydro-2H-pyran-4-yl)ethyl)-3,4-dihydropyrazino[2,3-b]pyrazin-2(1H)-one;
6-(4-(4H-1,2,4-triazol-3-yl)phenyl)-4-(2-methoxyethyl)-3,4-dihydropyrazino[2,3-b]pyrazin-2(1H)-one;
6-(4-(4H-1,2,4-triazol-3-yl)phenyl)-4-(3-(trifluoromethyl)benzyl)-3,4-dihydropyrazino[2,3-b]pyrazin-2(1H)-one;
6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;
6-(4-methyl-1H-benzo[d]imidazol-6-yl)-4-(2-(tetrahydro-2H-pyran-4-yl)ethyl)-3,4-dihydropyrazino[2,3-b]pyrazin-2(1H)-one;
6-(4-(2-hydroxypropan-2-yl)phenyl)-4-(2-(tetrahydro-2H-pyran-4-yl)ethyl)-3,4-dihydropyrazino[2,3-b]pyrazin-2(1H)-one; or
6-(4-(1H-1,2,4-triazol-5-yl)phenyl)-4-(2-(tetrahydro-2H-pyran-4-yl)ethyl)-3,4-dihydropyrazino[2,3-b]pyrazin-2(1H)-one.

Further provided herein are methods of preparing compounds having the following formula (II):

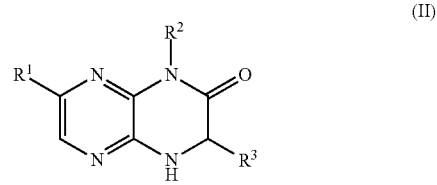

and pharmaceutically acceptable salts, tautomers, and stereoisomers thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl;

provided the compound of formula (II) is not 7-(4-hydroxyphenyl)-1-(3-methoxybenzyl)-3,4-dihydropyrazino[2,3-b]pyrazin-2(1H)-one, depicted below:

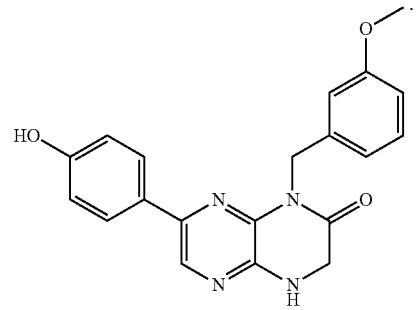 [SMILES: COc1cccc(CN2C(=O)CNc3ncc(-c4ccc(O)cc4)nc32)c1]

Also provided are methods of preparing a compound of formula (II),

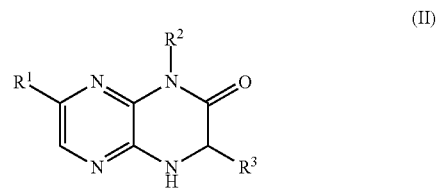

the method comprising contacting a compound of formula (VI)

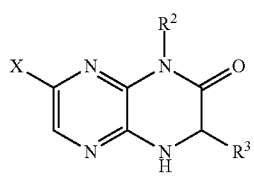

(VI)

with R¹—Y in a solvent, in the presence of a palladium catalyst, wherein said contacting occurs under conditions suitable to provide a compound of formula (I), wherein R¹, R², and R³ are as defined herein, and a) when X is halogen (for example Br, Cl, or I) then Y is $B(OR^+)_2$ or $Sn(R^{++})_3$; or b) when Y is halogen (for example Br, Cl, or I) or triflate, then X is $B(OR^+)_2$ or $Sn(R^{++})_3$;

wherein each $R^+$ is independently hydrogen or substituted or unsubstituted $C_{1-3}$ alkyl, or each $R^+$, together with the boron atom and the atoms to which they are attached, form a cyclic boronate; and each $R^{++}$ is a $C_{1-3}$ alkyl.

Typically the solvent is dimethylformamide, isopropanol, dioxane, toluene, dimethylacetamide, tetrahydrofuran, acetonitrile, isopropyl acetate, dimethyl sulfoxide, acetone, methanol, methyl t-butyl ether or a combination thereof, with or without the presence of water, and the palladium catalyst is dichloro[1,1'-bis(diphenylphosphino)-ferrocene]palladium (II)dichloro-methane), palladium(dba)₂/tri-o-tolylphosphine, dichloro[1,1'-bis(ditert-butylphosphino)ferrocene]palladium, dichlorobis(p-dimethylamino phenylditbutylphosphine)palladium(II), tetrakis(triphenylphosphine) palladium(0), dichloro(2-diphenylphosphino ethyl trimethyl-ammonium)palladium, or palladium (II) acetate/4, 5-bis(diphenylphosphino)-9,9-dimethylxanthene. In some embodiments when X or Y is a halogen, the halogen is Br. In some embodiments when X or Y is $B(OR^+)_2$, the contacting occurs in the presence of a base such as sodium carbonate, triethyl amine, diisopropylethyl amine, piperidine, pyridine, cesium carbonate, potassium carbonate, potassium phosphate, or sodium hydroxide. In some such embodiments, $B(OR^+)_2$ is $B(OH)_2$ or $B(—OC(CH_3)_2C(CH_3)_2O—)$. In other embodiments, when X or Y is $Sn(R^{++})_3$ the contacting optionally occurs in the presence of a base such as triethylamine, sodium carbonate, diisopropylethyl amine, piperidine, pyridine, cesium carbonate, potassium carbonate, potassium phosphate, or sodium hydroxide. In some such embodiments, $R^{++}$ is methyl or n-butyl.

Also provided are methods of preparing a compound of formula (VI),

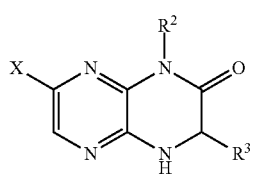

(VI)

the method comprising cyclizing a compound of formula (VII)

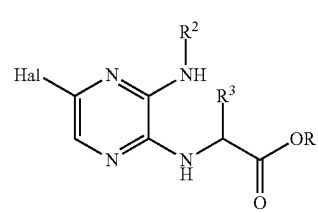

(VII)

in the presence of a base, such as potassium butoxide, or an acid, such as acetic acid, TFA, HCl, or phosphoric acid, wherein said cyclization occurs under conditions suitable to provide a compound of formula (VI), wherein R² and R³ are as defined herein, Hal is a halogen such as Br, and R is H or $C_{1-4}$ alkyl, or the alkali metal salt of the carboxylate, for example, the sodium salt. Typically, the cyclization is performed in a solvent, such as, for example, methanol or water.

Also provided are methods of preparing a compound of formula (VII),

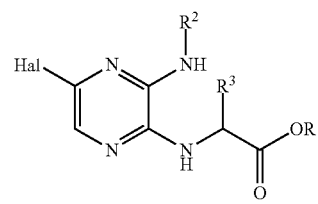

(VII)

the method comprising contacting a compound of formula (VIII)

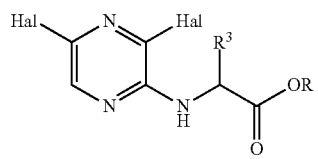

(VIII)

with R²—NH₂ in a solvent, such as dimethylsulfoxide or N-methylpyrrolidinone, optionally in the presence of a base, such as triethylamine or diisopropylethylamine, wherein said contacting occurs under conditions suitable to provide a compound of formula (VII), wherein R² and R³ are as defined herein, and Hal is a halogen such as Br.

In certain embodiments, provided herein are salts (including pharmaceutically acceptable salts), solvates and hydrates of compounds of formula (VI), formula (VII) and formula (VIII).

In some embodiments of compounds of formula (II), R¹ is substituted or unsubstituted aryl or substituted or unsubstituted heteroaryl. For example, R¹ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, R¹ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

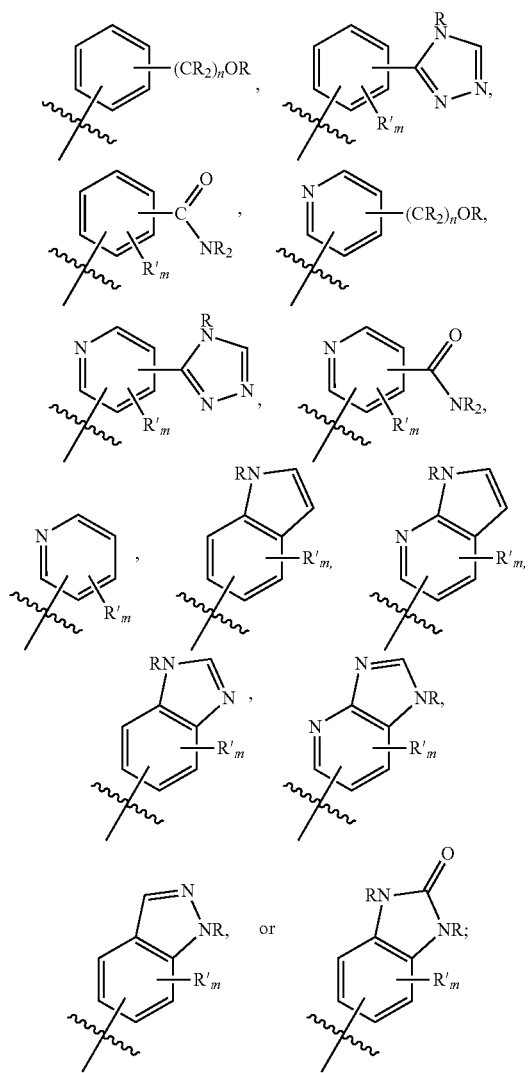

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —$NR_2$; m is 0-3; and n is 0-3. It will be understood by those skilled in the art that any of the substitutents R' may be attached to any suitable atom of any of the rings in the fused ring systems.

In some embodiments of compounds of formula (II), $R^1$ is

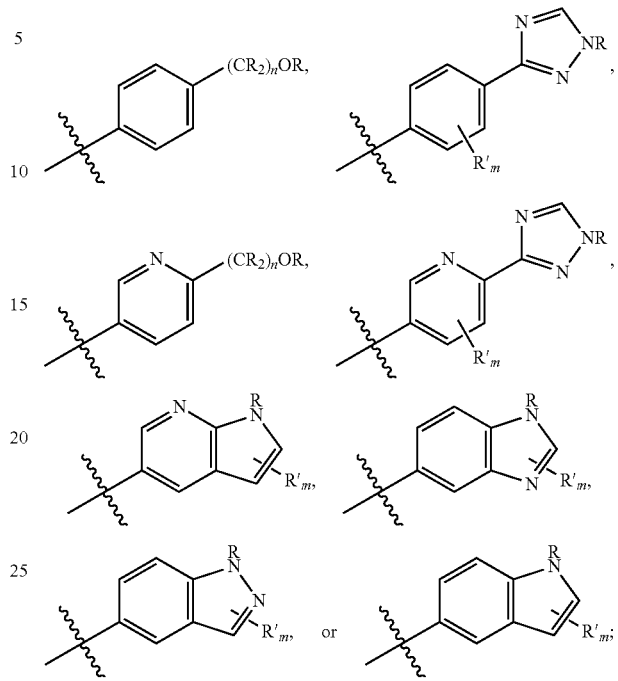

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —$NR_2$; m is 0-3; and n is 0-3.

In some embodiments of compounds of formula (II), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$ alkyl)(OR),

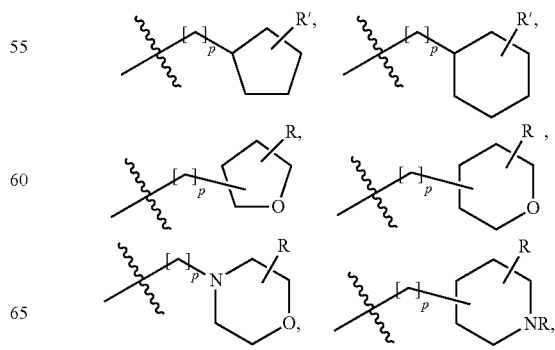

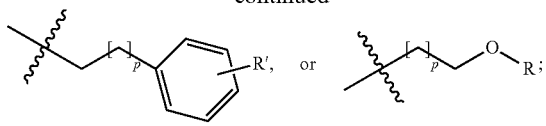

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (II), $R^2$ is H, $C_{1-4}$ alkyl, $(C_{1-4}$alkyl$)(OR)$,

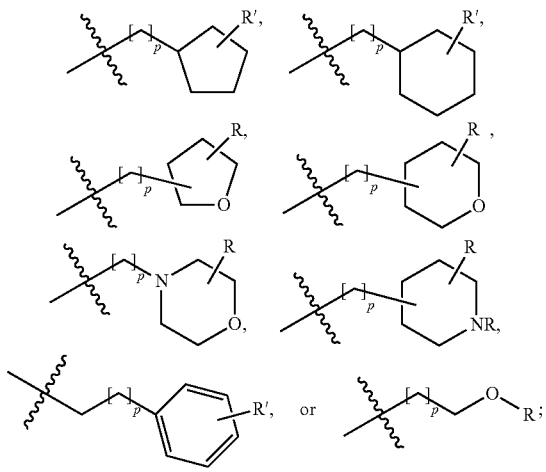

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (II), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and —$NR_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In certain embodiments, the compounds of formula (II) have an $R^1$ group set forth herein and an $R^2$ group set forth herein.

In some embodiments of compounds of formula (II), the compound at a concentration of 10 μM inhibits mTOR, DNA-PK, PI3K, or a combination thereof by at least about 50%. Compounds of formula (II) may be shown to be inhibitors of the kinases above in any suitable assay system, such as those described in the Examples herein.

In some embodiments of compounds of formula (II), the compound is 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-methoxycyclohexyl)-3,4-dihydropyrazino[2,3-b]pyrazin-2(1H)-one;

7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;

1-ethyl-7-(1H-pyrrolo[3,2-b]pyridin-5-yl)-3,4-dihydropyrazino[2,3-b]pyrazin-2(1H)-one;

7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;

7-(1H-benzo[d]imidazol-4-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;

7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;

7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;

7-(6-(1H-1,2,4-triazol-3-yl)pyridin-3-yl)-1-(2-methoxyethyl)-3,4-dihydropyrazino[2,3-b]pyrazin-2(1H)-one;

7-(6-(1H-1,2,4-triazol-3-yl)pyridin-3-yl)-1-ethyl-3,4-dihydropyrazino[2,3-b]pyrazin-2(1H)-one;

7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;

7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;

7-(1H-indol-4-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(trans-4-hydroxycyclohexyl)-3,4-dihydropyrazino[2,3-b]pyrazin-2(1H)-one;

7-(6-(1H-1,2,4-triazol-3-yl)pyridin-3-yl)-1-(trans-4-methoxycyclohexyl)-3,4-dihydropyrazino[2,3-b]pyrazin-2(1H)-one;

7-(6-(1H-1,2,4-triazol-3-yl)pyridin-3-yl)-1-isopropyl-3,4-dihydropyrazino[2,3-b]pyrazin-2(1H)-one;

7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;

7-(5-fluoro-2-methyl-4-(1H-1,2,4-triazol-3-yl)phenyl)-1-isopropyl-3,4-dihydropyrazino[2,3-b]pyrazin-2(1H)-one;

1-ethyl-7-(5-fluoro-2-methyl-4-(1H-1,2,4-triazol-3-yl)phenyl)-3,4-dihydropyrazino[2,3-b]pyrazin-2(1H)-one;

7-(2-hydroxypyridin-4-yl)-1-(2-(tetrahydro-2H-pyran-4-yl)ethyl)-3,4-dihydropyrazino[2,3-b]pyrazin-2(1H)-one;

1-isopropyl-7-(4-methyl-6-(1H-1,2,4-triazol-3-yl)pyridin-3-yl)-3,4-dihydropyrazino[2,3-b]pyrazin-2(1H)-one;

5-(8-isopropyl-7-oxo-5,6,7,8-tetrahydropyrazino[2,3-b]pyrazin-2-yl)-4-methylpicolinamide;

7-(1H-indazol-4-yl)-1-(2-(tetrahydro-2H-pyran-4-yl)ethyl)-3,4-dihydropyrazino[2,3-b]pyrazin-2(1H)-one;

7-(2-aminopyrimidin-5-yl)-1-(2-(tetrahydro-2H-pyran-4-yl)ethyl)-3,4-dihydropyrazino[2,3-b]pyrazin-2(1H)-one;

7-(2-aminopyridin-4-yl)-1-(2-(tetrahydro-2H-pyran-4-yl)ethyl)-3,4-dihydropyrazino[2,3-b]pyrazin-2(1H)-one;

7-(6-(methylamino)pyridin-3-yl)-1-(2-(tetrahydro-2H-pyran-4-yl)ethyl)-3,4-dihydropyrazino[2,3-b]pyrazin-2(1H)-one;

7-(6-hydroxypyridin-3-yl)-1-(2-(tetrahydro-2H-pyran-4-yl)ethyl)-3,4-dihydropyrazino[2,3-b]pyrazin-2(1H)-one;

7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3,4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3,4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3,4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7-oxo-8-(2-(tetrahydro-2H-pyran-4-yl)ethyl)-5,6,7,8-tetrahydropyrazino[2,3-b]pyrazin-2-yl)benzamide;

5-(8-((trans-4-methoxycyclohexyl)methyl)-7-oxo-5,6,7,8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1(2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3S)-3-methoxycyclopentyl)-3,4-dihydropyrazino[2,3-b]pyrazin-2(1H)-one;

7-(6-(2-hydroxypropan-2-yl)pyridin-3-yl)-1-((1R,3S)-3-methoxycyclopentyl)-3,4-dihydropyrazino[2,3-b]pyrazin-2(1H)-one;

7-(1H-indazol-6-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(2-morpholinoethyl)-3,4-dihydropyrazino[2,3-b]pyrazin-2(1H)-one;

1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(2-morpholinoethyl)-3,4-dihydropyrazino[2,3-b]pyrazin-2(1H)-one;

1-isopropyl-7-(2-methyl-6-(4H-1,2,4-triazol-3-yl)pyridin-3-yl)-3,4-dihydropyrazino[2,3-b]pyrazin-2(1H)-one;

7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;

1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

1-(trans-4-hydroxycyclohexyl)-7-(6-(2-hydroxypropan-2-yl)pyridin-3-yl)-3,4-dihydropyrazino[2,3-b]pyrazin-2(1H)-one;

1-(cis-4-hydroxycyclohexyl)-7-(6-(2-hydroxypropan-2-yl)pyridin-3-yl)-3,4-dihydropyrazino[2,3-b]pyrazin-2(1H)-one;

4-(7-oxo-8-(2-(tetrahydro-2H-pyran-4-yl)ethyl)-5,6,7,8-tetrahydropyrazino[2,3-b]pyrazin-2-yl)benzamide;

7-(1H-indazol-5-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;

1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

7-(1H-indol-5-yl)-1-(2-(tetrahydro-2H-pyran-4-yl)ethyl)-3,4-dihydropyrazino[2,3-b]pyrazin-2(1H)-one;

1-ethyl-7-(2-methyl-6-(4H-1,2,4-triazol-3-yl)pyridin-3-yl)-3,4-dihydropyrazino[2,3-b]pyrazin-2(1H)-one;

7-(1H-indol-6-yl)-1-(2-(tetrahydro-2H-pyran-4-yl)ethyl)-3,4-dihydropyrazino[2,3-b]pyrazin-2(1H)-one;

7-(4-(2-hydroxypropan-2-yl)phenyl)-1-(trans-4-methoxycyclohexyl)-3,4-dihydropyrazino[2,3-b]pyrazin-2(1H)-one;

7-(6-(2-hydroxypropan-2-yl)pyridin-3-yl)-1-(tetrahydro-2H-pyran-4-yl)-3,4-dihydropyrazino[2,3-b]pyrazin-2(1H)-one;

1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((cis-4-methoxycyclohexyl)methyl)-3,4-dihydropyrazino[2,3-b]pyrazin-2(1H)-one;

1-(2-methoxyethyl)-7-(4-methyl-2-(methylamino)-1H-benzo[d]imidazol-6-yl)-3,4-dihydropyrazino[2,3-b]pyrazin-2(1H)-one;

7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;

7-(2-methyl-4-(4H-1,2,4-triazol-3-yl)phenyl)-3,4-dihydropyrazino[2,3-b]pyrazin-2(1H)-one;

1-(2-methoxyethyl)-7-(4-methyl-6-(1H-1,2,4-triazol-3-yl)pyridin-3-yl)-3,4-dihydropyrazino[2,3-b]pyrazin-2(1H)-one;

1-benzyl-7-(2-methyl-4-(4H-1,2,4-triazol-3-yl)phenyl)-3,4-dihydropyrazino[2,3-b]pyrazin-2(1H)-one;

7-(3-fluoro-4-(4H-1,2,4-triazol-3-yl)phenyl)-1-(2-methoxyethyl)-3,4-dihydropyrazino[2,3-b]pyrazin-2(1H)-one;

7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;

1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(trans-4-methoxycyclohexyl)-3,4-dihydropyrazino[2,3-b]pyrazin-2(1H)-one;

7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

1-(2-methoxyethyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((trans-4-methoxycyclohexyl)methyl)-3,4-dihydropyrazino[2,3-b]pyrazin-2(1H)-one;

1-(cyclopentylmethyl)-7-(6-(2-hydroxypropan-2-yl)pyridin-3-yl)-3,4-dihydropyrazino[2,3-b]pyrazin-2(1H)-one;

7-(4-(2-hydroxypropan-2-yl)phenyl)-1-(2-methoxyethyl)-3,4-dihydropyrazino[2,3-b]pyrazin-2(1H)-one;

(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;

7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(4-(trifluoromethyl)benzyl)-3,4-dihydropyrazino[2,3-b]pyrazin-2(1H)-one;

7-(6-(2-hydroxypropan-2-yl)pyridin-3-yl)-1-(3-(trifluoromethyl)benzyl)-3,4-dihydropyrazino[2,3-b]pyrazin-2(1H)-one;

7-(6-(2-hydroxypropan-2-yl)pyridin-3-yl)-1-(3-methoxypropyl)-3,4-dihydropyrazino[2,3-b]pyrazin-2(1H)-one;

7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-methoxyethyl)-3,4-dihydropyrazino[2,3-b]pyrazin-2(1H)-one;

7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;

7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;

7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;

7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;

7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;

7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;

1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; or 1-(2-hydroxyethyl)-7-(2-methyl-6-(1H-1,2,4-triazol-3-yl)pyridin-3-yl)-3,4-dihydropyrazino[2,3-b]pyrazin-2(1H)-one.

4.3 Methods for Making Heteroaryl Compounds

The Heteroaryl Compounds are prepared as outlined in Schemes 1-9 shown below, as well as in the examples set forth in Section 5.1. It should be noted that one skilled in the art can modify the procedures set forth in the illustrative schemes and examples to arrive at the desired product.

nated using NBS or other standard brominating conditions to afford the brominated intermediate C, which is then reacted with 2-bromoacetic anhydride to afford the acylated intermediate D. The $R^2$ substituent is introduced through amine addition to D and subsequent ring closure, in the presence of an amine base (such as, for example, triethyl amine) and heating in an appropriate solvent (such as acetonitrile) to afford the desired products.

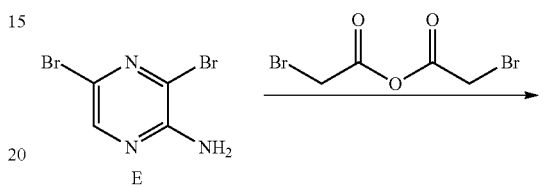

Scheme 2

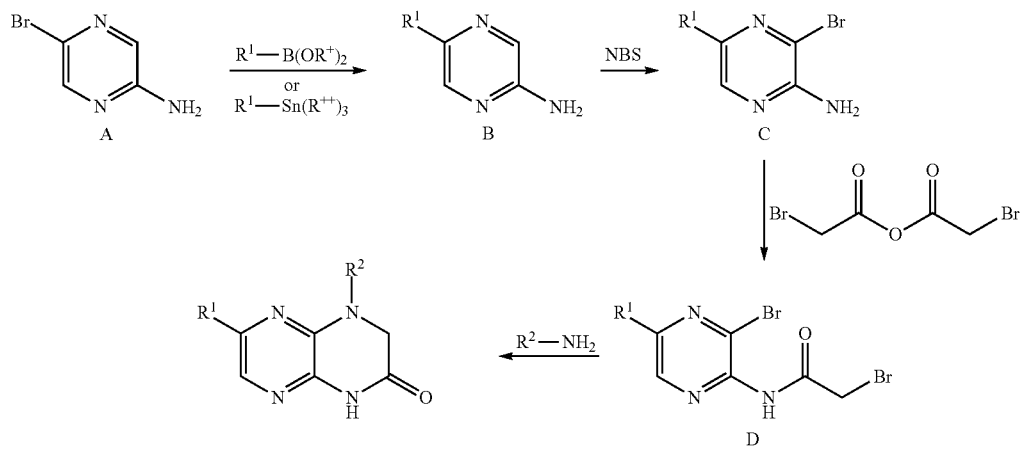

Scheme 1

Synthesis of compounds of formula (I) is shown in Scheme 1. Starting from 5-bromopyrazin-2-amine A, the $R^1$ group can be introduced using the appropriate boronic acid or borate ester ($R^+$ is H, or together with the boron atom and the atoms to which they are attached, form a cyclic boronate), palladium catalyst (such as, for example, dichloro[1,1'-bis(diphenylphosphino)ferrocene]palladium(II)dichloromethane), solvent (such as dimethylformamide) and base (such as sodium carbonate) through a Suzuki coupling, or alternately with the appropriate stannane ($R^{++}$ is $C_{1-4}$ alkyl), palladium catalyst (such as dichloro[1,1'-bis(diphenylphosphino)ferrocene]palladium(II)dichloromethane or palladium(dba)$_2$/tri-o-tolylphosphine) and solvent (such as dimethylformamide with or without the addition of a base such as triethylamine) using Stille coupling methodology. Typical reaction conditions and reagents for Suzuki and Stille reactions can be found herein (see also Rossi, et al, *Synthesis* 15:2419-2440 (2004), Buchwald et al. *Accounts of Chemical Research*, 41: 1461-1473 (2008), Fu. *Accounts of Chemical Research*, 41: 1555-1564 (2008), and Echavarren et al. *Angew. Chem. Int. Ed.*, 43: 4704-4734 (2004) and references therein). The resulting $R^1$ amino pyrazine B can be bromi- -continued

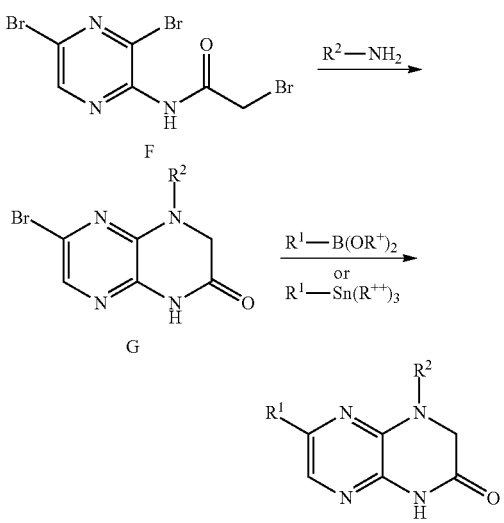

Alternatively as shown in Scheme 2, 3,5-dibromopyrazin-2-amine E, is treated with 2-bromoacetic anhydride as above to provide intermediate F. As described above, the $R^2$ substituent is introduced through amine addition to F and subsequent ring closure to afford intermediate G. The $R^1$ group may then be introduced using the methods described above, namely by reaction with the appropriate boronic acid or borate ester, in the presence of a palladium catalyst and base through a Suzuki coupling, or alternately with the appropriate stannane, in the presence of a palladium catalyst using Stille coupling methodology as described above, to afford the desired products.

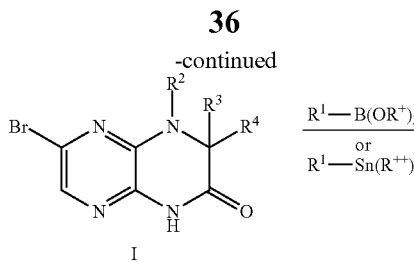

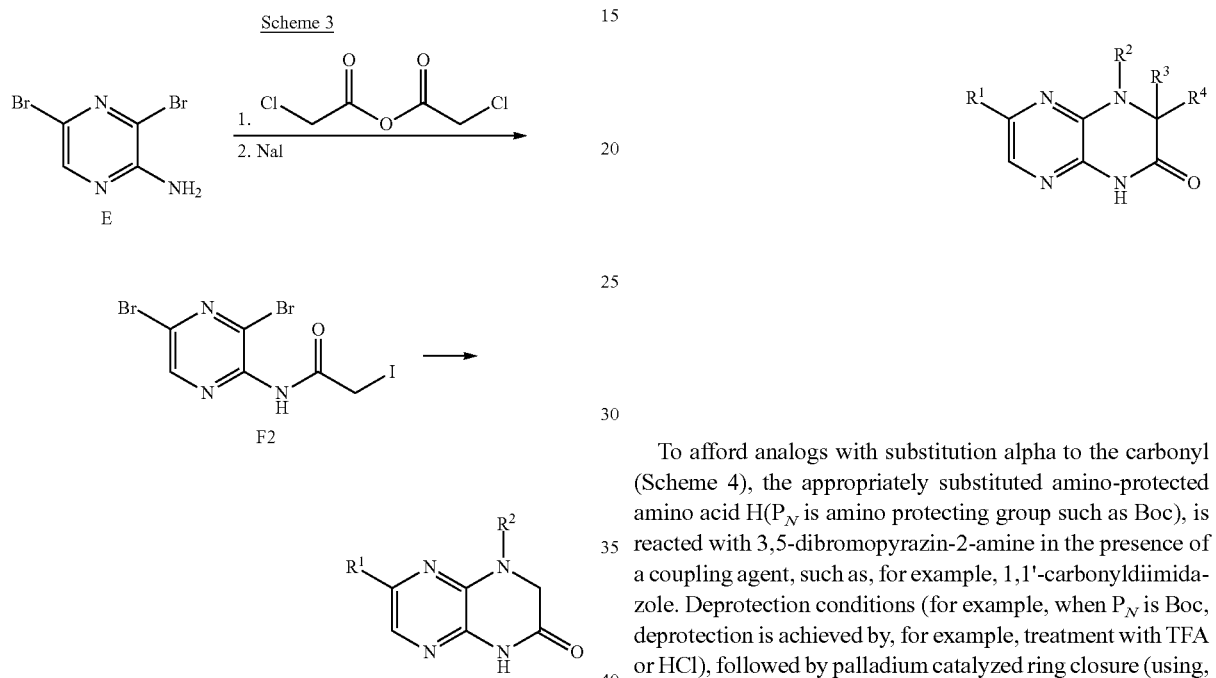

In an another approach (Scheme 3), 3,5-dibromopyrazin-2-amine E, is treated with 2-chloroacetic anhydride followed by sodium iodide to provide the iodo intermediate F2. Intermediate F2 is converted to the desired products following the procedures outlined in Scheme 2 for F.

To afford analogs with substitution alpha to the carbonyl (Scheme 4), the appropriately substituted amino-protected amino acid H($P_N$ is amino protecting group such as Boc), is reacted with 3,5-dibromopyrazin-2-amine in the presence of a coupling agent, such as, for example, 1,1'-carbonyldiimidazole. Deprotection conditions (for example, when $P_N$ is Boc, deprotection is achieved by, for example, treatment with TFA or HCl), followed by palladium catalyzed ring closure (using, for example, sodium bicarbonate, palladium(II) acetate and 4,5-bis(diphenylphosphino)-9,9-dimethylxanthene) to afford intermediate I. As before, the $R^1$ group may be introduced using the appropriate boronic acid or borate ester, palladium catalyst, solvent and base through a Suzuki coupling, or alternately with the appropriate stannane, palladium catalyst and solvent using Stille coupling methodology (described above) to afford the desired products. This method may also be used to afford analogs where $R^2$ is hydrogen. Additionally, this route may be used to afford compounds wherein $R^3$ and $R^4$, together with the atom to which they are both attached, form a spiro-cyclic ring, through the use of appropriate starting amino acids.

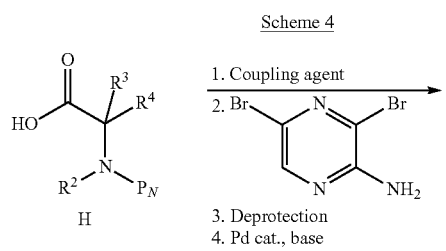

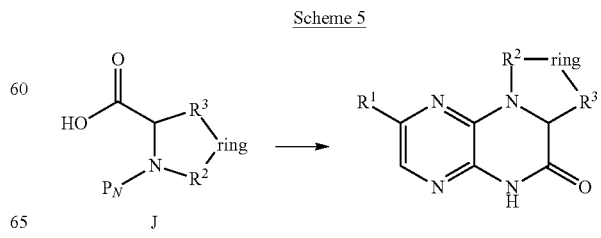

Analogs wherein $R^2$ and $R^3$ together with the atoms to which they are attached form a ring (see Scheme 5) may be obtained similarly to the chemistry shown in Scheme 4, beginning with the appropriate cyclic amino acid J.

Compounds of formula (II) may be obtained as shown in Scheme 7. Reductive amination of 3,5-dibromopyrazin-2-amine E with ethyl 2-oxoacetate (in the presence of, for example, sodium borohydride as a reducing agent) affords

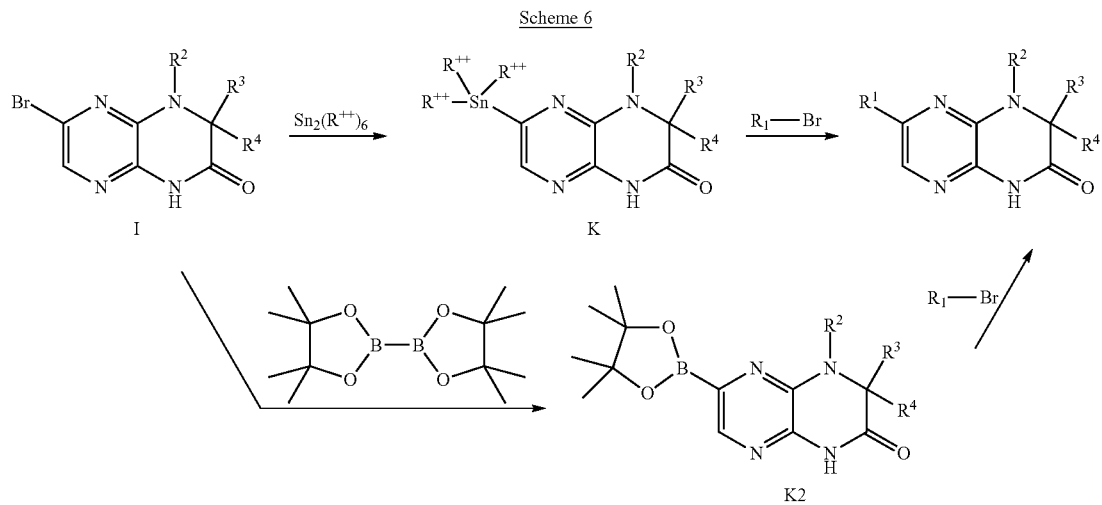

To obtain the desired products, the reactivity of the coupling partners may be reversed. For example, as shown in Scheme 6, intermediate I may be converted to the corresponding stannane K, through reaction with, for example, hexamethylditin ($R^{++}$ is methyl) in the presence of a palladium catalyst (such as tetrakis(triphenylphosphine)-palladium) and the $R^1$ group may be introduced using an appropriate leaving group, for example halogen (such as bromide) or triflate, and solvent using Stille coupling methodology as described above to afford the desired products. Alternatively, intermediate I may be converted to the corresponding boronate ester K2, by reaction with 4,4,4',4',5,5,5',5'-octamethyl-2,2'-bi(1,3,2-dioxaborolane) in the presence of a palladium catalyst (such as 1,1'-bis(diphenylphosphino)ferrocene]palladium(II)dichloromethane) and a base (such as potassium acetate) in a solvent such as dioxane. The $R^1$ group may be introduced using an appropriate leaving group, for example halogen (such as bromide) or triflate, palladium catalyst and solvent using Suzuki coupling methodology as described above, to afford the desired products.

intermediate L. Alternatively, 3,5-dibromopyrazin-2-amine E may be converted to intermediate L by reaction with ethyl 2-chloroacetate under basic conditions (using for example, $Cs_2CO_3$). The $R^2$ substituent is introduced through amine addition to L, in the presence of an amine base, such as diisopropylethylamine, and heating in an appropriate solvent (such as DMSO) and subsequent acid catalyzed ring closure (using, for example, acetic acid) to afford intermediate M. The ring closure of the amine addition product L may also proceed under basic catalyzed conditions, such as treatment with potassium t-butoxide in an appropriate solvent. Alternatively, the ethyl ester moiety can be hydrolyzed (for example by base treatment) prior to reaction with $R^2$—$NH_2$ in water, followed by acid catalyzed ring closure. As before, the $R^1$ group may be introduced using the appropriate boronic acid or borate ester, palladium catalyst, solvent and base through a Suzuki coupling, or alternately with the appropriate stannane, palladium catalyst and solvent using Stille coupling methodology (described above) to afford the desired products.

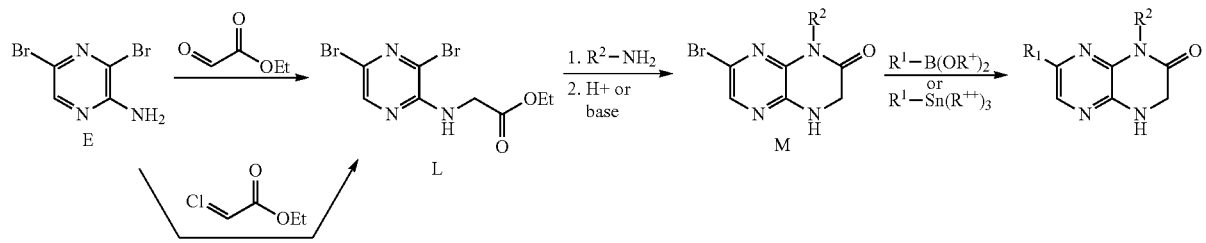

Scheme 8

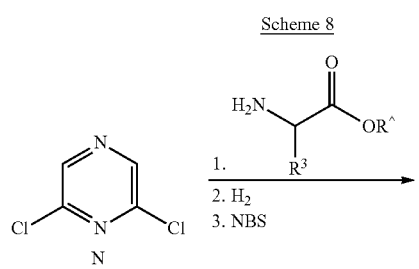

An alternative approach (Scheme 8) begins with reaction of 2,6-dichloropyrazine N with the appropriate amino ester (R^ is $C_{1-3}$ alkyl), followed by reductive dehalogenation with hydrogen and a palladium catalyst such as palladium hydroxide, a base such as potassium carbonate, in a solvent such as ethanol, and subsequent bromination by reaction with a brominating agent such as NBS to yield intermediate O. As above, the $R^2$ substituent is introduced through amine addition to O and subsequent acid catalyzed ring closure to afford intermediate P. The $R^1$ group may be introduced using the appropriate boronic acid or borate ester, palladium catalyst, solvent and base through a Suzuki coupling, or alternately with the appropriate stannane, palladium catalyst and solvent using Stille coupling methodology to afford the desired products (described above). This route also allows for the synthesis of analogs with $R^3$ substitution alpha to the carbonyl group.

Scheme 9

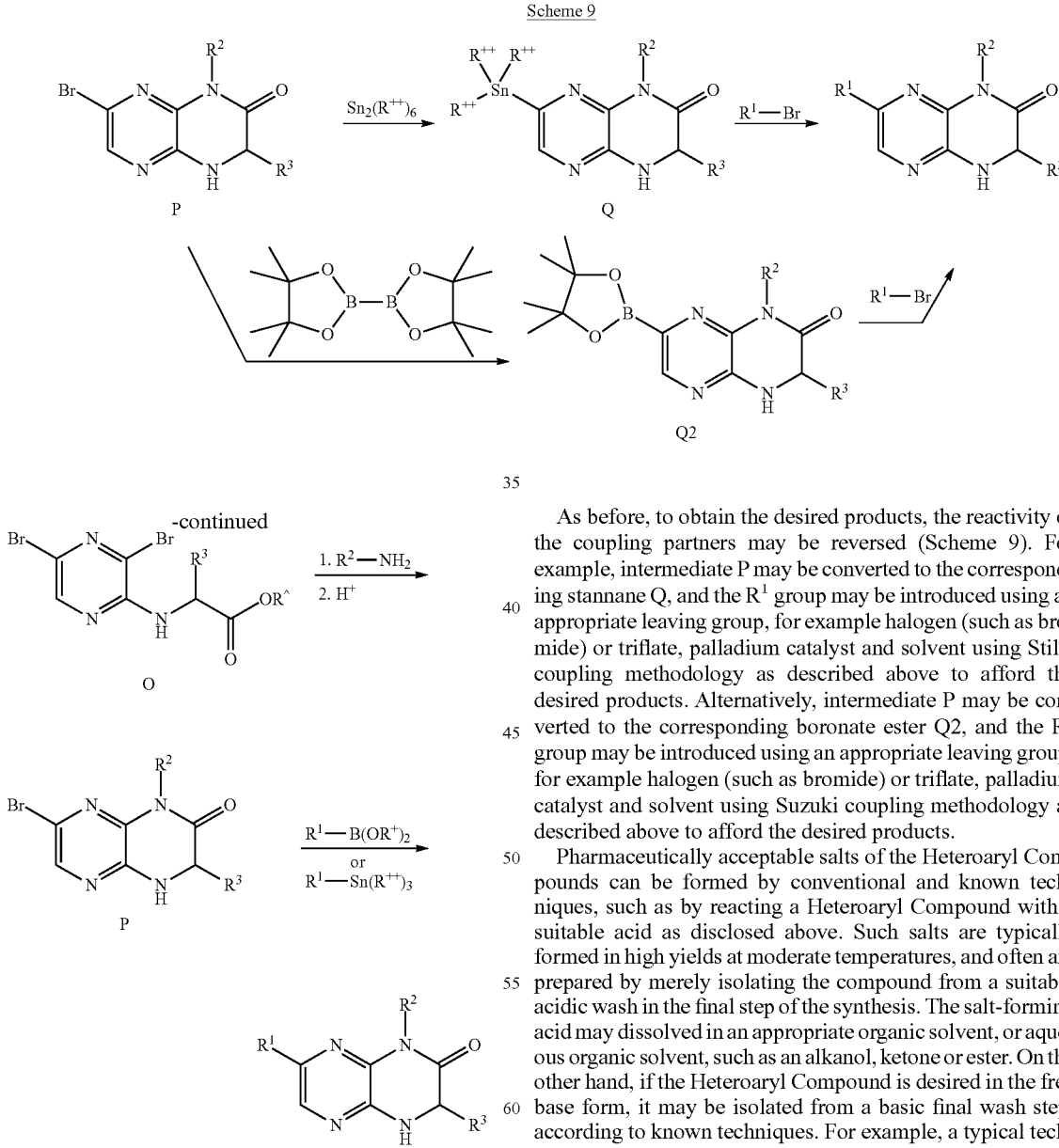

As before, to obtain the desired products, the reactivity of the coupling partners may be reversed (Scheme 9). For example, intermediate P may be converted to the corresponding stannane Q, and the $R^1$ group may be introduced using an appropriate leaving group, for example halogen (such as bromide) or triflate, palladium catalyst and solvent using Stille coupling methodology as described above to afford the desired products. Alternatively, intermediate P may be converted to the corresponding boronate ester Q2, and the $R^1$ group may be introduced using an appropriate leaving group, for example halogen (such as bromide) or triflate, palladium catalyst and solvent using Suzuki coupling methodology as described above to afford the desired products.

Pharmaceutically acceptable salts of the Heteroaryl Compounds can be formed by conventional and known techniques, such as by reacting a Heteroaryl Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Heteroaryl Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

Chemical intermediates useful in the methods provided herein include:

(i) compounds having formula (III):

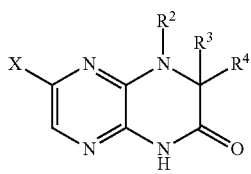
(III)

or a salt, tautomer or stereoisomer thereof, wherein:
X is halogen, $B(OR^+)_2$ or $Sn(R^{++})_3$;
each $R^+$ is independently hydrogen or substituted or unsubstituted $C_{1-3}$ alkyl, or each $R^+$, together with the boron atom and the atoms to which they are attached, form a cyclic boronate;
each $R^{++}$ is independently $C_{1-4}$ alkyl;
$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl; and
$R^3$ and $R^4$ are each independently H, substituted or unsubstituted $C_{1-8}$ alkyl, substituted or unsubstituted aryl, substituted or unsubstituted cycloalkyl, substituted or unsubstituted heterocyclyl, substituted or unsubstituted heterocyclylalkyl, substituted or unsubstituted aralkyl, substituted or unsubstituted cycloalkylalkyl, or $R^3$ and $R^4$, together with the atom to which they are attached, form a substituted or unsubstituted cycloalkyl or substituted or unsubstituted heterocyclyl;
or $R^2$ and one of $R^3$ and $R^4$, together with the atoms to which they are attached, form a substituted or unsubstituted heterocyclyl;
(ii) compounds having formula (IV):

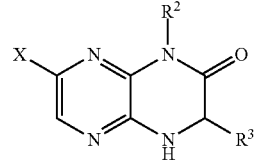
(IV)

or a salt, tautomer or stereoisomer thereof, wherein:
each Hal is independently a halogen; and
$Hal^2$ is Br or I;
(iii) compounds having formula (V):

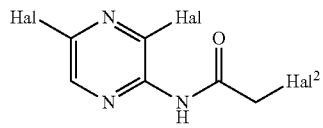
(V)

or a salt, tautomer or stereoisomer thereof, wherein:
$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;
$R^3$ and $R^4$ are each independently H, substituted or unsubstituted $C_{1-8}$ alkyl, substituted or unsubstituted aryl, substituted or unsubstituted cycloalkyl, substituted or unsubstituted heterocyclyl, substituted or unsubstituted heterocyclylalkyl, substituted or unsubstituted aralkyl, substituted or unsubstituted cycloalkylalkyl, or $R^3$ and $R^4$, together with the atom to which they are attached, form a substituted or unsubstituted cycloalkyl or substituted or unsubstituted heterocyclyl;
or $R^2$ and one of $R^3$ and $R^4$, together with the atoms to which they are attached, form a substituted or unsubstituted heterocyclyl; and
each Hal is independently a halogen;
(iv) compounds having formula (VI):

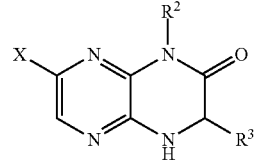
(VI)

or a salt, tautomer or stereoisomer thereof, wherein:
X is halogen, $B(OR^+)_2$ or $Sn(R^{++})_3$;
each $R^+$ is independently hydrogen or substituted or unsubstituted $C_{1-3}$ alkyl, or each $R^+$, together with the boron atom and the atoms to which they are attached, form a cyclic boronate;
each $R^{++}$ is independently $C_{1-3}$ alkyl;
$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl; and
$R^3$ is H, or a substituted or unsubstituted $C_{1-8}$ alkyl;
(v) compounds having formula (VII):

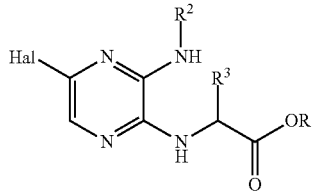
(VII)

or a salt, tautomer or stereoisomer thereof, wherein:
Hal is a halogen;
R is H or $C_{1-4}$ alkyl, or the alkali metal salt of the carboxylate;
$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl; and
$R^3$ is H, or a substituted or unsubstituted $C_{1-8}$ alkyl; and
(vi) compounds having formula (VIII):

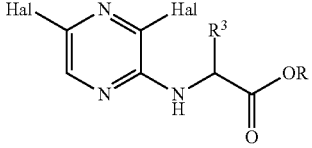
(VIII)

or a salt, tautomer or stereoisomer thereof, wherein:
each Hal is independently a halogen;
R is H or $C_{1-4}$ alkyl, or the alkali metal salt of the carboxylate; and
$R^3$ is H, or a substituted or unsubstituted $C_{1-8}$ alkyl.

4.4 Methods of Use

Heteroaryl Compounds described herein have utility as pharmaceuticals to treat or prevent disease in animals or humans. Further, Heteroaryl Compounds described herein are active against kinases (e.g., protein kinases), including those involved in cancer, inflammatory conditions, immunological conditions, neurodegenerative diseases, diabetes, obesity, neurological disorders, age-related diseases, and cardiovascular conditions. Without being limited by theory, it is thought the Heteroaryl Compounds are effective for treating and preventing said diseases and conditions due to their ability to modulate (e.g., inhibit) kinases which are involved in the etiology of these diseases and conditions. Accordingly, provided herein are many uses of the Heteroaryl Compounds, including the treatment or prevention of those diseases set forth below. The methods provided herein comprise the administration of an effective amount of one or more Heteroaryl Compounds to a patient in need thereof. In some embodiments, the methods additionally comprise administration of a second active agent as described herein.

Representative immunological conditions that Heteroaryl Compounds are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Graves disease, encephalomyelitis, Type II diabetes, dermatomyositis, and transplant rejection (e.g. in the treatment of recipients of e.g. heart, lung, combined heart-lung, liver, kidney, pancreatic, skin or corneal transplants; or graft-versus-host disease, such as following bone marrow transplantation).

Representative inflammatory conditions that Heteroaryl Compounds are useful for treating or preventing include, but are not limited to, psoriasis, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, and obesity.

Representative cardiovascular diseases that Heteroaryl Compounds are useful for treating or preventing include, but are not limited to, restenosis, Wolf-Parkinson-White Syndrome, stroke, myocardial infarction or ischemic damage to the heart, lung, gut, kidney, liver, pancreas, spleen or brain.

Representative neurodegenerative diseases that Heteroaryl Compounds are useful for treating or preventing include, but are not limited to, Huntington's disease, Alzheimer's disease, Parkinson's disease, dementias caused by tau mutations, spinocerebellar ataxia type 3, motor neuron disease caused by SOD1 mutations, neuronal ceroid lipofucinoses/Batten disease (pediatric neurodegeneration) and HIV-associated encephalitis.

Representative age-related diseases that Heteroaryl Compounds are useful for treating or preventing include but are not limited to cancer, obesity, type II diabetes mellitus, autoimmune disease, cardiovascular diseases and neuronal degeneration.

In another embodiment, provided herein are methods for the treatment or prevention of fibrotic diseases and disorders. In a particular embodiment, provided herein are methods for the treatment or prevention of scleroderma, idiopathic pulmonary fibrosis, renal fibrosis, cystic fibrosis, myelofibrosis, hepatic fibrosis, steatofibrosis and steatohepatitis.

Representative cancers that Heteroaryl Compounds are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. Heteroaryl Compounds are also useful for treating or preventing solid tumors and bloodborne tumors.

Particular cancers within the scope of the methods provided herein include those associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas.

In a particular embodiment, provided herein are methods for the treatment or prevention of a disease or disorder associated with activation of mTOR signaling, including, but not limited to, tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), LKB1, VHL (von Hippel-Lindau disease) and PKD1 (polycystin-1). Without being limited by theory, it is thought that genetic defects associated with these proteins results in hyperactivation of the mTOR/PI3K/Akt pathway. Some particular diseases which are treatable or preventable through inhibition of the mTOR/PI3K/Akt pathway include, but are not limited to, Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, Proteus syndrome, and polycystic kidney disease.

In a particular embodiment, provided herein are methods for the treatment or prevention of a disease or disorder associated with mTOR, PI3K, Akt, and/or DNA-PK signaling. Particular diseases which are treatable or preventable by inhibiting mTOR, PI3K, Akt and/or DNA-PK signaling, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases (including retinitis pigmentosa), solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

Also provided herein are methods for inhibiting a kinase in a cell expressing said kinase, comprising contacting the cell with an effective amount of a Heteroaryl Compound as described herein. In one embodiment the kinase is mTOR, DNA-PK, or PI3K or a combination thereof. In some embodiments, the cell is in a patient.

Also provided herein are methods for treating or preventing a condition treatable or preventable by inhibition of a kinase pathway, for example, the mTOR/PI3K/Akt and/or DNA-PK pathway, comprising administering to a patient in need thereof an effective amount of a Heteroaryl Compound as described herein. In some embodiments, the conditions treatable or preventable by inhibition of the mTOR/PI3K/Akt pathway include solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; sarcomas; tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), and LKB1, VHL (von Hippel-Lindau disease) and PKD1 (polycystin-1); Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, Proteus syndrome, and polycystic kidney disease; rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Hunting-ton's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases, including retinitis pigmentosa, solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

4.5 Pharmaceutical Compositions and Routes of Administration

Heteroaryl Compounds made by the processes provided herein are useful for the preparation of pharmaceutical compositions, comprising an effective amount of a Heteroaryl Compound and a pharmaceutically acceptable carrier or vehicle. In some embodiments, the pharmaceutical composition described herein are suitable for oral, parenteral, mucosal, transdermal or topical administration.

5. EXAMPLES

Chem-4D Draw (ChemInnovation Software, Inc., San Diego, Calif.) or ChemDraw Ultra (Cambridgesoft, Cambridge, Mass.) was used to generate names for chemical structures.

The following abbreviations were used in descriptions and examples:
AmPhos: p-dimethylamino phenylditbutylphosphine
Boc: tert-Butoxycarbonyl
dba: dibenzylidene acetone
DIPEA: N,N-diisopropylethylamine
DMSO: Dimethylsulfoxide
ESI: Electronspray ionization
HPLC: High performance liquid chromatography
mp: Melting point
MS: Mass spectrometry
NBS: N-Bromosuccinimide
NMR: Nuclear magnetic resonance
NMP: N-methylpyrrolidinone
TFA: Trifluoroacetic acid
TLC: Thin layer chromatography
MTBE: methyl tert-butyl ether The following Examples are presented by way of illustration, not limitation.

5.1 Synthetic Examples

Example 1

7-(2-Amino-4-methyl-1H-benzo[d]imidazol-6-yl)-1-((tetrahydro-2H-pyran-4-yl)Methyl)-3,4-dihydropyrazino[2,3-b]pyrazin-2(1H)-one

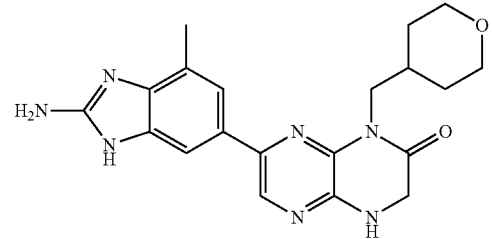 [SMILES: Cc1cc(-c2cnc3c(n2)N(CC2CCOCC2)C(=O)CN3)cc2[nH]c(N)nc12]

A. Ethyl 2-(6-chloropyrazin-2-ylamino)acetate. To 2,6-dichloropyrazine (50 g, 336 mmol) and ethyl 2-aminoacetate (34.6 g, 336 mmol) was added triethylamine (140 mL, 1007 mmol) and acetonitrile (350 mL). The reaction was heated at 80° C. for 3 d. Precipitated triethylamine salts were removed by filtration and washed with ethyl acetate and hexane (1:1) multiple times. The filtrate and wash solvent were combined and concentrated. The resulting white-yellow precipitate was filtered and washed with 20% ethyl acetate in hexane to afford an off-white solid. The filtrate was subjected to the same process to give an additional batch of off-yellow solid. The batches were combined to afford the title compound (35.5 g, 164 mmol, 49% yield). MS (ESI) m/z 216.1 [M+1]$^+$.

B. Ethyl 2-(pyrazin-2-ylamino)acetate. Ethyl 2-(6-chloropyrazin-2-ylamino)acetate (23.6 g, 109 mmol) was dissolved in non-denatured ethanol (250 mL) and potassium carbonate (15.13 g, 109 mmol) was added. The reaction was put under nitrogen and palladium hydroxide (3.84 g, 5.47 mmol) was added. The reaction was stirred under an atmosphere of hydrogen for 18 h. Additional palladium hydroxide (3.84 g, 5.47 mmol) was added and the reaction was charged with additional hydrogen and allowed to stir overnight. The reaction was filtered through Celite and the solvent was removed under reduced pressure to afford the title compound (15.13 g, 84 mmol, 76% yield). MS (ESI) m/z 182.3 [M+1]$^+$.

C. Ethyl 2-(3,5-dibromopyrazin-2-ylamino)acetate. Ethyl 2-(pyrazin-2-ylamino)acetate (7.6 g, 41.9 mmol) was dissolved in dimethylsulfoxide (80 mL) and water (4.00 mL) and cooled to 0° C. N-Bromosuccinimide (18.66 g, 105 mmol) was added slowly over 15 min and the reaction was allowed to warm to rt and stir for 48 h. An additional 1.5 equiv N-bromosuccinimide was added and allowed to stir overnight. The reaction mixture was poured into ice water (200 mL) and extracted with ethyl acetate (150 mL). The aqueous layer was neutralized with sodium carbonate slowly, until pH~7 and extracted with ethyl acetate (3×150 mL). The organic layers were pooled, washed with brine, dried over magnesium sulfate, filtered and concentrated under reduced pressure. The residue was triturated with 25-33% ethyl acetate in hexane and the resulting precipitate was filtered to give a yellow solid. The remaining brown residue was purified using Biotage silica gel chromatography (0-60% ethyl acetate in hexane) to give another batch of off-yellow solid. The two batches were combined to afford 24 g of the title compound (24 g, 71 mmol, 75% yield). MS (ESI) m/z 338.1 [M]$^+$, 340.1 [M+2]$^+$, 342.1 [M+4]$^+$.

D. Ethyl 2-(5-bromo-3-((tetrahydro-2H-pyran-4-yl)methylamino)pyrazin-2-ylamino)acetate. Ethyl 2-(3,5-dibromopyrazin-2-ylamino)acetate (2.00 g, 5.90 mmol), (tetrahydro-2H-pyran-4-yl)methanamine (0.713 g, 6.19 mmol), N,N-diisopropylethylamine (3.08 mL, 17.70 mmol) and dimethylsulfoxide (4 mL) were combined in a microwave vial with a stirbar and heated in a Biotage Emrys Optimizer microwave reactor at 150° C. for 1 h. The resulting mixture was transferred to a round bottom flask with methanol. The methanol and N,N-diisopropylethylamine were removed under reduced pressure and the residue purified using Biotage flash chromatography (5-100% ethyl acetate in hexane). Fractions containing the desired product were combined in a reparatory funnel and washed twice with water and once with brine. The organics were dried over magnesium sulfate, filtered and concentrated under reduced pressure. The residue was dried under high vacuum at 50° C. to give impure desired product (1.578 g) as an amber waxy solid which was taken on to the next step without further purification. MS (ESI) m/z 373.4 [M]$^+$, 375.4 [M+2]$^+$.

E. 7-Bromo-1-((tetrahydro-2H-pyran-4-yl)methyl)-3,4-dihydropyrazino[2,3-b]pyrazin-2(1H)-one. A stirred solution of ethyl 2-(5-bromo-3-((tetrahydro-2H-pyran-4-yl)methylamino)pyrazin-2-ylamino)acetate (1.474 g, 3.95 mmol) in acetic acid (13 mL) in a sealed vessel was heated at 120° C. in an oil bath for 2 h. The acetic acid was removed under reduced pressure. The residue was partitioned between ethyl acetate and saturated aqueous sodium bicarbonate, shaken and the layers separated. The water layer was extracted twice with ethyl acetate. The combined organics were dried over magnesium sulfate, filtered and concentrated under reduced pressure. The residue was taken up in dichloromethane and hexane and the resulting solids collected by vacuum filtration. The solids were washed with hexane and dried under vacuum to give the desired product (0.879 g, 2.688 mmol, 68% yield) as a purple solid. MS (ESI) m/z 327.1 [M]$^+$, 329.0 [M+2]$^+$.

F. 2-Methyl-6-nitro-4-(4,4,5,5-tetramethyl-1,3,2-dioxaborolan-2-yl)aniline. 4-Bromo-2-methyl-6-nitroaniline (5 g, 21.64 mmol), bis(pinacolato)diboron (5.50 g, 21.64 mmol), potassium acetate (6.37 g, 64.9 mmol) and N,N-dimethylformamide (100 mL) were combined and degassed under vacuum. Palladium acetate (0.243 g, 1.082 mmol) was added and the system was degassed again. The reaction was heated to 90° C. for 2 h. The reaction was extracted with water and dichloromethane. The organic layer was dried over anhydrous magnesium sulfate, filtered and concentrated. The residue was purified by silica gel column chromatography (0-30% ethyl acetate in hexanes) to give a yellow solid (5.3 g, 19.0 mmol, 88% yield). MS (ESI) m/z 279.0 [M+1]$^+$.

G. 3-Methyl-5-(4,4,5,5-tetramethyl-1,3,2-dioxaborolan-2-yl)benzene-1,2-diamine. A solution of 2-Methyl-6-nitro-4-(4,4,5,5-tetramethyl-1,3,2-dioxaborolan-2-yl)aniline (5.3 g, 19.06 mmol) in methanol (50 mL) was purged with nitrogen gas. Palladium on carbon (10% by wt, 50 mg) was added and the reaction mixture was stirred under a hydrogen balloon for 16 h. The reaction was filtered through Celite and the filter cake was rinsed with methanol. The filtrate was concentrated and the resulting material was purified by silica gel column chromatography (0-100% ethyl acetate in hexanes) to give a dark oil. The oil was triturated with 10% ether in hexanes to give a tan colored solid (4.2 g, 16.9 mmol, 89% yield). MS (ESI) m/z 248.9 [M+1]$^+$.

H. 7-(3,4-Diamino-5-methylphenyl)-1-((tetrahydro-2H-pyran-4-yl)methyl)-3,4-dihydropyrazino[2,3-b]pyrazin-2(1H)-one. 3-Methyl-5-(4,4,5,5-tetramethyl-1,3,2-dioxaborolan-2-yl)benzene-1,2-diamine (0.523 g, 2.109 mmol), 7-bromo-1-((tetrahydro-2H-pyran-4-yl)methyl)-3,4-dihydropyrazino[2,3-b]pyrazin-2(1H)-one (0.600 g, 1.834 mmol), [1,1'-bis(diphenylphosphino)-ferrocene]dichloropalladium(II), complex with dichloromethane (1:1) (0.150 g, 0.183 mmol), sodium carbonate (1 M in water, 5.50 mmol), 1,4-dioxane (4.1 mL) and isopropanol (1.4 mL) were combined in a sealable vessel with a stirbar. The system was purged with nitrogen. The resulting mixture was sealed, stirred vigorously and heated at 100° C. for 3.5 h. The resulting mixture was diluted with 20% methanol in dichloromethane and all volatiles removed under reduced pressure. The residue was taken up in 20% methanol in dichloromethane and concentrated under reduced pressure with silica gel. The residue was purified using flash chromatography (1-10% methanol in dichloromethane) to give the desired product (0.669 g, 1.818 mmol, 99% yield) as a brown solid. MS (ESI) m/z 369.1 [M+1]$^+$.

I. 7-(2-Amino-4-methyl-1H-benzo[d]imidazol-6-yl)-1-((tetrahydro-2H-pyran-4-yl)methyl)-3,4-dihydropyrazino[2,3-b]pyrazin-2(1H)-one. Cyanogen bromide (0.059 g, 0.556 mmol) in N,N-dimethylformamide (0.5 mL) was added to a stirred solution of 7-(3,4-diamino-5-methylphenyl)-1-((tetrahydro-2H-pyran-4-yl)methyl)-3,4-dihydropyrazino[2,3-b]pyrazin-2(1H)-one (0.195 g, 0.529 mmol) in N,N-dimethylformamide (3 mL) at 0° C. The resulting dark brown mixture was capped and stirred at room temperature for 16 h. The resulting mixture was diluted with methanol, filtered and purified using reverse-phase preparatory HPLC (5-50% acetonitrile+0.1% TFA in water+0.1% TFA, over 30 min). Fractions containing the desired product were combined and most of the solvent removed under reduced pressure. The residue was loaded onto a Strata X-C ion exchange column from Phenomenex. The column was washed successively with water, acetonitrile, methanol and 5% ammonium hydroxide in methanol. The product eluted with the 5% ammonium hydroxide in methanol eluent and was concentrated under reduced pressure and dried under high vacuum at 50° C. to give the desired product (0.130 g, 0.331 mmol, 62% yield) as an orange solid. $^1$H NMR (400 MHz, D$_2$O and DMSO-d$_6$) δ (ppm) 8.13 (s, 1H), 7.56 (s, 1H), 7.36 (s, 1H), 4.18 (s, 2H), 4.03 (d, J=6.64 Hz, 2H), 3.84-3.90 (m, 2H), 3.24 (t, J=11.32 Hz, 2H), 2.40 (s, 3H), 2.04-2.19 (m, 1H), 1.59 (d, J=12.10 Hz, 2H), 1.25-1.41 (m, 2H); MS (ESI) m/z 394.2 [M+1]$^+$.

Example 2

3,3-Dimethyl-6-(2-methyl-4-(4H-1,2,4-triazol-3-yl) phenyl)-4-(2-(tetrahydro-2H-pyran-4-yl)ethyl)-3,4-dihydropyrazino[2,3-b]pyrazin-2(1H)-one

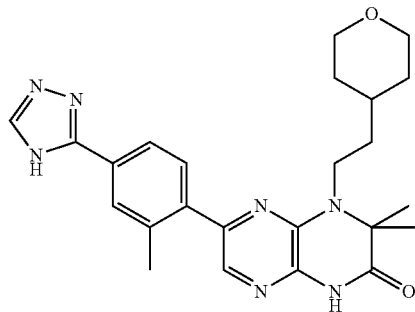 [SMILES: Cc1cc(-c2nnc[nH]2)ccc1-c1cnc2c(n1)N(CCC1CCOCC1)C(C)(C)C(=O)N2]

A. 3-(4-Bromo-3-methylphenyl)-4H-1,2,4-triazole. 4-Bromo-3-methylbenzonitrile (10.0 g, 51.0 mmol) was dissolved in ethanol (200 mL) with stirring and cooled to 0° C. under nitrogen. Hydrogen chloride gas was bubbled into the reaction mixture for 20 min. The resulting reaction mixture was capped and stirred while slowly warming to room temperature for 5.5 h. Solvent was removed under reduced pressure and the residue dried under vacuum to give 13.86 g of an off-white solid. The off-white solid, formic hydrazide (4.48 g, 74.6 mmol), triethylamine (28.0 mL, 199 mmol) and ethanol (90 mL) were combined in a sealed tube and heated, with stirring, at 90° C. for 6.5 h. All the solvent was removed under reduced pressure and the resulting residue partitioned between ethyl acetate and water. The layers were separated and the organics washed with brine, dried over magnesium sulfate, filtered and concentrated under reduced pressure. The residue was dissolved in hot ethyl acetate (13 mL), capped and let stand at room temperature overnight. The solvent was decanted away from the solids at the bottom of the flask. The solids were washed with ethyl acetate and diethyl ether and dried under vacuum at 45° C. to give the desired product (7.47 g, 31.4 mmol, 63% yield) as a light yellow solid. MS (ESI) m/z 238.2 [M]$^+$, 240.3 [M+2]$^+$.

B. 3-(4-Bromo-3-methylphenyl)-4-(tetrahydro-2H-pyran-2-yl)-4H-1,2,4-triazole. 3-(4-Bromo-3-methylphenyl)-4H-1,2,4-triazole (2.00 g, 8.40 mmol) was dissolved in tetrahydrofuran (10 mL) at room temperature with stirring under nitrogen. 3,4-Dihydro-2H-pyran (3.80 mL, 42.0 mmol) and methanesulfonic acid (0.027 mL, 0.42 mmol) were added and the resulting mixture heated at 50° C. under a reflux condenser under nitrogen for 20 h. The resulting mixture was cooled to room temperature, diluted with ethyl acetate and washed with saturated aqueous sodium bicarbonate and brine. The organics were dried over magnesium sulfate, filtered and concentrated under reduced pressure. Flash chromatography (10-30-50% ethyl acetate in hexanes) gave the desired product (2.64 g, 8.22 mmol, 98% yield) as a yellow oil. MS (ESI) m/z 322 [M]$^+$, 324 [M+2]$^+$.

C. 3-(3-Methyl-4-(4,4,5,5-tetramethyl-1,3,2-dioxaborolan-2-yl)phenyl)-4-(tetrahydro-2H-pyran-2-yl)-4H-1,2,4-triazole. 3-(4-Bromo-3-methylphenyl)-4-(tetrahydro-2H-pyran-2-yl)-4H-1,2,4-triazole (2.294 g, 7.12 mmol), bis (pinacolato)diboron (1.898 g, 7.48 mmol), [1,1'-bis (diphenylphosphino)-ferrocene]dichloropalladium(II), complex with dichloromethane (1:1) (291 mg, 0.36 mmol), potassium acetate (2.096 g, 21.4 mmol) and dimethyl sulfoxide (15 mL) were combined in a round bottom flask and stirred. The atmosphere in the flask was removed under vacuum and replaced with nitrogen three times. The resulting mixture was heated at 90° C. under nitrogen for 4 h. The resulting mixture was diluted with ethyl acetate and filtered through Celite. The filter cake was washed thoroughly with ethyl acetate. The filtrate was washed twice with water, once with brine, dried over magnesium sulfate, filtered and concentrated under reduced pressure. Flash chromatography (30-50% ethyl acetate in hexanes) gave a waxy semi-solid which was triturated with hexane at 45° C. The resulting solids were dried under vacuum to give the desired product (2.10 g, 5.69 mmol, 80% yield) as a pink powder. MS (ESI) m/z 370 [M+1]$^+$.

D. tert-Butyl 1-(3,5-dibromopyrazin-2-ylamino)-2-methyl-1-oxopropan-2-ylcarbamate. 1,1'-Carbonyldiimidazole (2.63 g, 16.24 mmol) was added to a stirred solution of 2-(tert-butoxycarbonylamino)-2-methylpropanoic acid (3.00 g, 14.76 mmol) in N,N-dimethylformamide (4 mL) and dichloromethane (8 mL) at room temperature. The resulting clear colorless mixture was stirred at room temperature under nitrogen for 3 h. N,N-Diisopropylethylamine (3.86 mL, 22.14 mmol) was added followed by 3,5-dibromopyrazin-2-amine (5.60 g, 22.14 mmol). The resulting mixture was heated at 50° C. under a reflux condenser under nitrogen for 71 h. Dichloromethane was removed under reduced pressure. The residue was diluted with ethyl acetate and washed with water. The water layer was extracted with ethyl acetate. The combined organics were washed with brine, dried over magnesium sulfate, filtered and concentrated under reduced pressure. The residue was triturated with 30% ethyl acetate in hexane and solids collected by vacuum filtration. The filtrate was concentrated under reduced pressure and purified using flash chromatography (5-50% ethyl acetate in hexane). Fractions containing the desired product were combined with the solids obtained by filtration and concentrated under reduced pressure. The residue was dried under high vacuum to give the desired product (2.38 g, 5.43 mmol, 37% yield) as an off-white solid. MS (ESI) m/z 439.3 [M+1]$^+$, 461.1 [M+Na]$^+$.

E. N-(3,5-Dibromopyrazin-2-yl)-2-methyl-2-(2-(tetrahydro-2H-pyran-4-yl)ethylamino)propanamide trifluoroacetate. TFA (3.66 mL, 47.5 mmol) was added to a stirred mixture of tert-butyl 1-(3,5-dibromopyrazin-2-ylamino)-2-methyl-1-oxopropan-2-ylcarbamate (1.04 g, 2.374 mmol) in dichloromethane (20 mL). The resulting clear yellow solution was stirred at room temperature for 3 h. All volatiles were removed under reduced pressure and the residue dried under high vacuum to give a yellow semi-solid. MS (ESI) m/z 339.1 [M+1]$^+$. Sodium sulfate (1.686 g, 11.87 mmol) was added followed by 2-(tetrahydro-2H-pyran-4-yl)acetaldehyde (0.396 g, 3.09 mmol) and 1,2-dichloroethane (20 mL). The resulting mixture was stirred vigorously and heated at 80° C. under a reflux condenser under nitrogen for 2.5 h. More 2-(tetrahydro-2H-pyran-4-yl)acetaldehyde (0.100 g, 0.780 mmol) and sodium sulfate (1.00 g, 7.04 mmol) were added and heating at 80° C. continued for another 2 h. The resulting yellow solution was removed by pipette from the solid sodium sulfate into a dry 250 mL round bottom flask equipped with a stirbar. The resulting mixture was stirred vigorously and cooled to 0° C. under nitrogen. Sodium triacetoxyborohydride (0.553 g, 2.61 mmol) was added slowly. The resulting mixture was stirred vigorously at 0° C. under nitrogen for 30 min. The cold bath was removed and the resulting mixture stirred at room temperature under nitrogen for 2 h. The mixture was cooled to 0° C. and more sodium triacetoxyborohydride (0.250 g, 1.180 mmol) was added. The cold bath was removed and the resulting mixture stirred at room temperature under nitrogen for 1.5 h. More sodium triacetoxyborohydride (0.055 g, 0.260 mmol) was added. The resulting mixture was stirred vigorously at room temperature under nitrogen for 1 h and then stirred overnight at 0° C. The resulting mixture was diluted with methanol and the volatiles removed under reduced pressure. The residue was taken up in methanol, filtered and purified using reverse-phase preparatory HPLC (10-40% acetonitrile+0.1% TFA in water+0.1% TFA, over 30 min). Fractions containing the desired product were combined and the solvent removed under reduced pressure. The residue was dried under vacuum to give the desired product (0.890 g, 1.978 mmol, 67% yield) as a slightly yellow foam-solid. MS (ESI) m/z 451.3 [M+1]$^+$.

F. 6-Bromo-3,3-dimethyl-4-(2-(tetrahydro-2H-pyran-4-yl)ethyl)-3,4-dihydropyrazino[2,3-b]pyrazin-2(1H)-one. N-(3,5-Dibromopyrazin-2-yl)-2-methyl-2-(2-(tetrahydro-2H-pyran-4-yl)ethylamino)propanamide trifluoroacetate (0.856 g, 1.517 mmol), N,N-diisopropylethylamine (1.321 mL, 7.59 mmol) and 1,4-dioxane (25 mL) were combined in a sealable vessel with a stirbar. The system was purged with nitrogen and the resulting mixture was sealed, stirred vigorously and heated at 110° C. for 2.5 h. The reaction mixture was concentrated under reduced pressure and purified using flash chromatography (5-50% ethyl acetate in hexane) to give the desired product (0.394 g, 1.068 mmol, 70% yield) as a white solid. MS (ESI) m/z 369.4 [M]$^+$, 371.3 [M+2]$^+$.

G. 3,3-Dimethyl-6-(2-methyl-4-(4-(tetrahydro-2H-pyran-2-yl)-4H-1,2,4-triazol-3-yl)phenyl)-4-(2-(tetrahydro-2H-pyran-4-yl)ethyl)-3,4-dihydropyrazino[2,3-b]pyrazin-2(1H)-one. 3-(3-Methyl-4-(4,4,5,5-tetramethyl-1,3,2-dioxaborolan-2-yl)phenyl)-4-(tetrahydro-2H-pyran-2-yl)-4H-1,2,4-triazole (1 equiv), 6-bromo-3,3-dimethyl-4-(2-(tetrahydro-2H-pyran-4-yl)ethyl)-3,4-dihydropyrazino[2,3-b]pyrazin-2(1H)-one (1 equiv), [1,1'-bis(diphenylphosphino)-ferrocene]dichloropalladium(II), complex with dichloromethane (1:1) (0.1 equiv), 1 M sodium carbonate in water (3 equiv), 1,4-dioxane and isopropanol were combined and the system was purged with nitrogen. The resulting mixture was stirred vigorously and heated at 100° C. for 1.5 h. The resulting mixture was cooled to room temperature, diluted with methanol and the volatiles removed under reduced pressure. The residue was partitioned between dichloromethane and water, shaken and the layers separated. The water layer was extracted with dichloromethane. The combined organics were dried over magnesium sulfate, filtered and concentrated under reduced pressure. The residue was purified using flash chromatography (20-100% ethyl acetate in hexane followed by 0-10% methanol in dichloromethane) to give the desired product in 97% yield. MS (ESI) m/z 532.7 [M+1]$^+$.

H. 3,3-Dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one. 6 N Hydrochloric acid in water was added to a stirred mixture of 3,3-dimethyl-6-(2-methyl-4-(4-(tetrahydro-2H-pyran-2-yl)-4H-1,2,4-triazol-3-yl)phenyl)-4-(2-(tetrahydro-2H-pyran-4-yl)ethyl)-3,4-dihydropyrazino[2,3-b]pyrazin-2(1H)-one in ethanol at 80° C. The resulting mixture was stirred vigorously and heated at 80° C. under a reflux condenser under nitrogen for 70 min. The resulting mixture was filtered and purified using reverse-phase preparatory HPLC (10-65% acetonitrile+0.1% TFA in water+0.1% TFA, over 30 min). Fractions containing the desired product were combined, neutralized with saturated aqueous sodium bicarbonate and the acetonitrile removed under reduced pressure. Solids were collected by vacuum filtration, washed thoroughly with water and diethyl ether and dried under high vacuum at 50° C. to give the desired product in 48% yield. $^1$H NMR (400 MHz, DMSO-d$_6$) δ (ppm) 11.32 (br. s., 1H), 8.44 (br. s., 1H), 7.96 (s, 1H), 7.90 (d, J=8.59 Hz, 1H), 7.70 (s, 1H), 7.56 (d, J=7.81 Hz, 1H), 3.78 (dd, J=2.93, 11.13 Hz, 2H), 3.52-3.64 (m, 2H), 3.23 (t, J=10.93 Hz, 2H), 2.48 (s, 3H), 1.51-1.66 (m, 5H), 1.49 (s, 6H), 1.11-1.26 (m, 2H); MS (ESI) m/z 448.3 [M+1]$^+$.

Example 3

7-(2-Methyl-4-(4H-1,2,4-triazol-3-yl)phenyl)-3,4-dihydropyrazino[2,3-b]pyrazin-2(1H)-one hydrochloride

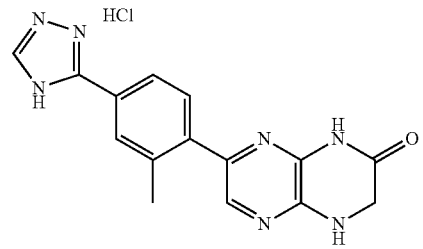 [SMILES: Cl ; Cc1cc(-c2nnc[nH]2)ccc1-c1cnc2c(n1)NC(=O)CN2]

A. Ethyl 2-(5-bromo-3-(2,4-dimethoxybenzylamino)pyrazin-2-ylamino)acetate. Ethyl 2-(3,5-dibromopyrazin-2-ylamino)acetate (See Example 1.C) (1.06 g, 3.13 mmol), (2,4-dimethoxyphenyl)methanamine (0.601 g, 3.60 mmol), N,N-diisopropylethylamine (1.63 mL, 9.38 mmol) and dimethylsulfoxide (1.6 mL) were combined in a microwave vial with a stirbar and heated in a microwave reactor at 150° C. for 2 h. The resulting mixture was purified using flash chromatography (5-60% ethyl acetate in hexane). Fractions containing the desired product were combined and concentrated nearly to dryness under reduced pressure. Ethyl acetate (2 mL) and hexane (18 mL) was added. The resulting solids were collected by vacuum filtration, washed with hexane and dried under high vacuum to give the desired product (0.636 g, 1.495 mmol, 48% yield) as a light pink solid. $^1$H NMR (300 MHz, DMSO-d$_6$) δ (ppm) 7.24 (s, 1H), 7.19 (d, J=8.52 Hz, 1H), 7.11 (t, J=5.63 Hz, 1H), 6.84 (t, J=4.81 Hz, 1H), 6.59 (d, J=2.47 Hz, 1H), 6.50 (dd, J=2.20, 8.24 Hz, 1H), 4.37 (d, J=4.67 Hz, 2H), 3.96-4.15 (m, 4H), 3.81 (s, 3H), 3.75 (s, 3H), 1.17 (t, 3H); MS (ESI) m/z 425.3 [M]$^+$, 426.9 [M+2]$^+$.

B. 7-Bromo-3,4-dihydropyrazino[2,3-b]pyrazin-2(1H)-one trifluoroacetate. Ethyl 2-(5-bromo-3-(2,4-dimethoxybenzylamino)pyrazin-2-ylamino)acetate (0.484 g, 1.138 mmol), methanol (0.461 mL, 11.38 mmol) and TFA (7 mL) were combined in a sealable vessel with a stirbar. The system was purged with nitrogen. The resulting mixture was sealed, stirred vigorously and heated at 75° C. in an oil bath for 25 min. The resulting mixture was diluted with water (14 mL) and stirred at room temperature for 5 min. Solids were collected by vacuum filtration, washed with water and diethyl ether and dried under high vacuum to give the desired product (0.375 g, 1.093 mmol, 96% yield) as a pink solid. MS (ESI) m/z 229.0 [M]+, 231.3 [M+2]+.

C. 7-(2-Methyl-4-(4-(tetrahydro-2H-pyran-2-yl)-4H-1,2,4-triazol-3-yl)phenyl)-3,4-dihydropyrazino[2,3-b]pyrazin-2(1H)-one. 3-(3-Methyl-4-(4,4,5,5-tetramethyl-1,3,2-dioxaborolan-2-yl)phenyl)-4-(tetrahydro-2H-pyran-2-yl)-4H-1,2,4-triazole (See Example 2.C) (0.465 g, 1.259 mmol), 7-bromo-3,4-dihydropyrazino[2,3-b]pyrazin-2(1H)-one trifluoroacetate (0.432 g, 1.259 mmol), [1,1'-bis(diphenylphosphino)-ferrocene]dichloropalladium(II), complex with dichloromethane (1:1) (0.103 g, 0.126 mmol), sodium carbonate (1 M in water, 3.78 mL, 3.78 mmol), 1,4-dioxane (2.5 mL) and isopropanol (1 mL) were combined in a sealable vessel with a stirbar. The system was purged with nitrogen. The resulting mixture was sealed, stirred vigorously and heated at 100° C. for 70 min. The resulting mixture was diluted with water and dichloromethane and filtered through a fritted funnel. Solids were washed with 20% methanol in dichloromethane. Filtrate and wash were combined and the solvent was removed under reduced pressure. The residue was triturated with acetonitrile. Water was added. Solids were collected by vacuum filtration and washed thoroughly with water and diethyl ether. Solids were washed with 20% methanol in dichloromethane. Filtrate and wash were combined and the solvent was removed under reduced pressure. The residue was taken up in hot DMSO and methanol, filtered and purified using reverse-phase preparatory HPLC (20-65% acetonitrile+0.1% TFA in water+0.1% TFA, over 30 min). Fractions containing the desired product were combined, neutralized with saturated aqueous sodium bicarbonate and concentrated nearly to dryness under reduced pressure. Solids were collected by vacuum filtration, washed with water and dried under high vacuum to give the desired product (0.072 g, 0.184 mmol, 15% yield) as an off-white solid. MS (ESI) m/z 392.1 [M+1]+.

D. 7-(2-Methyl-4-(4H-1,2,4-triazol-3-yl)phenyl)-3,4-dihydropyrazino[2,3-b]pyrazin-2(1H)-one hydrochloride. Hydrochloric acid (6 N in water 0.149 mL, 0.894 mmol) was added to a stirred mixture of 7-(2-methyl-4-(4-(tetrahydro-2H-pyran-2-yl)-4H-1,2,4-triazol-3-yl)phenyl)-3,4-dihydropyrazino[2,3-b]pyrazin-2(1H)-one (0.070 g, 0.179 mmol) in ethanol (3 mL) at 80° C. The system was purged with nitrogen. The resulting mixture was sealed and heated at 80° C. The resulting mixture was heated at 80° C. for 25 min and then cooled to room temperature. Solids were collected by filtration, washed with methanol and dried under high vacuum at 40° C. to give the desired product (0.058 g, 0.169 mmol, 94% yield) as a white solid. 1H NMR (300 MHz, DMSO-d6) δ (ppm) 11.32 (s, 1H), 8.66 (s, 1H), 7.97 (s, 1H), 7.92 (dd, J=1.37, 7.97 Hz, 1H), 7.74 (s, 1H), 7.50 (d, J=7.97 Hz, 1H), 4.14 (s, 2H), 2.44 (s, 3H); MS (ESI) m/z 308.3 [M+1]+.

Example 4

6-(4-(2-Hydroxypropan-2-yl)phenyl)-4-(2-(tetrahydro-2H-pyran-4-yl)ethyl)-3,4-dihydropyrazino[2,3-b]pyrazin-2(1H)-one

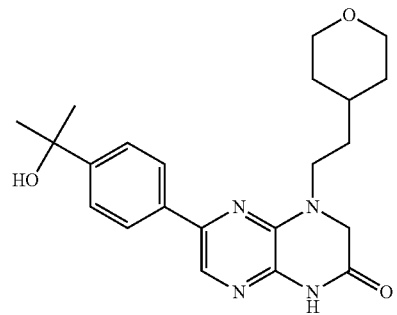 [SMILES: CC(C)(O)c1ccc(-c2cnc3c(n2)N(CCC2CCOCC2)CC(=O)N3)cc1]

A. 2-Bromo-N-(3,5-dibromopyrazin-2-yl)acetamide. A solution of 2-amino-3,5-dibromopyrazine (6.17 g, 23.7 mmol) and bromoacetic anhydride (3.0 g, 11.9 mmol) in acetonitrile (40 mL) was stirred at 70° C. Upon complete consumption of starting material (by TLC), the solution was condensed and partitioned between water and ethyl acetate (3×). The organic layers were combined, dried over magnesium sulfate, filtered and the solvent was removed under reduced pressure. The resulting material was purified using Biotage column chromatography (5-80% ethyl acetate in hexanes) to afford the title compound (3.78 g, 10.1 mmol, 85% yield). MS (ESI) m/z 372.1 [M−2]+, 374.0 [M]+, 376.1 [M+2]+, 378.3 [M+4]+.

B. 6-Bromo-4-(2-(tetrahydro-2H-pyran-4-yl)ethyl)-3,4-dihydropyrazino[2,3-b]pyrazin-2(1H)-one. 2-Bromo-N-(3,5-dibromopyrazin-2-yl)acetamide (3.30 g, 8.83 mmol) and 2-(tetrahydro-2H-pyran-4-yl)ethanamine hydrochloride (1.46, 8.83 mmol) and diisopropyl ethylamine (6.67 mL, 35.3 mmol) were combined and heated at 85° C. Upon complete consumption of starting material (by TLC), the reaction solution was condensed and purified via Biotage chromatography (0-100% ethyl acetate in hexanes) to afford the title compound (1.53 g, 4.48 mmol, 50% yield). MS (ESI) m/z 341.4 [M]+, 343.1 [M+2]+.

C. 2-(4-Bromophenyl)propan-2-ol. 1-(4-Bromophenyl)ethanone (9.25 g, 46.5 mmol) was dissolved in tetrahydrofuran (200 mL). The solution was cooled in a −50° C. bath. Methylmagnesium bromide (3M in ether, 46.5 mL, 139 mmol) was added over a 15 min period. The reaction was allowed to warm to room temperature and then stirred for 20 h. The reaction was quenched with saturated ammonium chloride and then extracted with ethyl acetate. The organic layer was dried over magnesium sulfate, filtered and concentrated to give an oil. The oil was purified on a silica gel column (0-20% ethyl acetate in hexanes) to give the product a colorless oil (9.1 g, 46.2 mmol, 91% yield). MS (ESI) m/z 197.1 [M]+, 199.1 [M+2]+.

D. 2-(4-(4,4,5,5-Tetramethyl-1,3,2-dioxaborolan-2-yl)phenyl)propan-2-ol. 2-(4-Bromophenyl)propan-2-ol (4.7 g, 21.85 mmol), bis(pinacolato)diboron (6.66 g, 26.2 mmol), potassium acetate (6.43 g, 65.6 mmol) and dimethyl sulfoxide (50 mL) were stirred and degassed under vacuum for 10 min. [1,1'-Bis(diphenyl-phosphino)ferrocene]dichloro-palladium (II) complex with dichloromethane (1:1) (0.892 g, 1.093 mmol) was added and the reaction was degassed for another 5 min. The reaction was then heated to 80° C. under nitrogen for 2 h. The reaction was cooled to room temperature and then extracted with 1:1 ether:ethyl acetate and water. The resulting black emulsion was filtered through a pad of celite and the filtrate combined with extraction layers. The organic layer was dried over magnesium sulfate, filtered and then purified on silica gel column (0-25% ethyl acetate in hexanes). The product fractions were concentrated and then triturated in hexanes to give a white solid, (4.0 g, 15.3 mmol, 70% yield). MS (ESI) m/z 263.3 [M+1]$^+$.

E. 6-(4-(2-Hydroxypropan-2-yl)phenyl)-4-(2-(tetrahydro-2H-pyran-4-yl)ethyl)-3,4-dihydropyrazino[2,3-b]pyrazin-2(1H)-one. 6-Bromo-4-(2-(tetrahydro-2H-pyran-4-yl)ethyl)-3,4-dihydropyrazino[2,3-b]pyrazin-2(1H)-one (0.250 g, 0.733 mmol), 2-(4-(4,4,5,5-tetramethyl-1,3,2-dioxaborolan-2-yl)phenyl)propan-2-ol (0.192 g, 0.733 mmol) and dichloro[1,1'-bis(diphenylphosphino)ferrocene]palladium (II) dichloromethane (0.030 g, 0.037 mmol) were combined in dimethylformamide (1.0 mL). Sodium carbonate (0.311 g, 2.93 mmol) in water (0.2 mL) was added and the reaction solution was then heated in a Biotage Emrys Optimizer microwave reactor at 120° C. for 15 min. The cooled reaction solution was filtered through Celite and the filter cake was washed with ethyl acetate. Filtrate and ethyl acetate wash were combined and solvent removed under reduced pressure. The resulting material was purified using Biotage column chromatography (0-5% methanol in ethyl acetate) followed by trituration with dimethylformamide and water to afford the title compound (0.074 g, 0.19 mmol, 25%) $^1$H NMR (400 MHz, DMSO-d$_6$) δ (ppm) 12.24 (s, 1H), 7.98 (s, 1H), 7.89 (d, J=8.39 Hz, 2H), 7.53 (d, J=8.39 Hz, 1H), 5.04 (s, 1H), 4.16 (s, 1H), 3.82 (dd, J=11.1, 2.39 Hz, 2H), 3.61 (t, J=7.59 Hz, 2H), 3.25 (t, J=9.59 Hz, 3H), 1.70 (s, 1H), 1.66 (s, 1H), 1.58 (m, 3H), 1.44 (s, 6H), 1.25 (m, 2H); MS (ESI) m/z 397.2 [M+1]$^+$; mp 210-212° C.

Example 5

6-(6-(2-Hydroxypropan-2-yl)pyridin-3-yl)-4-(2-morpholinoethyl)-3,4-dihydropyrazino[2,3-b]pyrazin-2(1H)-one

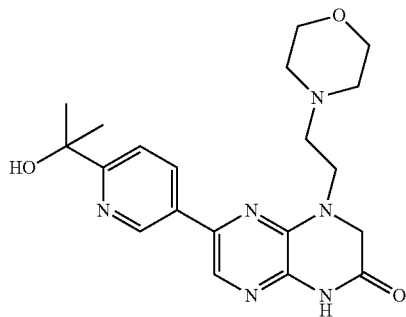 [SMILES: CC(C)(O)c1ccc(-c2cnc3c(n2)N(CCN2CCOCC2)CC(=O)N3)cn1]

A. 2-Chloro-N-(3,5-dibromopyrazin-2-yl)acetamide. A solution of 2-amino-3,5-dibromopyrazine (3.0 g, 11.9 mmol) and chloroacetic anhydride (4.2 g, 8.7 mmol) were reacted in acetonitrile (10 mL) at 70° C. for 16 h. The solution was condensed and diluted with ethyl acetate. The organics were washed with a 1:1 solution of sodium bicarbonate (saturated) and potassium carbonate (1.75 M in water) (4×). The organics were combined, dried over magnesium sulfate, filtered and solvent removed under reduced pressure. The resulting solid was triturated with 10% ethyl acetate in hexanes to afford the title compound (3.12 g, 9.3 mmol, 72% yield). MS (ESI) m/z 328.3 [M−1]$^+$, 330.4 [M+1]$^+$, 332.3 [M+3]$^+$.

B. N-(3,5-Dibromopyrazin-2-yl)-2-iodoacetamide. To a solution of 2-chloro-N-(3,5-dibromopyrazin-2-yl)acetamide (3.0 g, 9.11 mmol) in acetone (40 mL) was added sodium iodide (13.65 g, 91 mmol) dissolved in acetone (20 mL). Solution was allowed to stir at ambient temperature for 16 h. Solution was condensed under reduced pressure and diluted with ethyl acetate (500 mL) and washed consecutively with water (5×) to remove the blue color. Organics were dried over magnesium sulfate, filtered and solvent removed under reduced pressure to afford the crude product. The solid was diluted with 10% ethyl acetate in hexanes (40 mL) and sonicated while scraping the sides of the flask. The solution was then heated under a heat gun for 5 min, then cooled while sonicating at ambient temperature. The resulting solid was filtered and washed with additional hexanes and dried under vacuum to afford the title compound (3.0 g, 7.13 mmol, 78% yield). MS (ESI) m/z 420.3 [M−1]$^+$, 422.0 [M+1]$^+$, 424.0 [M+3]$^+$.

C. 6-Bromo-4-(2-morpholinoethyl)-3,4-dihydropyrazino[2,3-b]pyrazin-2(1H)-one. N-(3,5-Dibromopyrazin-2-yl)-2-iodoacetamide (0.5 g, 1.188 mmol), diisopropylethylamine (0.415 mL, 2.376 mmol) and 2-morpholinoethanamine (0.162 g, 1.248 mmol) were combined in acetonitrile (5 mL). The solution was heated to 45° C. for 1 h. Solution was condensed and diluted with 75% ethyl acetate in hexanes. The resulting solid was filtered and the filtrate collected and condensed followed by purification via Biotage chromatography (0-75% ethyl acetate in hexanes then 0-10% methanol in ethyl acetate) to afford the title compound (0.228 g, 0.67 mmol, 56% yield). MS (ESI) m/z 342.4 [M]$^+$, 344.4 [M+2]$^+$.

D. 2-(5-Bromopyridin-2-yl)propan-2-ol. 2,5-Dibromopyridine (1.04 g, 4.39 mmol) was dissolved in toluene (22 mL) in a 100 mL round-bottomed flask. The mixture was cooled to −78° C. n-Butyllithium (3.02 mL, 4.83 mmol) was added dropwise. The mixture was stirred 30 min, followed by the addition of acetone (2 mL). The mixture was stirred 40 min and then let warm to rt. The mixture was washed with ammonium chloride (5% aq, 50 mL), water (50 mL) and then brine (50 mL). The organic layer was dried over sodium sulfate, filtered and concentrated. The residue was purified by Biotage (16% ethyl acetate in hexanes). Concentration of the desired fractions afforded the product (0.82 g, 3.78 mmol, 86% yield). MS (ESI) m/z 216.0 [M]$^+$, 218.1 [M+2]$^+$.

E. 2-(5-(Trimethylstannyl)pyridin-2-yl)propan-2-ol. 2-(5-Bromopyridin-2-yl)propan-2-ol (0.34 g, 1.574 mmol), 1,1,1,2,2,2-hexamethyldistannane (0.361 mL, 1.652 mmol) and tetrakis(triphenylphosphine)palladium(0) (0.182 g, 0.157 mmol) were combined in toluene (5 mL) in a 50 mL resealable flask. The reaction was stirred at 115° C. for 1.5 h. The mixture was then concentrated to about a 2 mL volume. The residue was purified via Biotage (16% ethyl acetate in hexanes). Concentration of the desired fractions afforded the title compound (0.33 g, 1.10 mmol, 70% yield). MS (ESI) m/z 302.1 [M+1]$^+$.

F. 6-(6-(2-Hydroxypropan-2-yl)pyridin-3-yl)-4-(2-morpholinoethyl)-3,4-dihydropyrazino[2,3-b]pyrazin-2(1H)-one. 6-Bromo-4-(2-morpholinoethyl)-3,4-dihydropyrazino[2,3-b]pyrazin-2(1H)-one (0.228 g, 0.666 mmol) and 2-(5-(trimethylstannyl)pyridin-2-yl)propan-2-ol (0.220 g, 0.733 mmol) were combined in dimethylformamide (3 mL). Solution was purged with nitrogen gas followed by the addition of dichloro[1,1'-bis(diphenylphosphino)ferrocene]palladium (II) dichloromethane (0.109 g, 0.133 mmol). Solution was heated to 100° C. for 2 h. Solution was condensed under reduced pressure and the resulting oil purified via reverse-phase-preparative HPLC (5-60% acetonitrile+0.1% TFA in H$_2$O+0.1% TFA, over 30 min) and desired fractions were loaded onto a Strata-XC ion exchange column. The column was washed successively with water, acetonitrile, methanol and 5% ammonium hydroxide in methanol. The product eluted with the 5% ammonium hydroxide in methanol and was concentrated under reduced pressure and dried to afford the title compound (0.070 g, 0.18 mmol, 26% yield). $^1$H NMR (400 MHz, DMSO-d$_6$) δ (ppm) 11.33 (br. s., 1H), 9.05 (d, J=1.56 Hz, 1H), 8.27 (dd, J=8.59, 2.34 Hz, 1H), 8.06 (s, 1H), 7.72 (d, J=8.59 Hz, 1H), 5.27 (s, 1H), 4.29 (s, 2H), 3.71 (t, J=6.44 Hz, 2H), 3.54 (t, J=4.49 Hz, 4H), 2.62 (t, J=6.44 Hz, 2H), 2.40-2.48 (m, 4H), 1.46 (s, 6H); MS (ESI) m/z 399.2 [M+1]$^+$; mp 239-241° C.

Example 6

1-(((trans)-4-Methoxycyclohexyl)methyl)-7-(4-methyl-6-(1H-1,2,4-triazol-3-yl)pyridin-3-yl)-3,4-dihydropyrazino[2,3-b]pyrazin-2(1H)-one

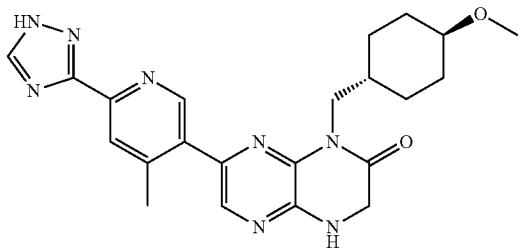 [SMILES: CO[C@H]1CC[C@H](CN2C(=O)CNc3ncc(-c4cnc(-c5nc[nH]n5)cc4C)nc32)CC1]

A. 5-Bromo-4-methylpicolinonitrile. 2,5-Dibromo-4-methylpyridine (5.0 g, 19.9 mmol), copper cyanide (1.43 g, 15.9 mmol), sodium cyanide (0.801 g, 16.3 mmol) and dimethylformamide (30 mL) were combined in a sealed reaction vessel and heated at 158° C. for 3 h. The reaction mixture was purified by silica gel column chromatography (0-80% ethyl acetate in hexanes). The resulting material was subjected to a second silica gel column (0-20% methanol in dichloromethane). Clean fractions were combined and concentrated to afford the title compound as a white solid (2.30 g, 11.6 mmol, 58% yield). MS (ESI) m/z 198.0 [M+1]$^+$.

B. Ethyl 2-(3,5-dibromopyrazin-2-ylamino)acetate. A 2000 mL 3-necked round bottomed flask was charged with 2-amino-3,5-dibromopyrazine (172 g, 680 mmol) in dimethylformamide (860 mL) and cooled to 0-5° C. Cesium carbonate (288 g, 884 mmol) was added in one portion followed by the portion-wise addition of ethyl chloroacetate (87 mL, 816 mmol). The solution was allowed to warm to 20-25° C. then heated to 55° C. (exotherm observed, max temperature observed 76° C.). Once the internal reaction temperature subsided to 65° C. the reaction was heated at 65° C. for ~4 h. The reaction was cooled to 20-25° C. and filtered through filter paper to remove inorganic salts and the solid was washed with dimethylformamide (3 vol). The filtrate was added dropwise to 16 vol of ice-water (8 vol ice/8 vol water) and the slurry was allowed to agitate for 12-24 h. The resulting brown solid was isolated following filtration and washed with water (10 vol) and air-dried. Crude product was dissolved in methyl t-butyl ether (3.46 L, 15 vol). Charcoal (C-906 from Ecosorb, 20 wt %, 46.1 g) was added and the mixture was heated at reflux for 1 h. After cooling to rt, the charcoal was removed over a Celite bed and the filtrate was concentrated to dryness. The crude was dissolved in ethyl acetate (576 mL, 2.5 vol) and concentrated to a thick slurry. A solution of 2% ethyl acetate in heptane (1.15 L, 5 vol) was added and the mixture was stirred at rt for 30-60 min. The product was collected by filtration, washed with heptane (2-3 vol) and dried under high vacuum at 35-40° C. for 16 h to afford the desired compound as an off-white solid (109 g, 47% yield). A second crop was isolated from the mother liquor as follows: the filtrate was concentrated to give a crude oil. Ethyl acetate (1 vol.) was added. The resulting solution was seeded with previously isolated product and cooled at 0-5° C. for 1 h. The resulting solid was collected by filtration and washed with cold ethyl acetate:heptane (1:1 mixture, <1 vol). The solid was dried as described previously and combined with the first crop to provide the title compound (132 g, 57% total yield). MS (ESI) m/z 337.8 [M−1]$^+$, 339.8 [M+1]$^+$, 341.8 [M+3]$^+$.

C. 7-Bromo-1-(((trans)-4-methoxycyclohexyl)methyl)-3,4-dihydropyrazino[2,3-b]pyrazin-2(1H)-one. A solution of ethyl 2-(3,5-dibromopyrazin-2-ylamino)acetate (500 mg, 1.47 mmol), ((trans)-4-methoxycyclohexyl)methanamine (317 mg, 2.21 mmol) and diisopropylethyl amine (0.77 mL, 4.42 mmol) in anhydrous dimethylsulfoxide (8.0 mL) was placed in a microwave vessel (20 mL). The reaction was heated to 150° C. for 1 h. The reaction was poured into water, extracted with ethyl acetate (2×100 mL), dried over sodium sulfate, filtered and concentrated under reduced pressure. The resulting material was dissolved in acetic acid (30 mL) and placed in a sealed tube. The reaction was heated to 120° C. overnight. The solution was cooled, concentrated under reduced pressure, neutralized with saturated sodium bicarbonate, extracted with ethyl acetate (3×100 mL), dried over sodium sulfate, filtered and adsorbed onto silica gel. Purification by flash chromatography (50% ethyl acetate in hexanes) gave a light orange solid (400 mg, 1.12 mmol, 76% yield). MS (ESI) m/z 355.2 [M+]$^+$, 357.2 {M+2]$^+$.

D. 1-(((trans)-4-Methoxycyclohexyl)methyl)-7-(trimethylstannyl)-3,4-dihydropyrazino[2,3-b]pyrazin-2(1H)-one. 7-Bromo-1-(((trans)-4-methoxycyclohexyl)methyl)-3,4-dihydropyrazino[2,3-b]pyrazin-2(1H)-one (2.71 g, 7.63 mmol), 1,1,1,2,2,2-hexamethyldistannane (3.00 g, 9.15 mmol) and tetrakis(triphenylphosphine)palladium(0) (882 mg, 0.76 mmol) were combined in a sealed tube charged with anhydrous dioxane (40 mL) and purged with nitrogen gas. The reaction was heated to 100° C. for 4 h. The reaction was diluted with ethyl acetate, filtered through celite, washed celite with ethyl acetate and the filtrate concentrated under reduced pressure. The crude material was purified by flash chromatography (0-50% ethyl acetate in hexane) and desired fractions were combined and concentrated to give a light yellow solid (2.32 g, 5.28 mmol, 69% yield). MS (ESI) m/z 441.1 [M+1]$^+$.

E. 5-(8-(((trans)-4-Methoxycyclohexyl)methyl)-7-oxo-5,6,7,8-tetrahydropyrazino[2,3-b]pyrazin-2-yl)-4-methylpicolinonitrile. 1-(((trans)-4-Methoxycyclohexyl)methyl)-7-(trimethylstannyl)-3,4-dihydropyrazino[2,3-b]pyrazin-2(1H)-one (0.721 g, 1.64 mmol), 5-bromo-4-methylpicolinonitrile (0.323 g, 1.64 mmol), tris(dibenzylideneacetone)dipalladium(0) (0.150 g, 0.164 mmol), triethylamine (0.687 mL, 4.93 mmol), tri-ortho-tolylphosphine (0.100 g, 0.328 mmol) and dimethylformamide (8 mL) were combined in a sealed reaction vessel. Nitrogen was bubbled through the reaction for 5 min and reaction was heated at 100° C. for 3 h. Reaction is filtered, concentrated and purified by silica gel column chromatography (0-80% ethyl acetate in hexanes). Fractions were combined and concentrated to afford the crude title compound used directly for next step (0.607 g, 1.55 mmol, 94% yield). MS (ESI) m/z 393.5 [M+1]⁺.

F. 5-(8-(((trans)-4-Methoxycyclohexyl)methyl)-7-oxo-5,6,7,8-tetrahydropyrazino[2,3-b]pyrazin-2-yl)-4-methylpicolinamide. 5-(8-(((trans)-4-Methoxycyclohexyl)methyl)-7-oxo-5,6,7,8-tetrahydropyrazino[2,3-b]pyrazin-2-yl)-4-methylpicolinonitrile (0.607 g, 1.55 mmol), trifluoroacetic acid (2.0 mL, 26.0 mmol) and sulfuric acid (0.5 mL, 9.38 mmol) were combined and heated at 65° C. for 1 h. Reaction pH was adjusted to 10 with sodium carbonate and the resulting solution was extracted with ethyl acetate (3×15 mL). Organic layers were collected, dried over magnesium sulfate, concentrated and purified using reverse-phase preparatory HPLC (10-100% acetonitrile+0.1% TFA in H₂O+0.1% TFA, over 30 min). Clean fractions were combined and condensed under reduced pressure and dried under high vacuum to afford the title compound as a yellow solid (0.425 g, 1.04 mmol, 67% yield). MS (ESI) m/z 411.5 [M+1]⁺.

G. (Z)—N-((Dimethylamino)methylene)-5-(8-(((trans)-4-methoxycyclohexyl)methyl)-7-oxo-5,6,7,8-tetrahydropyrazino[2,3-b]pyrazin-2-yl)-4-methylpicolinamide. 5-(8-(((trans)-4-Methoxycyclohexyl)methyl)-7-oxo-5,6,7,8-tetrahydropyrazino[2,3-b]pyrazin-2-yl)-4-methylpicolinamide (0.412 g, 1.00 mmol), dimethylformamide dineopentylacetal (1.5 mL) and tetrahydrofuran (10 mL) were combined and heated at 85° C. for 3 h. Reaction was concentrated under a stream of nitrogen placed in reaction vessel. Crude product was used directly for next step (0.467 g, 1.00 mmol, 100% yield). MS (ESI) m/z 466.6 [M+1]⁺

H. 1-(((trans)-4-Methoxycyclohexyl)methyl)-7-(4-methyl-6-(1H-1,2,4-triazol-3-yl)pyridin-3-yl)-3,4-dihydropyrazino[2,3-b]pyrazin-2(1H)-one. (Z)—N-((Dimethylamino)methylene)-5-(8-(((trans)-4-methoxycyclohexyl)methyl)-7-oxo-5,6,7,8-tetrahydropyrazino[2,3-b]pyrazin-2-yl)-4-methylpicolinamide (0.467 g, 1.00 mmol) was added to acetic acid (6 mL). The reaction was cooled to 0° C. and hydrazine (1.00 mL, 32 mmol) was added dropwise. The reaction was allowed to stir and warm to 25° C. over 10 min. Reaction was concentrated under a stream of nitrogen placed in reaction vessel. Water (5 mL) was added and the product was collected by filtration and purified using reverse-phase semi-preparatory HPLC (20-70% acetonitrile+0.1% TFA in H₂O+0.1% TFA, over 30 min). Clean fractions were combined and condensed under reduced pressure and dried under high vacuum to afford the title compound as a yellow solid (0.046 g, 0.106 mmol, 11% yield). ¹H NMR (400 MHz, METHANOL-d₄) δ (ppm) 8.72 (s, 1H), 8.62 (s, 1H), 8.37 (s, 1H), 7.93 (s, 1H), 4.30 (s, 2H), 3.99 (d, J=7.03 Hz, 2H), 3.32 (s, 3H), 3.08-3.17 (m, 1H), 2.71-2.76 (m, 3H), 2.06 (br. s., 2H), 1.80-1.89 (m, 1H), 1.74 (br. s., 2H), 1.09 (d, J=11.32 Hz, 4H); MS (ESI) m/z 435.5 [M+1]⁺.

Example 7

7-(5-Fluoro-2-methyl-4-(1H-1,2,4-triazol-3-yl)phenyl)-1-isopropyl-3,4-dihydropyrazino[2,3-b]pyrazin-2(1H)-one

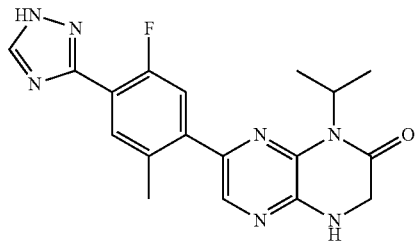 [SMILES: Cc1cc(-c2nc[nH]n2)c(F)cc1-c1cnc2c(n1)N(C(C)C)C(=O)CN2]

A. Ethyl 2-(5-bromo-3-(isopropylamino)pyrazin-2-ylamino)acetate. A mixture of ethyl 2-(3,5-dibromopyrazin-2-ylamino)acetate (See Example 6.B) (1.5 g, 4.43 mmol), isopropylamine (0.17 g, 4.87 mmol), N,N-diisopropylethylamine (1.14 g, 8.84 mmol) and dimethylsulfoxide (10 mL) in a reaction vial was heated in an oil bath at 150° C. for 16 h. After being cooled to room temperature, the resulting mixture was poured into water and extracted with ethyl acetate. The organic layer was dried over sodium sulfate, filtered, evaporated under reduced pressure and purified on silica gel column chromatography (10-20% ethyl acetate in petroleum ether) to give the title compound (780 mg, 55.7% yield). MS (ESI) m/z 316.9 [M+1]⁺.

B. 7-Bromo-1-isopropyl-3,4-dihydropyrazino[2,3-b]pyrazin-2(1H)-one. A mixture of ethyl 2-(5-bromo-3-(isopropylamino)pyrazin-2-ylamino)acetate (780 mg, 2.26 mmol), methanol (5 mL) and TFA (10 mL) in a sealable vessel was purged with nitrogen, sealed, stirred vigorously and heated at 90° C. with an oil bath for 16 h. The resulting mixture was diluted with methanol and the solvent was removed under reduced pressure. Methanol (10 mL) was added and the solvent was removed under reduced pressure again. Methanol (10 mL) and sodium bicarbonate were added. The resulting mixture was stirred at room temperature until pH=6 (in water), the solvent was removed under reduced pressure. Water (20 mL) was added. The mixture was extracted with methylene chloride (20 mL×3). The organic layer was dried over anhydrous sodium sulfate, concentrated to give the crude product and purified on silica column chromatography (10-20% ethyl acetate in petroleum ether) to give the title compound (360 mg, 39.4% yield).

C. 1-Isopropyl-7-(trimethylstannyl)-3,4-dihydropyrazino[2,3-b]pyrazin-2(1H)-one. 7-Bromo-1-isopropyl-3,4-dihydropyrazino[2,3-b]pyrazin-2(1H)-one (0.5 g, 1.844 mmol), hexamethylditin (0.725 g, 2.213 mmol), tetrakis(triphenylphosphine)palladium(0) (0.213 g, 0.184 mmol) and 1,4-dioxane (3 mL) were combined in a sealable vessel with a stirbar. Nitrogen gas was bubbled through the solution. The vessel was sealed, stirred vigorously and heated at 100° C. for 2 h. The resulting cloudy black mixture was diluted with ethyl acetate, filtered and the filter cake washed thoroughly with ethyl acetate. The filtrate was concentrated under reduced pressure and purified using silica gel flash column chromatography (20-80% ethyl acetate in hexanes) to give the desired product (0.49 g, 1.38 mmol, 75% yield) as a yellow-white solid. MS (ESI) m/z 357.4 [M+2]⁺.

D. 4-Bromo-2-fluoro-5-methylbenzamide. To a solution of 4-bromo-2-fluoro-5-methylbenzonitrile (40 g, 190 mmol) in a mixture of sulfuric acid (98%) and TFA (v/v=4:1, 480 mL) was stirred at 80° C. for 16 h. After the mixture was cooled to room temperature, the resulting mixture was poured into ice-cold water. The resulting precipitate was collected by filtration, washed with water and dried under reduced pressure to give the title compound (41 g, 95% yield) as a white solid. MS (ESI) m/z 232.0 [M+1]$^+$.

E. 4-Bromo-N-((dimethylamino)methylene)-2-fluoro-5-methylbenzamide. A solution of 4-bromo-2-fluoro-5-methylbenzamide (20 g, 86 mmol) in N,N-dimethyl-formamide dimethylacetal (200 mL) was stirred at 100° C. under nitrogen for 3 h. The resulting mixture was concentrated and dried to give the desired product (24.6 g, 95% yield) as a yellow oil, which was used in the next step without further purification. MS (ESI) m/z 287.0 [M+1]$^+$.

F. 3-(4-Bromo-2-fluoro-5-methylphenyl)-1H-1,2,4-triazole. To a solution of 4-bromo-N-((dimethylamino)methylene)-2-fluoro-5-methylbenzamide (24.6 g, 86.2 mmol) in acetic acid (200 mL) was added dropwise hydrazine hydrate (25 mL, 0.70 mol) at 0° C. The reaction mixture was stirred at room temperature overnight. The mixture was filtered washed with water (500 mL×3) and dried under reduced pressure to give the title compound (15 g, 68% yield) as a white solid. MS (ESI) m/z 256.0 [M+1]$^+$.

G. 3-(4-Bromo-2-fluoro-5-methylphenyl)-1-(tetrahydro-2H-pyran-2-yl)-1H-1,2,4-triazole. A solution of 3-(4-bromo-2-fluoro-5-methylphenyl)-1H-1,2,4-triazole (15 g, 60 mmol), toluene-4-sulfonic acid (2.0 g, 12 mmol) and 3,4-dihydro-2H-pyran (20 g, 240 mmol) in tetrahydrofuran (200 mL) was stirred at 80° C. under nitrogen for 15 h. The resulting mixture was concentrated and purified on silica gel column (1-25% ethyl acetate in petroleum ether) to give the protected triazole product (15 g, 75% yield) as a white solid. $^1$H NMR (DMSO-d$_6$, 400 MHz): δ (ppm) 8.83 (s, 1H), 7.96 (d, J=7.6 Hz, 1H), 7.66 (d, J=10.0 Hz, 1H), 5.61 (dd, J$_1$=2.4 Hz, J$_2$=9.6 Hz, 1H), 3.96 (d, J=1.6 Hz, 1H), 3.69 (m, 1H), 2.36 (s, 3H), 2.00 (m, 2H), 1.70 (m, 2H), 1.57 (m, 2H); MS (ESI) m/z 340.0 [M+1]$^+$.

H. 7-(5-Fluoro-2-methyl-4-(1-(tetrahydro-2H-pyran-2-yl)-1H-1,2,4-triazol-3-yl)phenyl)-1-isopropyl-3,4-dihydropyrazino[2,3-b]pyrazin-2(1H)-one. 1-Isopropyl-7-(trimethylstannyl)-3,4-dihydropyrazino[2,3-b]pyrazin-2(1H)-one (300 mg, 0.84 mmol), 3-(4-bromo-2-fluoro-5-methylphenyl)-1-(tetrahydro-2H-pyran-2-yl)-1H-1,2,4-triazole (428 mg, 1.26 mmol) and bis(triphenylphosphine)palladium(II) dichloride (56 mg, 0.08 mmol) were combined in N,N-dimethylformamide (5 mL). The mixture was degassed and heated at 140° C. under nitrogen for 3 h. After being cooled to room temperature, the reaction mixture was filtered and the filtrate was partitioned between ethyl acetate (15 mL) and water (15 mL). The organic layer was separated and the aqueous layer was extracted with ethyl acetate (10 mL×2). The combined organic layer was dried over sodium sulfate, filtered, concentrated under reduced pressure and purified by preparative TLC (15% methanol in dichloromethane) to give the title compound (200 mg, yield 52%) as a solid.

I. 7-(5-Fluoro-2-methyl-4-(1H-1,2,4-triazol-3-yl)phenyl)-1-isopropyl-3,4-dihydropyrazino[2,3-b]pyrazin-2(1H)-one. A solution of 7-(5-fluoro-2-methyl-4-(1-(tetrahydro-2H-pyran-2-yl)-1H-1,2,4-triazol-3-yl)phenyl)-1-isopropyl-3,4-dihydropyrazino[2,3-b]pyrazin-2(1H)-one (200 mg, 0.44 mmol) in methanolic hydrochloride solution (20 mL, 2 M) was stirred for 5 h at room temperature. The reaction was diluted with saturated aqueous sodium bicarbonate solution (25 mL) and the aqueous mixture was extracted with ethyl acetate (25 mL×2). The organic phase was dried over sodium sulfate, filtered, evaporated under reduced pressure and purified on silica gel column (50-100% ethyl acetate in petroleum ether). The desired fractions were combined and concentrated under reduced pressure to give the title compound (75 mg, 46% yield). $^1$H NMR (DMSO-d$_6$, 400 MHz): δ (ppm) 14.25 (br. s., 1H), 8.20 (br. s., 1H), 7.90 (m, 2H), 7.58 (s, 1H), 7.35 (s, 1H), 5.24 (m, 1H), 4.10 (s, 2H), 2.43 (s, 3H), 1.44 (d, J=7.2, 6H); MS (ESI) m/z 368.2 [M+1]$^+$.

Example 8

7'-(2-Methyl-4-(4H-1,2,4-triazol-3-yl)phenyl)-1'H-spiro[cyclopropane-1,2'-pyrazino[2,3-b]pyrazin]-3'(4'H)-one

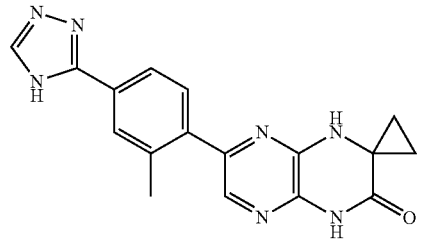 [SMILES: Cc1cc(-c2nnc[nH]2)ccc1-c1cnc2c(n1)NC1(CC1)C(=O)N2]

A. tert-Butyl 1-(3,5-dibromopyrazin-2-ylcarbamoyl)cyclopropyl-carbamate. 1,1'-Carbonyldiimidazole (4.37 g, 27.0 mmol) was added to a stirred solution of 1-(tert-butoxycarbonylamino)cyclopropanecarboxylic acid (4.93 g, 24.50 mmol) in N,N-dimethylformamide (6 mL) and dichloromethane (12 mL) at room temperature. The resulting clear yellow mixture was stirred at room temperature under nitrogen for 4 h. N,N-Diisopropylethylamine (8.54 mL, 49.0 mmol) was added followed by 3,5-dibromopyrazin-2-amine (9.29 g, 36.8 mmol). The resulting mixture was heated at 50° C. under a reflux condenser under nitrogen for 60 h. The resulting mixture was diluted with ethyl acetate and washed with water. The layers were separated and the organic layer washed with brine, dried over magnesium sulfate, filtered and concentrated under reduced pressure. The residue was taken up in dichloromethane and purified using flash chromatography (Biotage) (5-60% ethyl acetate in hexane). Fractions containing the desired product were combined and concentrated under reduced pressure. The residue was triturated with 15% ethyl acetate in hexane and dried under high vacuum to give the desired product (5.349 g, 12.27 mmol, 50% yield) as an off-white solid. $^1$H NMR (400 MHz, DMSO-d$_6$) δ (ppm) 9.92 (br. s., 1H), 8.76 (s, 1H), 7.70 (br. s., 1H), 1.41 (s, 9H), 1.34-1.40 (m, 2H), 1.02-1.09 (m, 2H); MS (ESI) m/z 437.3 [M+1]$^+$, 459.1 [M+Na]$^+$.

B. 1-Amino-N-(3,5-dibromopyrazin-2-yl)cyclopropanecarboxamide bistrifluoroacetate. TFA (6.02 mL, 78 mmol) was added to a stirred mixture of tert-butyl 1-(3,5-dibromopyrazin-2-ylcarbamoyl)cyclopropylcarbamate (3.410 g, 7.82 mmol) in dichloromethane (20 mL). The resulting clear yellow solution was stirred at room temperature for 4 h. All volatiles were removed under reduced pressure and the residue dried under high vacuum at 40° C. to give the desired product (4.42 g, 7.85 mmol, 100% yield) as a waxy yellow solid. MS (ESI) m/z 337.1 [M+1]$^+$.

C. 7'-Bromo-1'H-spiro[cyclopropane-1,2'-pyrazino[2,3-b]pyrazin]-3'(4'H)-one. 1-Amino-N-(3,5-dibromopyrazin-2- yl)cyclopropanecarboxamide bistrifluoroacetate (0.394 g, 0.700 mmol), N,N-diisopropylethylamine (0.610 mL, 3.50 mmol) and 1,4-dioxane (6 mL) were combined in a sealable vessel with a stirbar. The system was purged with nitrogen. The resulting mixture was sealed, stirred vigorously and heated at 110° C. for 2 h. Volatiles were removed under reduced pressure. The residue was dissolved in DMSO and methanol, filtered and purified using reverse-phase preparatory HPLC (10-65% acetonitrile+0.1% TFA in water+0.1% TFA, over 30 min). Fractions containing the desired product were combined, neutralized with saturated aqueous sodium bicarbonate and most of the solvent removed under reduced pressure. Solids were collected by vacuum filtration, washed thoroughly with water and dried under high vacuum to give the desired product (0.141 g, 0.553 mmol, 79% yield) as a light yellow solid. $^1$H NMR (400 MHz, DMSO-d$_6$) δ (ppm) 11.27 (s, 1H), 8.04 (s, 1H), 7.46 (s, 1H), 1.29-1.38 (m, 2H), 0.91-1.01 (m, 2H); MS (ESI) m/z 255.1 [M]$^+$, 257.0 [M+2]$^+$.

D. 7'-(2-Methyl-4-(4-(tetrahydro-2H-pyran-2-yl)-4H-1,2,4-triazol-3-yl)phenyl)-1'H-spiro[cyclopropane-1,2'-pyrazino[2,3-b]pyrazin]-3'(4'H)-one Trifluoroacetate. 3-(3-Methyl-4-(4,4,5,5-tetramethyl-1,3,2-dioxaborolan-2-yl)phenyl)-4-(tetrahydro-2H-pyran-2-yl)-4H-1,2,4-triazole (See Example 2. C) (0.201 g, 0.545 mmol), 7'-bromo-1'H-spiro[cyclopropane-1,2'-pyrazino[2,3-b]pyrazin]-3'(4'H)-one (0.139 g, 0.545 mmol), [1,1'-bis(diphenylphosphino)ferrocene]dichloropalladium(II), complex with dichloromethane (1:1) (0.045 g, 0.054 mmol), sodium carbonate (1 M in water, 1.635 mL, 1.635 mmol), 1,4-dioxane (1.2 mL) and isopropanol (0.4 mL) were combined in a sealable vessel with a stirbar. The system was purged with nitrogen. The resulting mixture was sealed, stirred vigorously and heated at 100° C. for 1 h. The resulting mixture was diluted with water and extracted three times with dichloromethane. The combined organics were concentrated under reduced pressure. The residue was taken up in DMSO and methanol, filtered and purified using reverse-phase preparatory HPLC (20-70% acetonitrile+0.1% TFA in water+0.1% TFA, over 30 min). Fractions containing the desired product were combined and the solvent removed under reduced pressure. The residue was dried under high vacuum to give the desired product (0.109 g, 0.205 mmol, 38% yield) as an orange solid. MS (ESI) m/z 418.4 [M+1]$^+$.

E. 7'-(2-Methyl-4-(4H-1,2,4-triazol-3-yl)phenyl)-1'H-spiro[cyclopropane-1,2'-pyrazino[2,3-b]pyrazin]-3'(4'H)-one. 6 N Hydrochloric acid in water (0.171 mL, 1.025 mmol) was added to a stirred mixture of 7'-(2-methyl-4-(4-(tetrahydro-2H-pyran-2-yl)-4H-1,2,4-triazol-3-yl)phenyl)-1'H-spiro[cyclopropane-1,2'-pyrazino[2,3-b]pyrazin]-3'(4'H)-one trifluoroacetate (0.109 g, 0.205 mmol) in ethanol (4 mL) at 80° C. The resulting mixture was stirred vigorously and heated at 80° C. under a reflux condenser under nitrogen for 30 min. The resulting mixture was filtered and purified using reverse-phase preparatory HPLC (10-60% acetonitrile+0.1% TFA in water+0.1% TFA, over 30 min). Fractions containing the desired product were combined, neutralized with saturated aqueous sodium bicarbonate and most of the solvent removed under reduced pressure. Solids were collected by vacuum filtration, washed thoroughly with water and dried under high vacuum at 45° C. to give the desired product (0.027 g, 0.079 mmol, 39% yield) as a yellow solid. $^1$H NMR (400 MHz, DMSO-d$_6$) δ (ppm) 11.22 (br. s., 1H), 8.63 (br. s., 1H), 7.93 (s, 1H), 7.89 (d, J=7.81 Hz, 1H), 7.62 (s, 1H), 7.58 (s, 1H), 7.47 (br. s., 1H), 2.43 (s, 3H), 1.29-1.38 (m, 2H), 0.95-1.04 (m, 2H); MS (ESI) m/z 334.2 [M+1]$^+$.

Example 9

7-(6-(2-Hydroxypropan-2-yl)pyridin-3-yl)-1-((trans)-4-methoxycyclohexyl)-3,4-dihydropyrazino[2,3-b]pyrazin-2(1H)-one

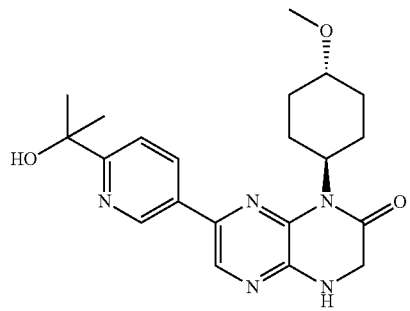 [SMILES: CO[C@H]1CC[C@H](N2C(=O)CNc3ncc(-c4ccc(C(C)(C)O)nc4)nc32)CC1]

A. Ethyl 2-(5-bromo-3-(trans-4-methoxycyclohexylamino)pyrazin-2-ylamino) acetate. Ethyl 2-(3,5-dibromopyrazin-2-ylamino)acetate (See Example 6.B) (30.0 g, 88 mmol), trans-4-methoxycyclohexanamine (17.15 g, 133 mmol), N,N-diisopropylethylamine (30.8 mL, 177 mmol) and dimethylsulfoxide (70.8 mL) were combined in a reaction vial with a stirbar and heated in an oil bath at 150° C. for 16 h with stirring. The resulting mixture was diluted with ethyl acetate and the volatiles removed under reduced pressure. The residue was purified using silica gel chromatography on a Biotage SP1 (12% ethyl acetate in hexanes). Fractions containing the desired product were combined and organic volatiles removed under reduced pressure. The residue was triturated with 5% ethyl acetate in hexane. Solids were collected by vacuum filtration, washed with hexane and dried under vacuum to afford ethyl the title compound (15.37 g, 39.7 mmol, 44.8% yield) as an off-white solid. MS (ESI) m/z 387.0 [M]$^+$, 389.0 [M+2]$^+$.

B. 7-Bromo-1-(trans-4-methoxycyclohexyl)-3,4-dihydropyrazino[2,3-b]pyrazin-2(1H)-one. The following reaction was split into 3 separate sealed tubes and worked up separately. The material was then combined following purification. Ethyl 2-(5-bromo-3-(trans-4-methoxycyclohexylamino)pyrazin-2-ylamino)acetate (10 g, 25.7 mmol), methanol (10.5 mL, 259 mmol) and TFA (100 mL) were combined in a sealable vessel with a stirbar. The system was purged with nitrogen and the resulting mixture was sealed, stirred vigorously and heated at 90° C. with an oil bath for 18.5 h. The resulting mixture was diluted with methanol and all the solvent was removed under reduced pressure. Methanol (100 mL) was added and all the solvent was removed under reduced pressure again. Methanol (100 mL) and sodium bicarbonate (12.4 g, 147 mmol) were added. The resulting mixture was stirred at room temperature until pH=6 (in water). The mixture was concentrated nearly to dryness. Water (100 mL) was added. The resulting brown solids were collected by vacuum filtration and washed with water. The brown solids were dissolved in hot methanol and acetonitrile and purified using reverse-phase C18 flash column chromatography (20-100% acetonitrile in water). Fractions containing the desired product were combined and concentrated nearly to dryness under reduced pressure. Solids were collected by vacuum filtration, washed with water and dried under high vacuum to give the desired product (4.88 g, 14.3 mmol, 55% yield) as a light tan solid. $^1$H NMR (400 MHz, DMSO-d$_6$) δ (ppm) 7.71 (s, 1H), 7.59 (s, 1H), 4.66 (tt, J=3.61, 12.20 Hz, 1H), 4.07 (d, J=1.56 Hz, 2H), 3.25 (s, 3H), 3.06-3.17 (m, 1H), 2.42 (qd, J=3.51, 12.89 Hz, 2H), 2.10 (d, J=10.93 Hz, 2H), 1.61 (d, J=10.93 Hz, 2H), 1.10-1.24 (m, 2H); MS (ESI) m/z 341.3 [M]$^+$, 343.1 [M+2]$^+$.

C. 7-(6-(2-Hydroxypropan-2-yl)pyridin-3-yl)-1-(trans-4-methoxycyclohexyl)-3,4-dihydropyrazino[2,3-b]pyrazin-2(1H)-one. 2-(5-(Trimethylstannyl)pyridin-2-yl)propan-2-ol (See Example 5.E) (9.43 g, 31.4 mmol), 7-bromo-1-(trans-4-methoxycyclohexyl)-3,4-dihydropyrazino[2,3-b]pyrazin-2(1H)-one (10.02 g, 29.4 mmol), [1,1'-bis(diphenyl-phosphino)-ferrocene]dichloropalladium(II) dichloromethane adduct (2.398 g, 2.94 mmol) and N,N-dimethylformamide (25 mL) were combined in a round-bottom flask with a stir-bar. The atmosphere in the vessel was removed under vacuum and replaced with nitrogen gas three times. The resulting mixture was stirred vigorously and heated at 120° C. under nitrogen for 35 min. The resulting mixture was purified using flash chromatography, split into 4 separate columns, (2-15% methanol in dichloromethane). Fractions containing the desired product were combined and most of the solvent removed under reduced pressure. The resulting mixture was purified using reverse-phase preparatory HPLC (20-40% acetonitrile+0.1% TFA in water+0.1% TFA, over 30 min), split into 6 runs. Fractions containing the desired product were combined and all of the acetonitrile and some of the water were removed under reduced pressure at 25° C. The remaining yellow solution was loaded onto 50 g of Strata X-C ion exchange resin from Phenomenex. The column was washed successively with water, acetonitrile, methanol and then 5% ammonium hydroxide in methanol. The product eluted with the 5% ammonium hydroxide in methanol wash and was concentrated under reduced pressure and dried under high vacuum to give the desired product (4.85 g, 12.20 mmol, 42% yield) as a pink foam-solid. $^1$H NMR (400 MHz, DMSO-d$_6$) δ (ppm) 9.03 (d, J=1.56 Hz, 1H), 8.28 (s, 1H), 8.24 (dd, J=2.34, 8.20 Hz, 1H), 7.74 (d, J=7.81 Hz, 1H), 7.61 (s, 1H), 5.26 (s, 1H), 4.90 (tt, J=3.71, 12.10 Hz, 1H), 4.13 (s, 2H), 3.28 (s, 3H), 3.20 (tt, J=4.00, 10.84 Hz, 1H), 2.58 (qd, J=2.93, 12.82 Hz, 2H), 2.14 (d, J=10.15 Hz, 2H), 1.68 (d, J=10.93 Hz, 2H), 1.47 (s, 6H), 1.17-1.35 (m, 2H); MS (ESI) m/z 398.3 [M+1]$^+$; mp 196-198° C. (uncorrected).

D. 7-(6-(2-Hydroxypropan-2-yl)pyridin-3-yl)-1-(trans-4-methoxycyclohexyl)-3,4-dihydropyrazino[2,3-b]pyrazin-2(1H)-one (Alternate Approach). Ethyl 2-(3,5-dibromopyrazin-2-ylamino)acetate (1 equiv) and trans-4-methoxycyclohexanamine hydrochloride (1.5 equiv), NMP and DIPEA were combined and heated to 127° C. and maintained at that temperature for 18 h. Upon reaction completion, the mixture was cooled to 35° C. over 4 h. The solution was transferred to a mixture of ethyl acetate and 5% brine. The aqueous layer was removed and the organic layer was washed successively with 5% brine and water. The organic layer was concentrated by vacuum distillation to a low volume, cooled to ambient temperature and the solids were collected by vacuum filtration. The solids were washed with MTBE and the product was dried in a vacuum oven to give 41% yield of ethyl 2-(5-bromo-3-(trans-4-methoxycyclohexylamino)pyrazin-2-ylamino)acetate. A mixture of ethyl 2-(5-bromo-3-(trans-4-methoxycyclohexylamino)pyrazin-2-ylamino) acetate (1 equiv), water and 85% phosphoric acid (3:1) was heated to 80° C. over 1 h. Heating was maintained for 18 h to effect reaction completion. Upon reaction completion, the mixture was cooled to 25° C. and filtered to give a crude product as tan solid. The resulting solids were washed with water, slurried in water and filtered. The solids were washed with water until the pH of the filtrate was between 4 and 8. The resulting material was dried under vacuum to give 89% yield of 7-bromo-1-(trans-4-methoxycyclohexyl)-3,4-dihydropyrazino[2,3-b]pyrazin-2(1H)-one. 7-Bromo-1-(trans-4-methoxycyclohexyl)-3,4-dihydropyrazino[2,3-b]pyrazin-2(1H)-one (1 equiv), 5-(4,4,5,5-tetramethyl-1,3,2-dioxaborolan-2-yl)-2-(2-(trimethylsilyloxy)propan-2-yl)pyridine (1 equiv), sodium carbonate (3 equiv) and PdCl$_2$(AmPhos)$_2$ (0.003 equiv) were combined in isopropanol and heated at 70° C. for 1.5 h. Standard work-up and purification afforded the protected compound in 93% yield. Deprotection using standard conditions for removal of a trimethylsilyl-group and isolation gave the title compound.

Alternatively, ethyl 2-(3,5-dibromopyrazin-2-ylamino)acetate (1 equiv) and trans-4-methoxycyclohexanamine hydrochloride (1.5 equiv), NMP and DIPEA were combined and heated to 125° C. and maintained at that temperature for 18 h. Upon reaction completion, the mixture was cooled to room temperature and transferred to a mixture of ethyl acetate and aqueous sodium chloride. The aqueous layer was removed and the organic layer was washed successively with aqueous sodium chloride and water. The organic layer was concentrated by vacuum distillation to a low volume, cooled to ambient temperature and the solids were collected and dried to give ethyl 2-(5-bromo-3-(trans-4-methoxycyclohexylamino)pyrazin-2-ylamino)acetate. A mixture of ethyl 2-(5-bromo-3-(trans-4-methoxycyclohexylamino)pyrazin-2-ylamino) acetate (1 equiv), water (161 equiv) and 85% phosphoric acid (16.5 equiv) was heated at 80° C. Upon reaction completion, the mixture was cooled to 25° C., filtered and the solids were washed with water. The solids were resuspended in water and the filtration and wash were repeated. The resulting material was dried to give 7-bromo-1-(trans-4-methoxycyclohexyl)-3,4-dihydropyrazino[2,3-b]pyrazin-2(1H)-one. 7-Bromo-1-(trans-4-methoxycyclohexyl)-3,4-dihydropyrazino[2,3-b]pyrazin-2(1H)-one (1 equiv), 2-(5-(4,4,5,5-tetramethyl-1,3,2-dioxaborolan-2-yl)pyridin-2-yl)propan-2-ol (1.08 equiv) and PdCl$_2$(AmPhos)$_2$ (0.0025 equiv) were combined in tetrahydrofuran. The mixture was treated with a solution of potassium carbonate (2.5 equiv) and heated to reflux. After cooling to 40° C., toluene was added, and the layers were separated. The organic layer was washed with potassium dihydrogenphosphate solution and treated with a metal scavenger (SiliaBond® Thiol). The mixture was filtered and distilled with the addition of toluene until the temperature reached 100° C. Upon cooling the resulting solids were collected by filtration and dried. The solid was combined with butylated hydroxyl toluene (BHT) (9×10$^{-4}$ equiv) in IPA and water (3×:5× vol). The mixture was heated to 65° C. and while maintaining this temperature, water (5× vol) was added. A small amount of the title compound (0.02 equiv) in water was added. The mixture was allowed to stand for 2 h, cooled to room temperature and stirred. The resulting solids were collected by filtration and dried to give 7-(6-(2-hydroxypropan-2-yl)pyridin-3-yl)-1-(trans-4-methoxycyclohexyl)-3,4-dihydropyrazino[2,3-b]pyrazin-2(1H)-one as an off-white solid.

Example 10

9-(6-(4H-1,2,4-Triazol-3-yl)-2-methyl-3-pyridyl)-6,11,4a-trihydromorpholino[4,3-e]pyrazino[2,3-b]pyrazin-5-one

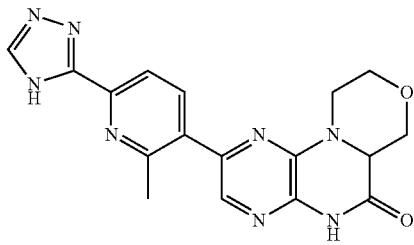 [SMILES: Cc1nc(-c2nnc[nH]2)ccc1-c1cnc2c(n1)N1CCOCC1C(=O)N2]

A. 5-Bromo-6-methylpicolinonitrile. 3,6-Dibromo-2-methylpyridine (4.9 g, 19.53 mmol), copper(I)cyanide (1.75 g, 19.53 mmol) and N,N-dimethylformamide (20 mL) were combined in a sealable vessel with a stirbar. The resulting mixture was sealed, stirred vigorously and heated at 110° C. for 4 h. The resulting mixture was diluted with ethyl acetate, poured into a reparatory funnel containing water and the layers were separated. The water layer was extracted with ethyl acetate twice. The combined organics were washed with brine, dried over magnesium sulfate, filtered and concentrated under reduced pressure. The resulting solid was purified by silica gel chromatography (10% ethyl acetate in hexanes) to give the title compound as a white solid (1.88 g, 9.54 mmol, 49% yield). MS (ESI) m/z 197.3 [M]+.

B. tert-Butyl 3-(3,5-dibromopyrazin-2-ylcarbamoyl)morpholine-4-carboxylate. A solution of 4-(tert-butoxycarbonyl)morpholine-3-carboxylic acid (1.500 g, 6.49 mmol) and 1,1'-carbonyldiimidazole (1.578 g, 9.73 mmol) in N,N-dimethylformamide (2 mL) and dichloromethane (6 mL) was stirred 4.5 h at room temperature under nitrogen. N,N-Diisopropylethylamine (2.260 mL, 12.97 mmol) was added followed by 3,5-dibromopyrazin-2-amine (3.28 g, 12.97 mmol). The resulting mixture was stirred and heated at 50° C. under a reflux condenser under nitrogen for 2 d. The resulting mixture was concentrated under reduced pressure. The residue was diluted with water and extracted 3 times with ethyl acetate. The combined organics were washed with water and brine, dried over magnesium sulfate, filtered and concentrated under reduced pressure. The residue was purified using flash chromatography (20-30-50% ethyl acetate in hexanes) to give the desired product (2.136 g, 4.58 mmol, 71% yield) as a slightly yellow foam-solid. MS (ESI) m/z 467 [M+1]+.

C. 9-Bromo-6,11,4a-trihydromorpholino[4,3-e]pyrazino[2,3-b]pyrazin-5-one. tert-Butyl 3-(3,5-dibromopyrazin-2-ylcarbamoyl)morpholine-4-carboxylate (2.132 g, 4.57 mmol) was dissolved in dichloromethane (45 mL) with stirring at room temperature. TFA (9 mL) was added and the resulting light yellow mixture was capped and stirred at room temperature for 2.5 h. The solvent was removed under reduced pressure and the residue dried under high vacuum at 45° C. to give a viscous yellow oil. The yellow oil was dissolved in isopropanol (wet) (50 mL) with stirring at room temperature. Sodium bicarbonate (3.84 g, 45.7 mmol), palladium(II) acetate (0.103 g, 0.457 mmol) and 4,5-bis(diphenylphosphino)-9,9-dimethylxanthene (0.239 mL, 1.372 mmol) were added. The atmosphere in the flask was removed and replaced with nitrogen. The resulting mixture was stirred vigorously and heated at 80° C. under a reflux condenser under nitrogen for 2 h. The resulting mixture was cooled to room temperature and diluted with water (30 mL). The resulting solids were collected by vacuum filtration, washed thoroughly with water and diethyl ether and dried under high vacuum to give the desired product at ~90% purity (1.441 g, 5.05 mmol, 99% yield) as a yellow solid. MS (ESI) m/z 285 [M]+, 287 [M+2]+.

D. 9-(1,1-Dimethyl-1-stannaethyl)-6,11,4a-trihydromorpholino[4,3-e]pyrazino[2,3-b]pyrazin-5-one. 9-Bromo-6,11,4a-trihydromorpholino[4,3-e]pyrazino[2,3-b]pyrazin-5-one (0.30 g, 1.052 mmol), hexamethylditin (0.414 g, 1.263 mmol), tetrakis(triphenylphosphine)palladium (0) (0.122 g, 0.105 mmol) and 1,4-dioxane (5 mL) were combined in a sealable vessel with a stirbar. Nitrogen gas was bubbled through the solution for five min. The vessel was sealed, stirred vigorously and heated at 100° C. for 2 h. The resulting cloudy black mixture was diluted with ethyl acetate, filtered and the filter cake washed thoroughly with ethyl acetate. The filtrate was concentrated under reduced pressure and purified using Biotage flash chromatography (20-80% ethyl acetate in hexanes) to give the desired product (0.350 g, 0.948 mmol, 90% yield) as a yellow-white solid. MS (ESI) m/z 369.5 [M]+.

E. 6-Methyl-5-(5-oxo(6,11,4a-trihydromorpholino[4,3-e]pyrazino[2,3-b]pyrazin-9-yl))pyridine-2-carbonitrile. 5-Bromo-6-methylpicolinonitrile (0.080 g, 0.406 mmol), 9-(1,1-dimethyl-1-stannaethyl)-6,11,4a-trihydromorpholino[4,3-e]pyrazino[2,3-b]pyrazin-5-one (0.150 g, 0.406 mmol), tris(dibenzylideneacetone)dipalladium(0) (0.041 g, 0.045 mmol), tri-o-tolylphosphine (0.027 g, 0.089 mmol) and triethylamine (0.170 mL, 1.219 mmol) were placed in a sealed tube and N,N-dimethylformamide (2 mL) was added. Nitrogen gas was bubbled through the reaction mixture for five minutes and the reaction sealed and heated at 100° C. for 1 h. The resulting cloudy black mixture was diluted with methanol, filtered and the filter cake washed thoroughly with methanol. The filtrate was concentrated under reduced pressure and purified using Biotage flash chromatography (50-100% ethyl acetate in hexanes) to give the desired product (0.117 g, 0.363 mmol, 89% yield). MS (ESI) m/z 323.5 [M+1]+

F. 6-Methyl-5-(5-oxo(6,11,4a-trihydromorpholino[4,3-e]pyrazino[2,3-b]pyrazin-9-yl))pyridine-2-carboxamide. 6-Methyl-5-(5-oxo(6,11,4a-trihydromorpholino[4,3-e]pyrazino[2,3-b]pyrazin-9-yl))pyridine-2-carbonitrile (0.18 g, 0.558 mmol) was placed in a round bottom flask and while stirring, a mixture of TFA (1.6 mL) and sulfuric acid (0.4 mL) was added. The resulting suspension was allowed to stir for 16 h at room temperature. The mixture was poured over ice and the excess acid was carefully neutralized with solid potassium hydroxide. The solid obtained was filtered, washed with water and dried under high vacuum to yield the title compound (0.153 g, 0.450 mmol, 81% yield) as a red solid. MS (ESI) m/z 341.5 [M+1]+

G. 9-(6-(4H-1,2,4-Triazol-3-yl)-2-methyl-3-pyridyl)-6,11,4a-trihydromorpholino[4,3-e]pyrazino[2,3-b]pyrazin-5-one. 6-Methyl-5-(5-oxo(6,11,4a-trihydromorpholino[4,3-e]pyrazino[2,3-b]pyrazin-9-yl))pyridine-2-carboxamide (0.159 g, 0.467 mmol), N,N-dimethylformamide dineopentyl acetal (2 mL, 8.85 mmol) and dimethylsulfoxide (0.5 mL) were placed in a flask and heated to 85° C. for 1 h. The solution was diluted with acetic acid (5 mL, 87 mmol) and hydrazine (0.468 mL, 14.90 mmol) was added dropwise. The reaction was allowed to stir at 25° C. for 30 min. The mixture was concentrated under reduced pressure and the residue was carefully neutralized with a saturated aqueous sodium carbonate solution. This solution then was extracted with ethyl acetate three times, concentrated under reduced pressure and purified using reverse-phase semi-preparatory HPLC (5-50% acetonitrile+0.1% TFA in water+0.1% TFA, over 20 min) to afford the title compound (0.03 g, 0.082 mmol, 17.63% yield). $^1$H NMR (400 MHz, DMSO-$d_6$) δ (ppm) 7.96-8.04 (m, 2H), 7.88 (s, 1H), 4.33 (dd, J=3.71, 10.74 Hz, 1H), 4.15-4.23 (m, 2H), 3.98 (dd, J=3.51, 11.71 Hz, 1H), 3.51-3.63 (m, 2H), 2.89-2.99 (m, 1H), 2.70 (s, 3H); MS (ESI) m/z 365.5 [M+1]$^+$ Example 11

6-(6-(1H-1,2,4-Triazol-3-yl)pyridin-3-yl)-4-(tetrahydro-2h-pyran-4-yl)-3,4-dihydropyrazino[2,3-b]pyrazin-2(1H)-one

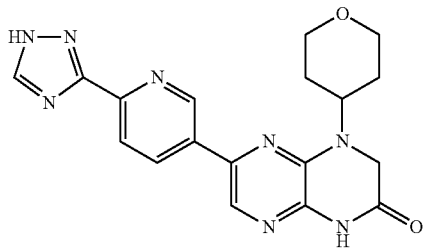 [SMILES: O=C1CN(C2CCOCC2)c2nc(-c3ccc(-c4nc[nH]n4)nc3)cnc2N1]

A. 6-Bromo-4-(tetrahydro-2H-pyran-4-yl)-3,4-dihydropyrazino[2,3-b]pyrazin-2(1H)-one. To a solution of N-(3,5-dibromopyrazin-2-yl)-2-iodoacetamide (See Example 5.B) (6.6 g, 15.8 mmol) and diisopropylethylamine (4.0 g, 31.6 mmol) in acetonitrile (50 mL) was added tetrahydro-2H-pyran-4-amine (6.4 g, 63.2 mmol) and the mixture was stirred at ambient temperature for 16 h. The solvent was removed under reduced pressure and the residue which was purified by chromatography on silica gel (5-20% ethyl acetate in petroleum ether) to give the title compound (1.98 g, 40% yield). MS (ESI) m/z 313.1 [M+1]$^+$.

B. 4-(Tetrahydro-2H-pyran-4-yl)-6-(trimethylstannyl)-3,4-dihydropyrazino[2,3-b]pyrazin-2(1H)-one. A degassed mixture of 6-bromo-4-(tetrahydro-2H-pyran-4-yl)-3,4-dihydropyrazino[2,3-b]pyrazin-2(1H)-one (1.98 g, 6.35 mmol), tetrakis(triphenylphosphine)palladium (1.45 g, 1.27 mmol) and hexamethylditin (4.0 g, 12.7 mmol) in dioxane (10 mL) was heated at 90° C. for 3 h under nitrogen. The reaction mixture was concentrated under reduced pressure and purified on silica gel column (10-20% ethyl acetate in petroleum ether) to afford the product (1.07 g, 42.3% yield). MS (ESI) m/z 399.1[M+1]$^+$.

C. 6-(6-(1-(Tetrahydro-2H-pyran-2-yl)-1H-1,2,4-triazol-3-yl)pyridin-3-yl)-4-(tetrahydro-2H-pyran-4-yl)-3,4-dihydropyrazino[2,3-b]pyrazin-2(1H)-one. A mixture of 4-(tetrahydro-2H-pyran-4-yl)-6-(trimethylstannyl)-3,4-dihydropyrazino[2,3-b]pyrazin-2(1H)-one (1 equiv), 5-bromo-2-(1-(tetrahydro-2H-pyran-2-yl)-1H-1,2,4-triazol-3-yl)pyridine (1.2 equiv), tris(dibenzylideneacetone)dipalladium (0.1 equiv), tri-o-tolylphosphine (0.2 equiv), triethylamine (3 equiv) and N,N-dimethylformamide was heated at 95° C. for 3 h under nitrogen. Concentration and chromatography purification give the desired product in 39% yield. MS (ESI) m/z 463.1 [M+1]$^+$.

D. 6-(6-(1H-1,2,4-Triazol-3-yl)pyridin-3-yl)-4-(tetrahydro-2H-pyran-4-yl)-3,4-dihydro pyrazino[2,3-b]pyrazin-2(1H)-one. A mixture of 6-(6-(1-(tetrahydro-2H-pyran-2-yl)-1H-1,2,4-triazol-3-yl)pyridin-3-yl)-4-(tetrahydro-2H-pyran-4-yl)-3,4-dihydropyrazino[2,3-b]pyrazin-2(1H)-one in methanolic hydrochloride solution was stirred at room temperature for 0.5 h. The solvent was evaporated under reduced pressure to give the crude product, which was washed with N,N-dimethylformamide to afford the title compound as a hydrochloride salt in 34% yield. $^1$H NMR (DMSO-$d_6$, 400 MHz) δ (ppm) 11.44 (s, 1H), 9.30 (s, 1H), 8.59 (d, J=8.4 Hz, 1H), 8.46 (s, 1H), 8.22 (m, 2H), 4.70 (t, J=10 Hz, 1H), 4.16 (s, 1H), 3.99 (m, 4H), 3.51 (t, J=11.2 Hz, 2H), 1.86 (m, 2H), 1.69 (d, J=12.8 Hz, 2H); MS (ESI) m/z 379.1 [M+1]$^+$.

Example 12

1-Ethyl-7-(2-methyl-6-(4H-1,2,4-triazol-3-yl)pyridin-3-yl)-3,4-dihydropyrazino[2,3-b]pyrazin-2(1H)-one

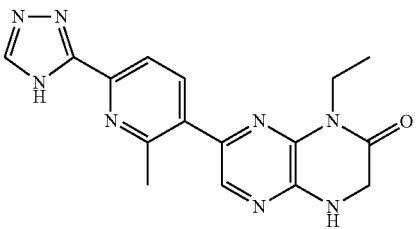 [SMILES: CCN1C(=O)CNc2ncc(-c3ccc(-c4nnc[nH]4)nc3C)nc21]

A. 7-Bromo-1-ethyl-3,4-dihydropyrazino[2,3-b]pyrazin-2(1H)-one. A mixture of ethyl 2-(3,5-dibromopyrazin-2-ylamino)acetate (See Example 6.B) (1 equiv), ethylamine hydrochloride (3.1 equiv), N,N-diisopropylethylamine (4 equiv) in N-methyl pyrrolidinone was heated at 105° C. under nitrogen for 14 h. Standard ethyl acetate/water work up gave the crude product in 77% yield. This material was used without further purification. Crude ethyl 2-(5-bromo-3-(ethylamino)pyrazin-2-ylamino)acetate and acetic acid were combined in methanol. The reaction mixture was refluxed at 60-62° C. under nitrogen for 16 h. The reaction was concentrated under reduced pressure and the resultant residue was diluted with methanol and concentrated. The resultant residue was dissolved in ethyl acetate treated with sodium carbonate and stirred for 10 min until pH ~7. The mixture was filtered and washed with ethyl acetate. The filtrate was concentrated and purification by a silica gel plug purification using (0-40% ethyl acetate in hexanes) gave the product as a tan solid. Additionally the filter-cake was suspended in water to remove potassium carbonate. The remaining solid product was collected by filtration. The process afforded product in a combined yield of 75%.

B. 1-Ethyl-7-(2-methyl-6-(4H-1,2,4-triazol-3-yl)pyridin-3-yl)-3,4-dihydropyrazino[2,3-b]pyrazin-2(1H)-one. A mixture of 3-bromo-2-methyl-6-(1-(tetrahydro-2H-pyran-2-yl)-1H-1,2,4-triazol-3-yl)pyridine (1 equiv), bis(pinacolato)diboron (1.05 equiv), potassium acetate (2 equiv), potassium carbonate (3 equiv), [1,1'-bis(diphenylphosphino)-ferrocene]dichloropalladium(II), complex with dichloromethane (1:1) (0.1 equiv) in anhydrous dioxane (300 mL) was degassed and heated at 90° C. for 2 h. The mixture was cooled to <40° C. and 7-bromo-1-ethyl-3,4-dihydropyrazino[2,3-b]pyrazin-2(1H)-one (1 equiv), water and [1,1'-bis(diphenylphosphino)-ferrocene]dichloropalladium(II), complex with dichloromethane (1:1) (0.05 equiv) were added. The mixture was degassed and heated at 65-70° C. under nitrogen for 1 h. The mixture was cooled to <40° C., diluted with water and ethyl acetate. Standard ethyl acetate/water work up followed by flash column chromatography (0-5% methanol in dichloromethane) and recrystallization from ethanol gave the title compound in 57% yield. $^1$H NMR (400 MHz, DMSO-d$_6$) δ (ppm) 7.99 (s, 2H), 7.93 (s, 1H), 7.72 (s, 1H), 4.22 (s, 2H), 4.05 (q, J=6.77 Hz, 2H), 2.71 (s, 3H), 1.18 (t, J=7.03 Hz, 3H); MS (ESI) m/z 337.6 [M+1]$^+$.

C. 1-Ethyl-7-(2-methyl-6-(4H-1,2,4-triazol-3-yl)pyridin-3-yl)-3,4-dihydropyrazino[2,3-b]pyrazin-2(1H)-one (Alternate Approach). Ethyl 2-(3,5-dibromopyrazin-2-ylamino)acetate (1 equiv), tetrahydrofuran and sodium hydroxide in water (1.1 equiv) were combined and stirred at room temperature overnight. The reaction mixture was filtered and the collected solids were dried to give sodium 2-(3,5-dibromopyrazin-2-ylamino)acetate as an off-white solid. Sodium 2-(3,5-dibromopyrazin-2-ylamino)acetate and ethylamine (3 equiv, 70 wt % solution) were combined in water and the mixture was stirred at 90° C. overnight. The reaction mixture was cooled to 80° C., treated with phosphoric acid (10 equiv), and stirred for 3 h. The mixture was cooled to room temperature and the solids were collected by filtration. The product was dried to obtain 7-bromo-1-ethyl-3,4-dihydropyrazino[2,3-b]pyrazin-2(1H)-one as a grey solid. 7-Bromo-1-ethyl-3,4-dihydropyrazino[2,3-b]pyrazin-2(1H)-one (1 equiv), bispinacoldiborane (1.5 equiv), and potassium acetate (3.2 equiv) were combined in tetrahydrofuran. The reaction was heated to reflux and PdCl$_2$(AmPhos)$_2$ (0.002 equiv) was added. After 4 h, the reaction was cooled to room temperature. The mixture was filtered and the collected solids were washed with tetrahydrofuran. The filtrate was concentrated under reduced pressure to 50% of the original volume and hexanes was added. The resulting solids were collected by filtration and dried to obtain 1-ethyl-7-(4,4,5,5-tetramethyl-1,3,2-dioxaborolan-2-yl)-3,4-dihydropyrazino[2,3-b]pyrazin-2(1H)-one as a tan solid. 1-Ethyl-7-(4,4,5,5-tetramethyl-1,3,2-dioxaborolan-2-yl)-3,4-dihydropyrazino[2,3-b]pyrazin-2(1H)-one (1 equiv) and 3-bromo-2-methyl-6-(1-(tetrahydro-2H-pyran-2-yl)-1H-1,2,4-triazol-3-yl)pyridine (0.96 eqiv), were combined in tetrahydrofuran. A solution of potassium carbonate (2 equiv) in water, was added to the flask with stirring. The solution was treated with PdCl$_2$(AmPhos)$_2$ (0.002 equiv) and heated to 65° C. for 1 h. The solution was treated with MTBE and seeded. Additional MTBE and seed were added before adding a final portion of MTBE to the reaction mixture. The solids were collected by filtration and dried to obtain the desired intermediate as a tan solid. This intermediate and reagent alcohol (95% ethanol and 5% isopropanol) were combined and the mixture was treated with concentrated aqueous hydrogen chloride and heated to 60° C. A second charge of concentrated aqueous hydrogen chloride was made and the material was heated for 2 h. The reaction mixture was cooled to room temperature and filtered. The solids were washed with IPA and dried to obtain 1-ethyl-7-(2-methyl-6-(4H-1,2,4-triazol-3-yl)pyridin-3-yl)-3,4-dihydropyrazino[2,3-b]pyrazin-2(1H)-one hydrochloride as a pale yellow solid. The salt was dissolved in water and tetrahydrofuran and treated with a metal scavenger (SiliaBond® Thiol) (10 wt %) overnight. The slurry was filtered and the solids rinsed with 1:1 tetrahydrofuran/water. The filtrate was treated with aqueous ammonium hydroxide solution concentrated under reduced pressure to 70% of its volume. The solution was cooled to room temperature and the resulting solids were filtered and washed with water and ethanol. The dried solids were transferred to a flask, treated with ethanol, and heated to 65° C. for 2 h. The mixture was cooled to room temperature and held overnight. The solids were collected by vacuum filtration and dried to obtain 1-ethyl-7-(2-methyl-6-(4H-1,2,4-triazol-3-yl)pyridin-3-yl)-3,4-dihydropyrazino[2,3-b]pyrazin-2(1H)-one as an off-white solid.

Example 13

4-((cis)-4-Methoxycyclohexyl)-6-(2-methyl-6-(4H-1,2,4-triazol-3-yl)pyridin-3-yl)-3,4-dihydropyrazino[2,3-b]pyrazin-2(1H)-one

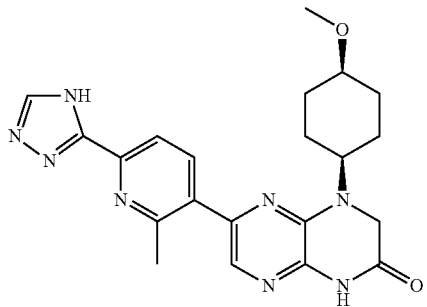 [SMILES: CO[C@H]1CC[C@@H](N2CC(=O)Nc3ncc(-c4ccc(-c5nnc[nH]5)nc4C)nc32)CC1]

A. 5-Bromo-6-methylpicolinamide. A solution of 5-bromo-6-methylpicolinonitrile (1.8 g, 9.14 mmol) in a mixture of TFA and sulfuric acid (30 mL, 4:1, V/V) was stirred at 40° C. for 16 h. The reaction mixture was poured into ice water. The resulting solid was filtered off and washed with water and dried to give the desired product as a white solid (1.0 g, 4.65 mmol, 54% yield). MS (ESI) m/z 217.1 [M+2]$^+$.

B. 3-Bromo-2-methyl-6-(1H-1,2,4-triazol-3-yl)pyridine. 5-Bromo-6-methylpicolinamide (1 g, 4.65 mmol) and N,N-dimethylformamide dimethylacetal (20 mL) were combined in a 100 mL round-bottom flask with a stir bar and heated at 85° C. under a reflux condenser under nitrogen for 3 h. The resulting mixture was concentrated under reduced pressure and dried under vacuum to give yellow oil, which was used in the next step without purification. The residue was diluted with acetic acid (10 mL) and hydrazine (2.5 mL, 70.3 mmol) was added drop-wise and allowed to stir at room temperature for 5 h. The reaction mixture was poured into ice water. The resulting solid was filtered, washed with water and dried to give the desired product as a white solid. The aqueous filtrate was extracted with dichloromethane. The organic layer was concentrated under reduced pressure nearly to dryness to yield additional material. Combination of two batches gave the desired product (0.7 g, 2.9 mmol, 63% yield). MS (ESI) m/z 241.1 [M+2]$^+$. Alternate approach: 5-Bromo-6-methylpicolinonitrile (1 equiv) and hydrazine monohydrate (2.0 equiv) were combined in absolute ethanol (4× vol) and heated to 55° C. for 24 h. The slurry was cooled to room temperature and filtered. The collected solids were washed with ethanol and methyl tert-butyl ether, and the solids were dried to deliver 5-bromo-6-methylpicolinimidohydrazide as a beige powder. 5-Bromo-6-methylpicolinimidohydrazide and formic acid (15 equiv) were combined and heated to 100° C. with stirring for 6 h. The reaction solution was cooled to 40° C., treated with methanol, stirred for 30 min and concentrated under reduced pressure to 20% of the reaction volume. The mixture was diluted with methanol and again concentrated under reduced pressure to 20% of the reaction volume. The resulting solids were filtered, washed with water, and dried to give the title compound as an off-white powder.

C. 3-Bromo-2-methyl-6-(1-(tetrahydro-2H-pyran-2-yl)-1H-1,2,4-triazol-3-yl)pyridine. 3-Bromo-2-methyl-6-(1H-1,2,4-triazol-3-yl)pyridine (0.7 g, 2.93 mmol) and 3,4-dihydro-2H-pyran (0.493 g, 5.86 mmol) were dissolved in tetrahydrofuran (20 mL). TFA (3.34 mg, 0.029 mmol) was added and the resulting solution was heated to 70° C. for 16 h.

The reaction mixture was cooled to room temperature, diluted with ethyl acetate, filtered and poured into a reparatory funnel containing water and ethyl acetate. The organic layer was concentrated under reduced pressure. Flash chromatography (0-60% ethyl acetate in hexane) gave the desired product as a white solid (0.40 g, 1.23 mmol, 42% yield). MS (ESI) m/z 325.1 [M+2]$^+$. Alternate approach: 3-Bromo-2-methyl-6-(1H-1,2,4-triazol-3-yl)pyridine (1 equiv), 3,4-dihydro-2H-pyran (2 equiv) and methanesulfonic acid (0.08 equiv) were combined in tetrahydrofuran (8× vol). The solution was heated and stirred at 68° C. for 3.5 h then cooled to room temperature. Triethylamine (0.4 equiv) was added and the resulting solution was concentrated under reduced pressure to an oil. The oil was treated with acetonitrile and concentrated under reduced pressure iteratively until a solid was obtained. The solid was dissolved in acetonitrile and treated with water. The suspension was filtered and the solids were collected and dried. The crude product was slurried in hexanes, filtered and dried to give the purified title compound as a light pink solid.

D. (cis)-4-Methoxycyclohexanamine hydrochloride. To a round bottom flask, under nitrogen atmosphere tert-butyl (cis)-4-hydroxycyclohexylcarbamate (7.8 g, 36.2 mmol) was added and suspended in anhydrous tetrahydrofuran (181.0 mL) and cooled to 0° C. Sodium hydride (2.174 g, 54.3 mmol) was then added and the resulting solution was allowed to stir for 5 min. To a second flask under nitrogen atmosphere methyl iodide (2.265 mL, 36.2 mmol) was added and suspended in anhydrous tetrahydrofuran (10.0 mL). The methyl iodide solution in tetrahydrofuran was slowly added dropwise to first flask over 3 min. The reaction was allowed to stir at rt for 16 h. The organic volatiles were removed under reduced pressure and partitioned between ethyl acetate (3×) and water. Organic fractions were pooled, dried over magnesium sulfate, filtered and condensed under reduced pressure. The resulting material was purified by silica gel column chromatography (25-50% ethyl acetate in hexanes). The desired fractions were combined and organic volatiles removed under reduced pressure followed by the addition of hydrochloric acid (4M in 1,4-dioxane, 23.5 mL). The resulting solution was heated to 40° C. for 1 h and organic volatiles were removed under reduced pressure to afford the title compound (6.0 g, 36.2 mmol, 100% yield). MS (ESI) m/z 130.1 [M+1]$^+$.

E. 6-Bromo-4-((cis)-4-methoxycyclohexyl)-3,4-dihydropyrazino[2,3-b]pyrazin-2(1H)-one. To a solution of N-(3,5-dibromopyrazin-2-yl)-2-iodoacetamide (See Example 5.B) (1.0 g, 2.376 mmol) and diisopropylethylamine (1.038 mL, 5.94 mmol) in acetonitrile (10 mL) was added (cis)-4-methoxycyclohexanamine hydrochloride (0.413 g, 2.495 mmol). The solution was stirred at 55° C. for 3 h. The resulting precipitate was filtered and washed with acetonitrile and dried under reduced pressure to afford the title compound (0.442 g, 1.29 mmol, 55% yield). MS (ESI) m/z 341.3 [M]$^+$, 343.3 [M+2]$^+$.

F. 4-((cis)-4-Methoxycyclohexyl)-6-(trimethylstannyl)-3,4-dihydropyrazino[2,3-b]pyrazin-2(1H)-one. 6-Bromo-4-((cis)-4-methoxycyclohexyl)-3,4-dihydropyrazino[2,3-b]pyrazin-2(1H)-one (0.442 g, 1.295 mmol), tetrakis(triphenylphosphine)palladium (0.225 g, 0.194 mmol) and hexamethylditin (0.322 mL, 1.554 mmol) were combined in dioxane (5 mL). The solution was purged with nitrogen gas and heated to 90° C. in a screw capped tube for 3 h. The solution was condensed under reduced pressure and purified using Biotage column chromatography (0-50% ethyl acetate in hexanes) to afford the title compound (0.356 g, 0.837 mmol, 65% yield). MS (ESI) m/z 426.5 [M+1]$^+$, 427.5 [M+1]$^+$.

G. 4-((cis)-4-Methoxycyclohexyl)-6-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one. 4-((cis)-4-Methoxycyclohexyl)-6-(trimethylstannyl)-3,4-dihydropyrazino[2,3-b]pyrazin-2(1H)-one 0.292 g, 0.687 mmol), 3-bromo-2-methyl-6-(1-(tetrahydro-2H-pyran-2-yl)-1H-1,2,4-triazol-3-yl)pyridine (0.244 g, 0.756 mmol), tris(dibenzylideneacetone)dipalladium (0.063 g, 0.069 mmol), tri-o-tolylphosphine (0.042 g, 0.137 mmol), triethylamine (0.287 mL, 2.061 mmol) and dimethylformamide (5.0 mL) were combined in a screw capped flask and heated to 95° C. for 1 h. The solution was condensed under reduced pressure and purified using Biotage chromatography (0-80% ethyl acetate in hexanes followed by 0-10% methanol in ethyl acetate) to afford the title compound (0.279 g, 0.687 mmol, 80% yield). MS (ESI) m/z 505.6 [M+1]$^+$.

H. 4-((cis)-4-Methoxycyclohexyl)-6-(2-methyl-6-(4H-1,2,4-triazol-3-yl)pyridin-3-yl)-3,4-dihydropyrazino[2,3-b]pyrazin-2(1H)-one. 4-((cis)-4-Methoxycyclohexyl)-6-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one (0.279 g, 0.553 mmol) was diluted with ethanol (15 mL) and hydrogen chloride (4.0 N in dioxanes, 5 mL). The solution was stirred at 75° C. for 1 h and at 80° C. for 2 h. The solution was condensed to a slurry and diluted with ethanol and sonicated. The precipitate was filtered and washed with additional ethanol followed by acetonitrile. The crude solid was purified using reverse-phased semi-preparative HPLC (10-100% acetonitrile+0.1% TFA in water+0.1% TFA, over 30 min) to afford the title compound (0.040 g, 0.095 mmol, 17% yield). $^1$H NMR (400 MHz, METHANOL-$d_4$) δ (ppm) 7.88-8.13 (m, 2H), 7.65 (s, 1H), 4.58 (s, 1H), 4.16 (s, 2H), 3.47 (br. s., 1H), 3.22-3.32 (m, 66H), 2.73 (s, 3H), 2.08 (br. s., 2H), 1.91 (br. s., 2H), 1.56 (br. s., 4H); MS (ESI) m/z 421.2 [M+1]$^+$; mp 192-195° C.

Example 14

1-Isopropyl-7-(2-methyl-6-(4H-1,2,4-triazol-3-yl)pyridin-3-yl)-3,4-dihydropyrazino[2,3-b]pyrazin-2(1H)-one

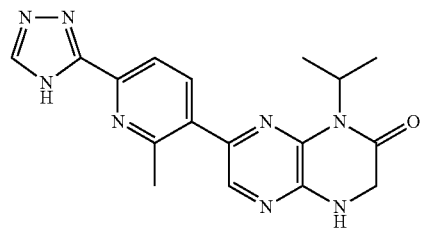 [SMILES: Cc1nc(-c2nnc[nH]2)ccc1-c1cnc2c(n1)N(C(C)C)C(=O)CN2]

A. 1-Isopropyl-7-(trimethylstannyl)-3,4-dihydropyrazino[2,3-b]pyrazin-2(1H)-one. 7-Bromo-1-isopropyl-3,4-dihydropyrazino[2,3-b]pyrazin-2(1H)-one (See Example 7.B) (0.5 g, 1.844 mmol), hexamethylditin (0.725 g, 2.213 mmol), tetrakis(triphenylphosphine)palladium(0) (0.213 g, 0.184 mmol) and 1,4-dioxane (3 mL) were combined in a sealable vessel with a stirbar. Nitrogen gas was bubbled through the solution. The vessel was sealed, stirred vigorously and heated at 100° C. for 2 h. The resulting cloudy black mixture was diluted with ethyl acetate, filtered and the filter cake washed thoroughly with ethyl acetate. The filtrate was concentrated under reduced pressure and purified using silica gel flash column chromatography (20-80% ethyl acetate in hexanes) to give the desired product (2.410 g, 77% yield) as a yellow-white solid. MS (ESI) m/z 357.4 [M+2]⁺

B. 1-Isopropyl-7-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one. To a flask was added 3-Bromo-2-methyl-6-(1-(tetrahydro-2H-pyran-2-yl)-1H-1,2,4-triazol-3-yl)pyridine (0.446 g, 1.380 mmol), 1-isopropyl-7-(trimethylstannyl)-3,4-dihydropyrazino[2,3-b]pyrazin-2(1H)-one (0.490 g, 1.380 mmol), tris(dibenzylideneacetone)dipalladium(0) (0.139 g, 0.152 mmol), tri-o-tolylphosphine (0.092 g, 0.304 mmol), triethylamine (0.577 mL, 4.14 mmol) and N,N-dimethylformamide (3 mL). Nitrogen gas was bubbled through the reaction mixture for 5 min and the mixture was heated to 100° C. for 1 h. After cooling to rt, the reaction mixture was filtered through Celite, rinsed with methanol and concentrated to dryness. The resulting residue was purified by silica gel flash column chromatography (0-80% ethyl acetate in hexanes, followed by 0-10% methanol in dichloromethane) to yield the desired product (0.40 g, 0.921 mmol, 66.7% yield). MS (ESI) m/z 435.5 [M+1]⁺.

C. 1-Isopropyl-7-(2-methyl-6-(4H-1,2,4-triazol-3-yl)pyridin-3-yl)-3,4-dihydropyrazino[2,3-b]pyrazin-2(1H)-one. To a stirred mixture of 1-isopropyl-7-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one (0.400 g, 0.921 mmol) in ethanol (40 mL) at 50° C. was added hydrogen chloride (4 M in dioxane, 1.381 mL, 5.52 mmol). The resulting mixture was heated at 50° C. under nitrogen for 1 h. The suspension was concentrated under reduced pressure and the resulting solid was taken up in dimethylsulfoxide and purified using silica gel chromatography (0-10% ammonia saturated methanol in dichloromethane) to afford the title compound (0.200 g, 0.571 mmol, 62.0% yield) as a brown-red solid, which was further processed by recrystallization. ¹H NMR (400 MHz, DMSO-d₆) δ (ppm) 8.10 (br. s., 1H), 8.01 (br. s., 2H), 7.92 (s, 1H), 5.26 (quin, J=6.93 Hz, 1H), 4.14 (s, 2H), 3.58 (d, J=5.08 Hz, 3H), 1.47 (d, J=6.64 Hz, 6H); MS (ESI) m/z 351.5 [M+1]⁺.

D. 1-Isopropyl-7-(2-methyl-6-(4H-1,2,4-triazol-3-yl)pyridin-3-yl)-3,4-dihydropyrazino[2,3-b]pyrazin-2(1H)-one (alternate approach). 7-Bromo-1-isopropyl-3,4-dihydropyrazino[2,3-b]pyrazin-2(1H)-one (1 equiv), bis(pinacolato)diboron) (1 equiv), potassium acetate (3 equiv) and bis(1,1'-bis(diphenylphosphino)ferrocene)palladium (0.01 equiv) were combined in dioxane (1.2 L), degassed with nitrogen and heated to 95° C. under nitrogen. Dilution with ethyl acetate, filtration through Celite, concentration, trituration with ethyl acetate and hexanes, filtration and drying gave the boronate ester in 60% yield. tert-Butyl 3-(5-bromo-6-methylpyridin-2-yl)-1H-1,2,4-triazole-1-carboxylate (1 equiv), 1-isopropyl-7-(4,4,5,5-tetramethyl-1,3,2-dioxaborolan-2-yl)-3,4-dihydropyrazino[2,3-b]pyrazin-2(1H)-one (1.2 equiv), tetrakis(triphenylphosphine) palladium(0) (0.05 equiv), sodium carbonate (3 equiv) were combined in (3:1) dimethyl acetamide and water. The mixture was degassed and heated to 100° C. overnight. Standard ethyl acetate/water work up and subsequent trituration in ethyl acetate gave the desired product in 41% yield.

Example 15

7-(1H-Pyrrolo[2,3-b]pyridin-5-yl)-1-(2-(tetrahydro-2h-pyran-4-yl)ethyl)-3,4-dihydropyrazino[2,3-b]pyrazin-2(1H)-one

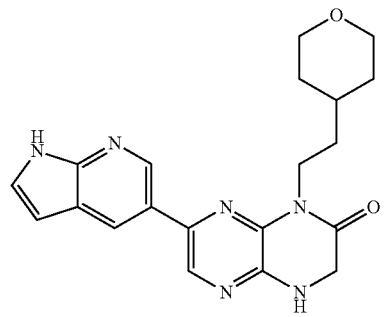 [SMILES: O=C1CNc2ncc(-c3cnc4[nH]ccc4c3)nc2N1CCC1CCOCC1]

A. Ethyl 2-(5-bromo-3-(2-(tetrahydro-2H-pyran-4-yl)ethylamino)pyrazin-2-ylamino)acetate Ethyl 2-(3,5-dibromopyrazin-2-ylamino)acetate (See Example 6.B) (1.0 g, 2.95 mmol) and 2-(tetrahydro-2H-pyran-4-yl)ethanamine (0.381 g, 2.95 mmol) were placed in a microwave vial, dimethylsulfoxide (2 mL) was added and the resulting mixture was heated in a Biotage Emrys Optimizer microwave reactor at 150° C. for 3600 s. The crude reaction mixture was purified using silica gel chromatography (33% ethyl acetate in hexanes) to yield the title compound (0.5 g, 1.3 mmol, 44% yield). MS (ESI) m/z 387.1 [M]⁺, 389.1 [M+2]⁺.

B. 7-Bromo-1-(2-(tetrahydro-2H-pyran-4-yl)ethyl)-3,4-dihydropyrazino[2,3-b]pyrazin-2(1H)-one Ethyl 2-(5-bromo-3-(2-(tetrahydro-2H-pyran-4-yl)ethylamino)pyrazin-2-ylamino)acetate (0.5 g, 1.291 mmol) and hydrochloric acid (6 M in water, 0.215 mL, 1.291 mmol) were combined in ethanol (2 mL) and the resulting mixture was heated in a Biotage Emrys Optimizer microwave reactor at 100° C. for 2400 s. The reaction mixture was concentrated and purified using silica gel chromatography (33% ethyl acetate in hexanes) to yield the title compound (quantitative yield). MS (ESI) m/z 341.1 [M]⁺, 343.1 [M+2]⁺.

C. 1-(2-(Tetrahydro-2H-pyran-4-yl)ethyl)-7-(trimethylstannyl)-3,4-dihydropyrazino[2,3-b]pyrazin-2(1H)-one. 7-Bromo-1-(2-(tetrahydro-2H-pyran-4-yl)ethyl)-3,4-dihydropyrazino[2,3-b]pyrazin-2(1H)-one (0.4 g, 1.29 mmol), hexamethylditin (0.57 g, 1.75 mmol) and tetrakis(triphenylphosphine)palladium(0) (0.2 g, 0.176 mmol) were placed in a sealed tube with 1,4-dioxane (5 mL). The flask was evacuated, flushed with nitrogen, sealed and heated at 110° C. for 1 h. The reaction mixture was cooled to room temperature and filtered through Celite, washing with ethyl acetate. The filtrate was concentrated and sonicated with a small volume of solvent mixture (50% hexane in ethyl acetate) and isolated by filtration to yield the title compound (0.34 g, 0.8 mmol, 54.6% yield). MS (ESI) m/z 427 [M+2]⁺.

D. 7-(1H-Pyrrolo[2,3-b]pyridin-5-yl)-1-(2-(tetrahydro-2H-pyran-4-yl)ethyl)-3,4-dihydropyrazino[2,3-b]pyrazin-2(1H)-one 1-(2-(Tetrahydro-2H-pyran-4-yl)ethyl)-7-(trimethylstannyl)-3,4-dihydropyrazino[2,3-b]pyrazin-2(1H)-one (1.0 g, 2.352 mmol), 5-bromo-1H-pyrrolo[2,3-b]pyridine (0.556 g, 2.82 mmol), tris(dibenzylideneacetone)palladium (0) (0.237 g, 0.259 mmol), tri-o-tolylphosphine (0.158 g, 0.518 mmol) and triethylamine (0.984 mL, 7.06 mmol) were combined in a sealed tube, dimethylformamide (5 mL) was added. The atmosphere in the vessel was removed under vacuum and replaced with nitrogen gas. The reaction was heated to 100° C. for 1 h. After cooling to room temperature, the reaction mixture was filtered through Celite. The filter cake was washed with ethyl acetate. The wash and filtrate were combined and concentrated nearly to dryness. The resulting solid was dissolved in hot methanol, filtered through Celite and purified by reverse-phase preparative HPLC (5-80% acetonitrile+0.1% TFA in water+0.1% TFA, over 30 min). The clean fractions were collected, neutralized with ammonium hydroxide and concentrated to dryness. The solid obtained was filtered, washed with water and dried under high vacuum to yield the title compound (0.10 g, 0.264 mmol, 11.2% yield). $^1$H NMR (400 MHz, DMSO-$d_6$) δ (ppm) 11.71 (br. s., 1H), 8.81 (s, 1H), 8.44 (s, 1H), 8.26 (s, 1H), 7.49 (d, J=10.54 Hz, 2H), 6.48 (br. s., 1H), 4.18 (s, 2H), 4.13 (t, J=6.44 Hz, 2H), 3.82 (d, J=12.89 Hz, 2H), 3.27 (t, J=11.13 Hz, 2H), 1.71 (d, J=12.49 Hz, 2H), 1.60 (br. s., 3H), 1.24 (d, 2H); MS (ESI) m/z 379.2 [M+1]$^+$; mp 255-258° C.

Example 16

6-(6-(2-Hydroxypropan-2-yl)pyridin-3-yl)-4-((tetrahydro-2H-pyran-4-yl)methyl)-3,4-dihydropyrazino[2,3-b]pyrazin-2(1H)-one

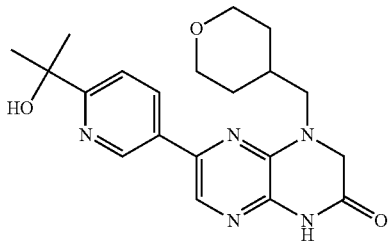 [SMILES: CC(C)(O)c1ccc(-c2cnc3c(n2)N(CC2CCOCC2)CC(=O)N3)cn1]

A. 6-Bromo-4-((tetrahydro-2H-pyran-4-yl)methyl)-3,4-dihydropyrazino[2,3-b]pyrazin-2(1H)-one. N-(3,5-Dibromopyrazin-2-yl)-2-iodoacetamide (See Example 5.B) (8.0 g, 19.01 mmol), (tetrahydro-2H-pyran-4-yl)methanamine (2.63 g, 22.81 mmol) and diisopropylethylamine (6.64 mL, 38.0 mmol) were placed in a 250 mL round bottom flask, suspended in acetonitrile (80.0 mL) and heated to 40° C. for 16 h. The resulting white precipitate was filtered, washed with acetonitrile followed by hexanes and dried under vacuum to afford the title compound (4.89 g, 14.95 mmol, 79% yield). MS (ESI) m/z 327.4 [M]$^+$, 329.5 [M+2]$^+$.

B. 6-(6-(2-Hydroxypropan-2-yl)pyridin-3-yl)-4-((tetrahydro-2H-pyran-4-yl)methyl)-3,4-dihydropyrazino[2,3-b]pyrazin-2(1H)-one. 6-Bromo-4-((tetrahydro-2H-pyran-4-yl)methyl)-3,4-dihydropyrazino[2,3-b]pyrazin-2(1H)-one (35.98 g, 110 mmol), 2-(5-(trimethylstannyl)pyridin-2-yl)propan-2-ol (See Example 5.E) (33.0 g, 110 mmol) and [1,1'-bis(diphenyl-phosphino)ferrocene]dichloro-palladium(II) complex with dichloromethane (1:1) (8.05 g, 11.00 mmol) were combined in a sealed tube and suspended in N,N-dimethylformamide (288 mL). The reaction was then heated to 125° C. for 2 h. The reaction was cooled slightly and poured while still warm onto a silica gel column and purified using an Biotage SP1 (0-100% (5% methanol in ethyl acetate) in hexanes). The desired fractions were combined and organic volatiles removed under reduced pressure. The residue was triturated with 20% ethyl acetate in hexanes followed by several washes with denatured ethanol. The slightly yellow solid was dried under reduced pressure to afford the desired compound (15.08 g, 39.3 mmol, 35.8% yield). $^1$H NMR (400 MHz, DMSO-$d_6$) δ (ppm) 11.32 (s, 1H), 9.07 (d, J=1.56 Hz, 1H), 8.29 (dd, J=8.59, 2.34 Hz, 1H), 8.05 (s, 1H), 7.72 (d, J=8.20 Hz, 1H), 5.26 (s, 1H), 4.21 (s, 2H), 3.83 (d, J=2.73 Hz, 2H), 3.51 (d, J=7.42 Hz, 2H), 3.27 (t, J=11.32 Hz, 2H), 2.09 (br. s., 1H), 1.61 (d, J=11.3 Hz, 2H), 1.46 (s, 6H), 1.24-1.38 (m, 2H); MS (ESI) m/z 384.2 [M+1]$^+$; mp 268-269° C.

Example 17

7-(6-(2-Hydroxypropan-2-yl)pyridin-3-yl)-1-(2-methoxyethyl)-3,4-dihydropyrazino[2,3-b]pyrazin-2(1H)-one

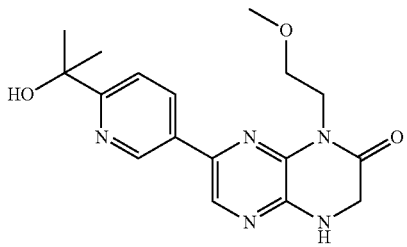 [SMILES: COCCN1C(=O)CNc2ncc(-c3ccc(C(C)(C)O)nc3)nc21]

A. 7-Bromo-1-(2-methoxyethyl)-3,4-dihydropyrazino[2,3-b]pyrazin-2(1H)-one. Ethyl 2-(3,5-dibromopyrazin-2-ylamino)acetate (See Example 1.C) (1 equiv), 2-methoxyethanamine (1 equiv), diisopropylethylamine (3 equiv), were suspended in dimethylsulfoxide and heated in an Emrys Biotage microwave reactor at 150° C. for 1 h. Standard ethyl acetate/water work up gave crude material, which was suspended in 99.7% acetic acid. The reaction was sealed, heated to 120° C. and allowed to stir for 2 h. The reaction was extracted in ethyl acetate. The organic layers were pooled and washed with saturated sodium bicarbonate, followed by brine and dried over magnesium sulfate. Concentration and flash column chromatography (0-100% ethyl acetate in hexanes) gave the desired product in 27% yield over two steps. MS (ESI) m/z 287.4 [M]$^+$, 289.4 [M+2]$^+$.

B. 7-(6-(2-Hydroxypropan-2-yl)pyridin-3-yl)-1-(2-methoxyethyl)-3,4-dihydropyrazino[2,3-b]pyrazin-2(1H)-one. 7-Bromo-1-(2-methoxyethyl)-3,4-dihydropyrazino[2,3-b]pyrazin-2(1H)-one (1 equiv), 2-(5-(trimethylstannyl)pyridin-2-yl)propan-2-ol (See Example 5.E) (1 equiv) and dichlorobis(triphenylphosphine)-palladium(II) (0.2 equiv) were suspended in dimethylformamide. The reaction was purged with nitrogen and was heated to 140° C. for 2 h. The reaction was cooled to room temperature, filtered through Celite and washed with ethyl acetate. Volatiles were removed under reduced pressure and the resulting purple slurry was purified using silica gel column chromatography (0-100% (5% methanol in ethyl acetate) in hexanes). The desired fractions were combined and organic volatiles removed under reduced pressure. The solid was triturated in 5% ethyl acetate in hexanes and washed with hexanes to afford the desired product in 38% yield. $^1$H NMR (400 MHz, DMSO-$d_6$) δ (ppm) 9.02 (d, J=1.6 Hz, 1H), 8.27 (s, 1H), 8.24 (dd, J=8.6, 2.3 Hz, 1H), 7.71 (d, J=0.8 Hz, 1H), 7.69 (s, 1H), 5.25 (s, 1H), 4.28 (t, J=6.2 Hz, 2H), 4.20 (d, 2H), 3.60 (t, J=6.2 Hz, 2H), 3.26 (s, 3H), 1.46 (s, 6H); MS (ESI) m/z 344.3 [M+1]$^+$.

Example 18

7-(1H-Pyrrolo[2,3-b]pyridin-4-yl)-1-[2-(tetrahydro-pyran-4-yl)-ethyl]-3,4-dihydro-1H-pyrazino[2,3-b]pyrazin-2-one

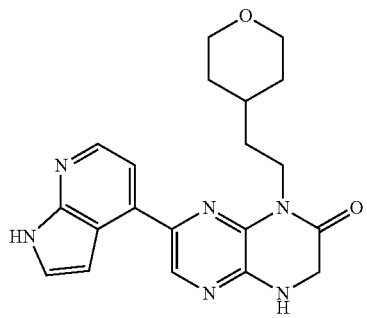 [SMILES: O=C1CNc2ncc(-c3ccnc4[nH]ccc34)nc2N1CCC1CCOCC1]

A. 7-(1H-Pyrrolo[2,3-b]pyridin-4-yl)-1-[2-(tetrahydropyran-4-yl)-ethyl]-3,4-dihydro-1H-pyrazino[2,3-b]pyrazin-2-one. A mixture of 1-(2-(tetrahydro-2H-pyran-4-yl)ethyl)-7-(trimethylstannyl)-3,4-dihydropyrazino[2,3-b]pyrazin-2(1H)-one (See Example 15.C) (1 equiv), 4-bromo-pyrrolo[2,3-b]pyridine-1-carboxylic acid tert-butyl ester (1 equiv), tris(dibenzylideneacetone) palladium (0.13 equiv), tri-o-tolylphosphine (0.25 equiv) and triethylamine (2.8 equiv) in anhydrous dioxane was purged, degassed for 2 min and stirred at 95° C. under nitrogen for 3-4 h. Upon completion of the reaction as indicated by TLC, the volatiles were removed under reduced pressure and the residue was purified by column chromatography to give the desired product in 35% yield. MS (ESI) m/z 479.7 [M+1]+. Tert-Butyl 4-(7-oxo-8-(2-(tetrahydro-2H-pyran-4-yl)ethyl)-5,6,7,8-tetrahydropyrazino[2,3-b]pyrazin-2-yl)-1H-pyrrolo[2,3-b]pyridine-1-carboxylate was stirred in methanolic hydrochloride solution at room temperature. Upon completion of the reaction as indicated by TLC, the solvent was removed under reduced pressure and the residue was purified on silica gel to give the title compound in 63% yield. $^1$H NMR (DMSO-$d_6$, 400 MHz) δ (ppm) 11.72 (s, 1H), 8.38 (s, 1H), 8.25 (d, J=4.8 Hz, 1H), 7.79 (s, 1H), 7.53-7.51 (m, 2H), 6.97 (q, J=1.6 Hz, 1H), 4.23 (s, 2H), 4.14 (t, J=7.6 Hz, 2H), 3.81 (dd, $J_1$=2.4 Hz, $J_2$=11.2 Hz, 2H), 3.25 (d, J=10.8 Hz, 2H), 1.67 (d, J=13.2 Hz, 2H), 1.61 (m, 3H), 1.22 (m, 2H); MS (ESI): m/z 379.2 [M+1]+.

Example 19

1-(2-Methoxyethyl)-7-(2-methyl-6-(4H-1,2,4-triazol-3-yl)pyridin-3-yl)-3,4-dihydropyrazino[2,3-b]pyrazin-2(1H)-one

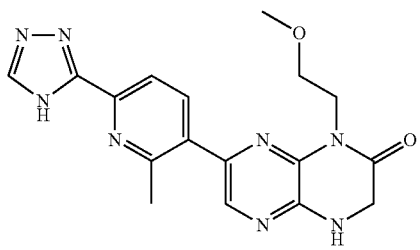 [SMILES: COCCN1C(=O)CNc2ncc(-c3ccc(-c4nnc[nH]4)nc3C)nc21]

A. 1-(2-Methoxyethyl)-7-(trimethylstannyl)-3,4-dihydropyrazino[2,3-b]pyrazin-2(1H)-one. 7-Bromo-1-(2-methoxyethyl)-3,4-dihydropyrazino[2,3-b]pyrazin-2(1H)-one (See Example 17.A) (0.5 g, 1.741 mmol), 1,1,1,2,2,2-hexamethyldistannane (0.856 g, 2.61 mmol) and tetrakis(triphenylphosphine) palladium(0) (0.201 g, 0.174 mmol) were combined in 1,4-dioxane (20 mL) and heated at 140° C. for 2 h. The resulting mixture cooled to room temperature, diluted with ethyl acetate and filtered through Celite. The filtrate was concentrated under reduced pressure. Flash chromatography (0-30% ethyl acetate in hexane) gave the desired product as clear oil (0.5 g, 1.34 mmol, 77% yield). MS (ESI) m/z 373.0 [M+2]+.

B. 1-(2-Methoxyethyl)-7-(2-methyl-6-(4H-1,2,4-triazol-3-yl)pyridin-3-yl)-3,4-dihydropyrazino[2,3-b]pyrazin-2(1H)-one. 1-(2-Methoxyethyl)-7-(trimethylstannyl)-3,4-dihydropyrazino[2,3-b]pyrazin-2(1H)-one (0.5 g, 1.348 mmol), 3-bromo-2-methyl-6-(1-(tetrahydro-2H-pyran-2-yl)-1H-1,2,4-triazol-3-yl)pyridine (0.436 g, 1.348 mmol), tris(dibenzylidineacetone)dipalladium(0) (0.123 g, 0.135 mmol), tri-o-tolylphosphine (0.082 g, 0.270 mmol), triethylamine (0.584 mL, 4.04 mmol) and N,N-dimethylformamide (10 mL) were combined in a 75 mL sealable flask, the atmosphere in the flask was removed and replaced with nitrogen. The mixture was stirred at 130° C. for 3 h. The resulting mixture was cooled to room temperature and filtered. The organic layer was concentrated under reduced pressure. The resulting residue was diluted with methanol and dimethylsulfoxide, filtered and purified using reverse-phase preparatory HPLC (10-30% acetonitrile+0.1% TFA in water+0.1% TFA, over 30 min). Fractions containing clean product were passed through a Phenomenex Strata-X-C solid phase extraction column. The column was washed successively with water, acetonitrile, methanol and 5% ammonium hydroxide in methanol. The product eluted with the 5% ammonium hydroxide in methanol eluent and was concentrated under reduced pressure. The residue was triturated with ethyl ether in hexane to make a fine powder and dried under vacuum at 50° C. to give the desired product (0.05 g, 0.136 mmol, 10% yield) as a white solid. $^1$H NMR (400 MHz, DMSO-$d_6$) δ (ppm) 8.10 (br. s., 1H), 7.98 (br. s., 1H), 7.94 (s, 1H), 7.73 (br. s., 1H), 4.13-4.28 (m, 4H), 3.55 (t, J=6.25 Hz, 2H), 3.24 (s, 3H), 2.70 (br. s., 3H); MS (ESI) m/z 367.2[M+1]+.

Example 20

6-(4-(4H-1,2,4-Triazol-3-yl)phenyl)-4-ethyl-3,4-dihydropyrazino[2,3-b]pyrazin-2(1H)-one hydrochloride

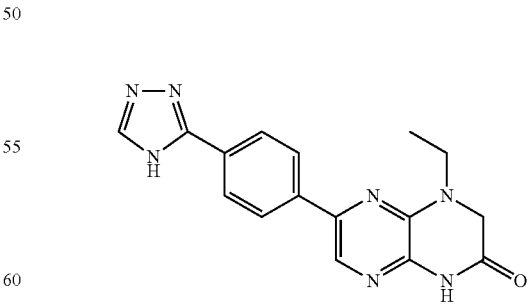

A. 6-Bromo-4-ethyl-3,4-dihydropyrazino[2,3-b]pyrazin-2(1H)-one. To a solution of 2-bromo-N-(3,5-dibromopyrazin-2-yl)acetamide (See Example 4.A) (1 equiv) and diisopropylethylamine (3 equiv) in acetonitrile was added ethanamine hydrochloride (1.05 equiv). The solution was allowed to heat to 70° C. for 30 min. The solution was condensed under reduced pressure and purified using column chromatography (0-75% ethyl acetate in hexanes) to afford the title compound in 36% yield. MS (ESI) m/z 257.5 [M]+, 259.4 [M+2]+.

B. 4-Ethyl-6-(4-(4-(tetrahydro-2H-pyran-2-yl)-4H-1,2,4-triazol-3-yl)phenyl)-3,4-dihydro-pyrazino[2,3-b]pyrazin-2(1H)-one 6-Bromo-4-ethyl-3,4-dihydropyrazino[2,3-b]pyrazin-2(1H)-one (1.1 equiv), 4-(tetrahydro-2H-pyran-2-yl)-3-(4-(4,4,5,5-tetramethyl-1,3,2-dioxaborolan-2-yl)phenyl)-4H-1,2,4-triazole (1 equiv) and dichloro[1,1'-bis(diphenylphosphino)ferrocene]palladium (II) dichloromethane (0.05 equiv) were combined in 1,4-dioxane followed by the addition of sodium carbonate (3 equiv) in water. The solution was heated in a Biotage Emrys Optimizer microwave reactor to 120° C. for 30 min. The solution was condensed under reduced pressure and purified using column chromatography (0-10% methanol in ethyl acetate) to afford the title compound in 45% yield. MS (ESI) m/z 406.6 [M+1]+.

C. 6-(4-(4H-1,2,4-Triazol-3-yl)phenyl)-4-ethyl-3,4-dihydropyrazino[2,3-b]pyrazin-2(1H)-one hydrochloride. 4-Ethyl-6-(4-(4-(tetrahydro-2H-pyran-2-yl)-4H-1,2,4-triazol-3-yl)phenyl)-3,4-dihydropyrazino[2,3-b]pyrazin-2(1H)-one in ethanol was treated with 2 N hydrogen chloride in dioxane. The solution was stirred at 75° C. for 1 h. The solution was condensed partially and cooled. Cold ethanol was added to the slurry and the resulting precipitate filtered and washed with additional cold ethanol followed by hexanes to afford the title compound as the hydrochloride salt in 82% yield. $^1$H NMR (400 MHz, METHANOL-$d_4$) δ (ppm) 9.18 (s, 1H), 8.22 (d, J=8.59 Hz, 2H), 8.04-8.09 (m, 3H), 7.66-7.74 (m, 1H), 7.58-7.64 (m, 1 H), 4.24 (s, 2H), 3.74 (q, J=7.03 Hz, 2H), 1.29 (t, J=7.03 Hz, 4H), 0.79-0.98 (m, 4H); MS (ESI) m/z 322.2 [M+1]+.

Building Block Synthesis

The following building blocks were prepared and used in the preparations as described herein, or variations known in the art thereof.

tert-Butyl 4-bromo-1H-pyrrolo[2,3-b]pyridine-1-carboxylate

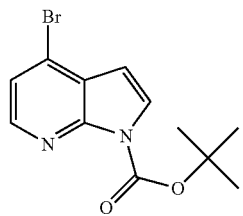 [SMILES: CC(C)(C)OC(=O)n1ccc2c(Br)ccnc21]

A. 4-Bromo-1H-pyrrolo[2,3-b]pyridine. A solution of trifluoromethyl sulfonic anhydride (9.3 g, 33 mmol) was added dropwise to a mixture of 1H-pyrrolo[2,3-b]pyridine 7-oxide (3 g, 22 mmol) and tetrabutyl ammonium bromide (10.8 g, 33 mmol) in N,N-dimethylformamide (30 mL) at 0° C. The resulting mixture was stirred at 0° C. for 4 h and at room temperature overnight. The reaction was quenched with water and neutralized with 1N sodium hydroxide to pH=7. The resulting mixture was extracted twice with a mixture of methylene chloride and i-propanol (30 mL, $V_m:V_p$=4:1). The organic layer was combined, dried over anhydrous sodium sulfate, concentrated and purified by a reverse-phase preparatory HPLC (0-30%: acetonitrile+0.1% TFA in water+0.1% TFA, over 15 min.) to give the title compound (1.5 g, 34.3% yield). MS (ESI) m/z 196.8 [M+1]+, 198.8 [M+3]+.

B. tert-Butyl-4-bromo-1H-pyrrolo[2,3-b]pyridine-1-carboxylate. A mixture of 4-bromo-1H-pyrrolo[2,3-b]pyridine (250 mg, 1.26 mmol), di-tert-butyl dicarbonate (302 mg, 1.38 mmol), dimethyl-pyridin-4-yl-amine (7.6 mg, 0.06 mmol) and triethylamine (127 mg, 1.26 mmol) in anhydrous methylene chloride (15 mL) was stirred at room temperature for 3 h. Upon completion of the reaction as indicated by TLC, the volatiles were removed under reduced pressure and the residue was purified by column chromatography on silica gel (9-25% ethyl acetate in petroleum ether) to give the desired product (230 mg, 61% yield) as an oil. MS (ESI) m/z 242.9 [M-56+1]+

1-(Tetrahydro-2H-pyran-2-yl)-4-(4,4,5,5-tetramethyl-1,3,2-dioxaborolan-2-yl)-1H-indazole

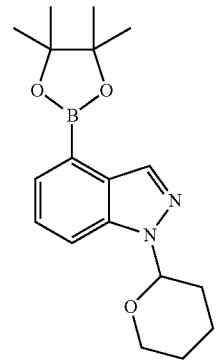 [SMILES: CC1(C)OB(c2cccc3c2cnn3C2CCCCO2)OC1(C)C]

A. 4-Bromo-1H-indazole. To a solution of 3-bromo-2-methylaniline (5 g, 27 mmol) in chloroform (1 mL) was added acetic anhydride (5 g, 27 mmol) at 0° C. and the mixture was stirred at room temperature for 1 h. Potassium acetate (0.75 g, 7.8 mmol) and isoamyl nitrite (0.78 g, 58 mmol) were added and the reaction mixture was refluxed for 18 h. The volatiles were removed under reduced pressure and water (0.65 mL) was added. The mixture was concentrated, diluted with concentrated hydrochloride acid (1 mL) and heated at 50° C. for 2 h. After being cooled to room temperature, aqueous sodium hydroxide solution (50%) was added until pH=10. The aqueous mixture was extracted with ethyl acetate (100 mL×3). The combined organic layer was washed with brine (150 mL), dried over anhydrous sodium sulfate, filtered, evaporated and purified on silica gel column (3% ethyl acetate in petroleum ether) to give the desired product (2.69 g, 34% yield) as a solid. MS (ESI): m/z 197.0 [M+1]+.

B. 4-Bromo-1-(tetrahydro-pyran-2-yl)-1H-indazole. A solution of 4-bromo-1H-indazole (1.82 g, 9.24 mmol), 3,4-dihydro-2H-pyran (1.55 g, 18.48 mmol) and toluene-4-sulfonic acid (0.26 g, 1.39 mmol) in anhydrous tetrahydrofuran (40 mL) was heated at 80° C. overnight under nitrogen. The solvent was removed under reduced pressure and the residue was purified on silica gel column (3% ethyl acetate in petroleum ether) to give the title compound (2.13 g, 81% yield) as a yellow solid. MS (ESI): m/z 280.9 [M+1]+.

C. 1-(Tetrahydro-pyran-2-yl)-4-(4,4,5,5-tetramethyl-[1,3,2]dioxaborolan-2-yl)-1H-Indazole A degassed mixture of 4-bromo-1-(tetrahydro-pyran-2-yl)-1H-indazole (2.13 g, 7.45 mmol), bis(pinacolato)diboron (3.73 g, 14.9 mmol), potassium phosphate (2.70 g, 12.67 mmol), palladium acetate (0.174 g 0.75 mmol) and triphenylphosphine (0.59 g, 2.24 mmol) in 1,2-dimethoxy-ethane (50 mL) was heated at 100° C. under nitrogen overnight. After cooling to room temperature, the reaction mixture was filtered, concentrated under reduced pressure and purified on silica gel column (10-30% ethyl acetate in petroleum ether) to give the product (1.83 g, 74% yield) as a solid. MS (ESI): m/z 329.2 [M+1]$^+$.

3-(4-Bromo-2-fluoro-3-methylphenyl)-4-(tetrahydro-2h-pyran-2-yl)-4H-1,2,4-triazole

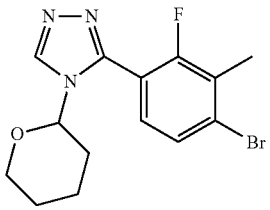 [SMILES: Cc1c(Br)ccc(-c2nncn2C2CCCCO2)c1F]

A. 4-Bromo-3-fluoro-2-methylaniline. To a stirred solution of 3-fluoro-2-methylaniline (25 g, 200 mmol) in acetic acid (140 mL) at 0-5° C. was added hydrogen bromide (100 mL, 200 mmol) then dimethyl sulfoxide (72 mL) was added slowly dropwise (reaction is exothermic and at temperature higher than 5-15° C. produces dibromoisomer). The mixture was stirred at 5-15° C. for 12 h (mixture became clear solution). The resulting solution was cooled to 0° C. and neutralized with sodium hydroxide then with sodium bicarbonate to pH 7. The mixture was extracted with ethyl acetate. The organic layer was concentrated under reduced pressure. Flash chromatography (0-10% ethyl acetate in hexane) gave the desired product as a white solid (23.3 g, 114 mmol, 57% yield). $^1$H NMR (400 MHz, CHLOROFORM-d) δ (ppm) 7.11 (t, J=8.20 Hz, 1H), 6.35 (d, J=8.98 Hz, 1H), 3.72 (br. s., 2H), 2.07 (d, J=1.95 Hz, 3H).

B. 4-Amino-2-fluoro-3-methylbenzonitrile. A mixture of 4-bromo-3-fluoro-2-methylaniline (23 g, 113 mmol) and cyanocopper (20.19 g, 225 mmol) N,N-dimethylformamide (200 mL) was heated to 140° C. for 7 h. After the mixture was cooled to room temperature filtered and poured into a separatory funnel containing water and ethyl acetate (1:1). Layers were separated and the organic layer was concentrated under reduced pressure. Flash chromatography (0-50% ethyl acetate in hexane) gave the desired product (11.4 g, 76 mmol, 67% yield) as a brown solid. $^1$H NMR (400 MHz, CHLOROFORM-d) δ (ppm) 7.22 (t, 1H), 6.45 (d, J=8.59 Hz, 1H), 4.23 (br. s., 2H), 2.07 (s, 3H); MS (ESI) m/z 151.1[M+1]$^+$.

C. 4-Bromo-2-fluoro-3-methylbenzonitrile. A mixture of dimethyl sulfoxide (400 mL) and potassium nitrite (22.67 g, 266 mmol) was stirred to dissolve potassium nitrite and 4-amino-2-fluoro-3-methylbenzonitrile (10 g, 66.6 mmol) and copper(I) bromide (1.911 g, 13.32 mmol) were added. Aqueous 48% hydrogen bromide (33 mL, 266 mmol), diluted with dimethyl sulfoxide (200 mL), was added dropwise and the reaction stirred for 2 h. After complete conversion of starting material, the reaction mixture was poured into iced-cold water and neutralized to pH 7 with cold concentrated sodium hydroxide. The resulting solid was collected by filtration to give the desired product (11.4 g, 53.3 mmol, 80% yield) as white solid. $^1$H NMR (400 MHz, CHLOROFORM-d) δ (ppm) 7.47 (d, J=9.37 Hz, 1H), 7.33 (t, 1H), 2.39 (d, J=2.34 Hz, 3H).

D. 4-Bromo-2-fluoro-3-methylbenzamide. 4-Bromo-2-fluoro-3-methylbenzonitrile (11 g, 51.4 mmol) in a 100 mL mixture of TFA-sulfuric acid (4:1, V/V) was stirred at 40° C. for 16 h. After complete conversion of starting material, the reaction mixture was poured into iced-cold water. The resulting solid was filtered off and washed with water and dried to give the desired product (11.24 g, 48.4 mmol, 94% yield) as a white solid. MS (ESI) m/z 234.1 [M+2]$^+$.

E. 3-(4-Bromo-2-fluoro-3-methylphenyl)-1H-1,2,4-triazole. 4-Bromo-2-fluoro-3-methylbenzamide (11 g, 47.4 mmol) and N,N-dimethylformamide dimethylacetal (60 mL) were combined in a 100 mL round-bottom flask with a stir bar and heated at 55° C. under a reflux condenser under nitrogen for 3 h. The resulting mixture was concentrated under reduced pressure and dried under vacuum to give yellow oil, which was used in the next step without purification. The residue was diluted with acetic acid (60 mL) at 0° C. and hydrazine monohydrate (20 mL) was added dropwise and allowed to stirred at rt for 5 h. After complete conversion of starting material, the reaction mixture was poured into iced-cold water and neutralized to pH 7 with ice cold concentrated sodium hydroxide. The resulting solids were collected by vacuum filtration. Solid was dissolved in ethyl acetate (400 mL) and stirred for 15 min, filtered the insoluble solid, the filtrate dried over magnesium sulfate, filtered, concentrated under reduced pressure and dried under vacuum to give a brown pure solid (4.3 g, 16.79 mmol, 35% yield) which was used in the next step without purification. $^1$H NMR (400 MHz, CHLOROFORM-d) δ (ppm) 8.12 (s, 1H), 7.97 (t, J=8.00 Hz, 1H), 7.52 (d, J=8.59 Hz, 1H), 2.44 (d, 3H).

F. 3-(4-Bromo-2-fluoro-3-methylphenyl)-4-(tetrahydro-2H-pyran-2-yl)-4H-1,2,4-triazole. Methanesulfonic acid (0.090 mL, 1.390 mmol) was added to a stirred solution of 3-(4-bromo-2-fluoro-3-methylphenyl)-1H-1,2,4-triazole (7.0 g, 27.3 mmol) and 3,4-dihydro-2H-pyran (12.68 mL, 139 mmol) in tetrahydrofuran (33 mL). The resulting mixture stirred at 85° C. under a reflux condenser under nitrogen for 20 h. The mixture was diluted with ethyl acetate and washed with saturated aqueous sodium bicarbonate and brine. The organic layer was dried over magnesium sulfate, filtered and concentrated under reduced pressure. The residue was purified using flash chromatography (20-30-50% ethyl acetate in hexane). Product containing fractions were combined and solvent removed under reduced pressure to afford the desired product (8.8 g, 95% yield) as a yellow solid. MS (ESI) m/z 340.0 [M]$^+$ Note: As understood by one of skill in the art, protection, with for example Boc or THP groups, of heterocyclic moieties that are subject to tautomerism, for example triazolyl moieties, potentially may give rise to different regioisomerically protected compounds that may not readily be characterized or distinguished by standard analytical methods such as 1D-NMR. Such regioisomers are referred to herein specifically by the chemical name of only one of the regioisomers, however, it is understood that the name refers to any and all possible regioisomers and their mixtures potentially formed by the reaction. The single regioisomeric designation is thereafter also applied in the naming of the subsequent products formed by reaction with the protected intermediate. As understood by one of skill in the art, upon removal of the protecting group only one product is formed, independent of the starting regioisomerically protected compound.

3-Bromo-2-methyl-6-(1-(tetrahydro-2H-pyran-2-yl)-1H-1,2,4-triazol-3-yl)pyridine

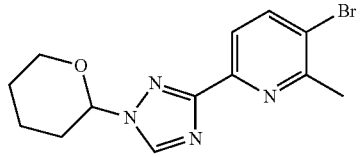 [SMILES: Cc1nc(-c2ncn(C3CCCCO3)n2)ccc1Br]

A. 3-Bromo-6-iodo-2-methylpyridine. Sodium iodide (2 equiv) and 3,6-dibromo-2-methylpyridine (1 equiv) were combined in propionitrile and the resulting slurry was stirred under nitrogen for 5 min. Iodotrimethylsilane (0.2 equiv) was added and the reaction was heated at 95° C., with stirring, under nitrogen for 24 h. The slurry was cooled to room temperature, diluted with a 1:1 mixture of ethyl acetate and water. The mixture was agitated for 15 min and the aqueous and organic phases were then separated. The organic layer was washed sequentially with equal volumes of saturated aqueous sodium bicarbonate solution, sodium thiosulfate (5% aqueous solution), and saturated aqueous sodium chloride solution. The organic phase was dried over anhydrous sodium sulfate, filtered, and concentrated under reduced pressure to afford the desired product in 95% yield, as an oil, which crystallized to an off-white solid. MS (ESI) m/z 297.8 [M]+, 299.8 [M+2]+.

B. 5-Bromo-6-methylpicolinonitrile. Under an inert atmosphere, 3-bromo-6-iodo-2-methylpyridine (1 equiv) and acetonitrile were combined and stirred for 10 min, copper cyanide (0.5 equiv), sodium cyanide (0.8 equiv) and more acetonitrile were added. The reaction slurry was heated, with stirring, at 80° C. for 24 h. The reaction solution was cooled to room temperature and diluted with ammonium hydroxide (0.5 M aqueous solution). The mixture was stirred 15-30 min, filtered through diatomaceous earth and the filter cake was washed with ethyl acetate. The filtrate and wash were combined and further diluted with ethyl acetate and the solution was agitated for 15 min. The aqueous and organic phases were separated and the organic layer was washed sequentially with ammonium hydroxide (0.5 M aqueous solution; four times) and saturated aqueous sodium chloride (twice), dried over anhydrous sodium sulfate, filtered, and concentrated under reduced pressure to provide 5-bromo-6-methylpicolinonitrile in 92% yield, as an off-white solid. MS (ESI) m/z 196.9 [M]+, 198.9 [M+2]+.

C. 5-Bromo-6-methylpicolinimidohydrazide. Hydrazine monohydrate (2 equiv) was added to a stirring 1.2 M suspension of 5-bromo-6-methylpicolinonitrile (1 equiv) in ethanol under nitrogen. The reaction mixture was heated at 50° C. for 24 h. The reaction was cooled to room temperature and then filtered. The collected solid was washed with cold ethanol followed by cold t-butyl methyl ether. The washed solid was dried under vacuum to provide the title compound in 89% yield, as a yellow solid. MS (ESI) m/z 228.9 [M]+, 230.9 [M+2]+.

D. 3-Bromo-2-methyl-6-(4H-1,2,4-triazol-3-yl)pyridine. 5-Bromo-6-methylpicolin-imido-hydrazide (1 equiv) and formic acid (15 equiv) were combined and heated with stirring at 100° C. for 6 h. The reaction was cooled to room temperature and diluted with methanol. The resulting slurry was stirred for 30 min and then partially concentrated under reduced pressure to ~20% of the total volume. The resulting mixture was again diluted with methanol and partially concentrated under reduced pressure to ~20% of the total volume. The resulting solids were collected by filtration, washed three times with water and dried under reduced pressure to provide the desired product in 84% yield, as an off-white solid. MS (ESI) m/z 238.9 [M]+, 240.9 [M+2]+.

E. 3-Bromo-2-methyl-6-(1-(tetrahydro-2H-pyran-2-yl)-1H-1,2,4-triazol-3-yl)pyridine 3-Bromo-2-methyl-6-(4H-1,2,4-triazol-3-yl)pyridine (1 equiv), 3,4-dihydro-2H-pyran (2 equiv) and methanesulfonic acid (0.1 equiv) were combined in tetrahydrofuran, while stirring under nitrogen. The reaction was heated to 68° C. for 3.5 h. After cooling to room temperature over 1 h, triethylamine (0.4 equiv) was added and the resulting solution was stirred 10 min and then concentrated under reduced pressure. Acetonitrile was added and excess tetrahydrofuran was removed by codistillation under reduced pressure, with heating to 35° C. (twice). The resulting residue was dissolved in acetonitrile (1 volume) and water (2.25 volumes) was added. The resultant suspension was stirred 30 min. Solids were collected by filtration, washed with a solution of 20% acetonitrile in water and dried under reduced pressure. The crude product was triturated with hexanes, filtered, further washed with hexanes and dried in a vacuum oven at 35° C. to provide the desired product in 80% yield, as an off white solid. MS (ESI) m/z 324.9 [M+2]+.

3-(4-Bromo-2-fluorophenyl)-4-h-1,2,4-triazole

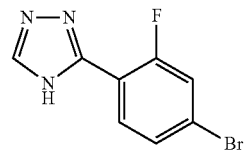 [SMILES: Fc1cc(Br)ccc1-c1nnc[nH]1]

A. 4-Bromo-2-fluorobenzamide. A solution of 4-bromo-2-fluorobenzonitrile (10.0 g, 50.0 mmol) in a 70 mL mixture of TFA (56.0 mL, 727 mmol)-sulfuric acid (14.0 mL, 263 mmol) (4:1 VAT) was stirred at 40° C. for 16 h. The reaction was poured while still warm over ice water. The product precipitated and the solid was filtered and dried to give 4-bromo-2-fluorobenzamide (9.53 g, 43.7 mmol, 87% yield) as a white solid. MS (ESI) m/z 218.1 [M]+, 220.1 [M+2]+.

B. 3-(4-Bromo-2-fluorophenyl)-4H-1,2,4-triazole. 4-Bromo-2-fluorobenzamide (9.53 g, 43.7 mmol) and N,N-dimethylformamide dimethylacetal (75.0 mL) were combined in a 500 mL round bottom flask and purged with nitrogen. The reaction was heated to reflux at 85° C. for 2 h. The resulting mixture was concentrated under reduced pressure and dried under vacuum to afford a yellow oil. The oil was suspended in concentrated acetic acid (75.0 mL) and cooled to 0° C. Hydrazine hydrate (21.88 g, 437 mmol) was added dropwise and the mixture was allowed to stir at rt for 5 h. The reaction was poured warm onto cold ice and extracted with dichloromethane (3×200 mL). Organic volatiles were removed under reduced pressure to afford 3-(4-bromo-2-fluorophenyl)-4H-1,2,4-triazole (7.20 g, 29.7 mmol, 68.1% yield) as a white solid. MS (ESI) m/z 241.9 [M]+, 243.9 [M+2]+.

2-(4-Methyl-5-(trimethylstannyl)pyridin-2-yl)propan-2-ol

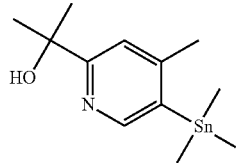

A. 2-(5-Bromo-4-methylpyridin-2-yl)propan-2-ol. 2,5-Dibromo-4-methylpyridine (4.0 g, 15.94 mmol) was dissolved in toluene (60.0 mL) and the reaction was cooled to −78° C. Butyllithium (7.01 mL, 17.54 mmol) was added dropwise and the reaction was allowed to stir for 30 min. Acetone (4.69 mL, 63.8 mmol) was then added and the reaction was allowed to warm to rt and stir for 16 h. The reaction was quenched with saturated ammonium chloride, extracted into ethyl acetate (3×200 mL) and washed with water followed by brine. The organics were dried over magnesium sulfate and volatiles removed under reduced pressure. The compound was purified on silica gel chromatography (0-50% ethyl acetate in hexanes) to afford 2-(5-bromo-4-methylpyridin-2-yl)propan-2-ol (2.33 g, 10.13 mmol, 63.5% yield). MS (ESI) m/z 230.3 [M]$^+$, 232.3 [M+2]$^+$.

B. 2-(4-Methyl-5-(trimethylstannyl)pyridin-2-yl)propan-2-ol. 2-(5-Bromo-4-methylpyridin-2-yl)propan-2-ol (2.33 g, 10.13 mmol) and tetrakis(triphenylphosphine)palladium(0) (1.045 g, 1.013 mmol) were added to a pressure tube and suspended in 1,4-dioxane (33.8 mL). 1,1,1,2,2,2-Hexamethyldistannane (2.99 mL, 12.15 mmol) was then added and heated to 150° C. for 30 min. The reaction was allowed to cool to rt and was filtered through celite and washed with ethyl acetate. Organic volatiles were removed under reduced pressure followed by an extraction in ethyl acetate (3×200 mL) and water. Organic volatiles were removed under reduced pressure and the compound purified using silica gel column chromatography on an Biotage column (10-50% ethyl acetate in hexanes) to afford 2-(4-methyl-5-(trimethylstannyl)pyridin-2-yl)propan-2-ol (1.75 g, 5.57 mmol, 55.0% yield). $^1$H NMR (400 MHz, DMSO-d$_6$) δ (ppm) 8.31 (s, 1H), 7.51 (s, 1H), 5.25 (br. s., 1H), 2.37 (s, 3H), 1.41 (s, 6H), 0.65 (br. s., 3H), 0.34 (s, 6H).

Tert-butyl 3-(5-bromo-6-methylpyridin-2-yl)-1H-1,2,4-triazole-1-carboxylate

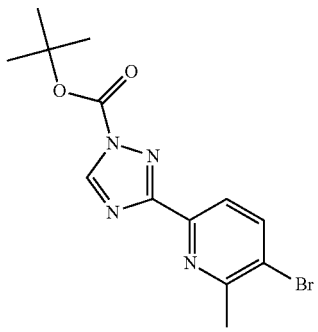 [SMILES: Cc1nc(-c2ncn(C(=O)OC(C)(C)C)n2)ccc1Br]

A. 5-Bromo-6-methylpicolinonitrile. A 1-L, three-neck, round-bottom flask equipped with a mechanical stirrer and a nitrogen inlet was charged with 3,6-dibromo-2-methylpyridine (150 g, 0.59 mol), copper (I) cyanide (42.8 g, 0.47 mol) and sodium cyanide (23 g, 0.47 mol). To the mixture was added N,N-dimethylformamide (300 mL). The mixture was heated to 95° C. and stirred for 48 h. The reaction mixture was cooled to ambient temperature and poured into ethanol (3 L) while stirring. The mixture was filtered through a pad of Celite, the filtrate was concentrated under reduced pressure and partitioned between water (3 L) and ethyl acetate (3 L). The organic layer was separated and washed with brine (2×600 mL), dried over anhydrous sodium sulfate, filtered and concentrated. The crude product was purified by silica gel plug purification (0-5% ethyl acetate in hexanes) to afford the product (61.5 g, 45% yield) as a white solid. In addition, 19.32 g (14%) of the mixture of the starting material and the product was isolated. Alternate approach: 3,6-Dibromo-2-methylpyridine (1 equiv) and sodium iodide (2 equiv), were combined in propionitrile (15× vol). The mixture was stirred and iodotrimethylsilane (0.2 eqive) was added. The reaction mixture was heated and stirred at 95° C. for 24 h, cooled to room temperature and diluted with ethyl acetate and water. The organic phase was washed with aqueous sodium bicarbonate, aqueous sodium thiosulfate, and aqueous sodium chloride. The organic layer was dried over sodium sulfate, filtered, and concentrated under reduced pressure with addition of ethyl acetate to a residue. The product was solidified under vacuum to give 3-bromo-6-iodo-2-methylpyridine as an off-white solid. 3-Bromo-6-iodo-2-methylpyridine (1 equiv) in acetonitrile (7× vol) was treated with copper cyanide (0.5 equiv), sodium cyanide (0.8 equiv), and additional acetonitrile (3× vol). The reaction slurry was heated at 80° C. for 24 h. The reaction mixture was cooled to room temperature, treated with aqueous ammonium hydroxide (1.2 equiv), and filtered through Celite. The filtrate was diluted with ethyl acetate and the phases were separated. The organic layer was washed with aqueous ammonium hydroxide and aqueous sodium chloride, dried over sodium sulfate and filtered. The filtrate was concentrated under reduced pressure to give the title compound as an off-white solid.

B. 5-Bromo-6-methylpicolinohydrazonamide. A 500-mL, three-neck, round-bottom flask was equipped with 5-bromo-6-methylpicolinonitrile (101.5 g, 0.515 mol), ethanol (122 mL) and hydrazine hydrate (50 mL, 1.03 mol). The resulting very thick mixture was allowed to stir at ambient temperature for 24 h. More ethanol (50 mL) was added and the mixture was allowed to stir over the weekend. The mixture was filtered and washed with cold ethanol (100 mL) and cold hexanes (50 mL). The solids were dried in a vacuum oven to afford the product (110 g, 93% yield) as an off-white solid.

C. 3-Bromo-2-methyl-6-(1H-1,2,4-triazol-3-yl)pyridine A 500-mL, three-neck, round-bottom flask was equipped with a mechanical stirrer, a thermocouple connected to a J-KEM temperature controller and a reflux condenser. The flask was charged with 5-bromo-6-methylpicolinohydrazonamide (100 g, 0.463 mol) and formic acid (250 mL). The resulting solution was heated to 100° C. and stirred for 48 h. Formic acid was removed under reduced pressure and the resulting slurry was treated with water (1.5 L) while vigorously stirring. The mixture was filtered and washed with water (300 mL). The solids were transferred into a round-bottom flask and treated with water (1 L) and 1 M sodium hydroxide solution until pH 7. The mixture was allowed to stir for 30 min, filtered, washed with water (300 mL) and dried in a vacuum oven at 30-35° C. for 48 h to afford the product (96 g, 92% yield) as a white solid.

D. 3-Bromo-2-methyl-6-(1-(tetrahydro-2H-pyran-2-yl)-1H-1,2,4-triazol-3-yl)pyridine. To a suspension of 3-bromo-2-methyl-6-(1H-1,2,4-triazol-3-yl)pyridine (96.0 g, 0.4 mol) in tetrahydrofuran (780 mL) was added 3,4-dihydro-2H-pyran (72.5 mL, 0.8 mol) and methanesulfonic acid (3.2 mL). The mixture was heated to 65° C. and the resulting yellow solution was allowed to stir at 65° C. for 6 h. The mixture was cooled to ambient temperature, quenched with triethylamine (23 mL), concentrated under reduced pressure and further dried in a high vacuum for 1 h. The resulting oil was dissolved in acetonitrile (250 mL) and the solution was added into water (750 mL) while stirring vigorously. More acetonitrile (80 mL) was added and the mixture was allowed to stir for 1 h. The resulting solids were filtered, washed with 1:4 acetonitrile/water (800 mL) and dried in a vacuum oven for 48 h to afford the product (110 g, 85% yield) as a white solid. The product was further purified by silica gel plug purification (1:1 hexanes/ethyl acetate) to give 88 g of the pure product as a white solid and 16.2 g of less pure product. MS (ESI) m/z 239.1 [M]$^+$, 241.1 [M+2]$^+$.

E. tert-Butyl 3-(5-bromo-6-methylpyridin-2-yl)-1H-1,2,4-triazole-1-carboxylate. To a mixture of 3-bromo-2-methyl-6-(1H-1,2,4-triazol-3-yl)pyridine (300 g, 1.25 mol) in dioxane (4 L) was added sodium carbonate (398 g, 3.75 mol), followed by water (4 L). di-tert-Butyl dicarbonate (274 g, 1.25 mol) was added and the mixture was stirred of 1 h at room temperature. The mixture was then diluted with cold water (~10 L) and extracted with ethyl acetate (4 L×3). The combined ethyl acetate layer was washed with brine, dried over sodium sulfate, filtered and concentrated to afford the product (254 g, 60% yield) as a slightly yellow solid.

4-(Tetrahydro-2H-pyran-2-yl)-3-(4-(4,4,5,5-tetramethyl-1,3,2-dioxaborolan-2-yl)phenyl)-4H-1,2,4-triazole

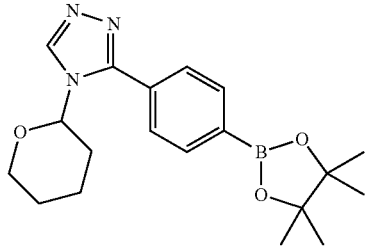 [SMILES: CC1(C)OB(c2ccc(-c3nncn3C3CCCCO3)cc2)OC1(C)C]

A. Ethyl 4-bromobenzimidate hydrochloride. A solution of 4-bromobenzonitrile (17.65 g, 97 mmol) in ethanol (500 mL) was acidified with hydrogen chloride gas at 0° C. for fifteen minutes. The solution was allowed to stir for 16 h. The solution was condensed under reduced pressure to afford the title compound (25.35 g, 99%). MS (ESI) m/z 228.1 [M]$^+$, 230.4 [M+2]$^+$.

B. 3-(4-Bromophenyl)-4H-1,2,4-triazole. Ethyl 4-bromobenzimidate hydrochloride (35.6 g, 135 mmol), formic hydrazide (16.16 g, 269 mmol) and triethylamine (75 mL, 538 mmol) were combined in a screw capped flask and heated to 85° C. for 16 h. The solution was condensed under reduced pressure to afford a solid, which was partitioned between water and ethyl acetate (3×), dried over magnesium sulfate and solvent removed under reduced pressure. The resulting solid was sonicated with 20% ethyl acetate in hexanes, filtered and dried to afford the title compound (14.6 g, 65.2 mmol, 48% yield). MS (ESI) m/z 224.1 [M]$^+$, 226.1 [M+2]$^+$.

C. 3-(4-Bromophenyl)-4-(tetrahydro-2H-pyran-2-yl)-4H-1,2,4-triazole. A solution of 3-(4-Bromophenyl)-4H-1,2,4-triazole (14.1 g, 62.9 mmol), 3,4-dihydro-2H-pyran (10.59 mmol) and methanesulfonic acid (1.19 g, 6.29 mmol) in tetrahydrofuran (150 mL) was heated at 75° C. for 2 h. The solution was condensed and partitioned between sodium bicarbonate solution and ethyl acetate (3×), the organics dried over magnesium sulfate, filtered and solvent removed under reduced pressure. The solid was triturated with 10% ethyl acetate in hexanes to afford the title compound (8.1 g, 26.3 mmol, 70% yield). MS (ESI) m/z 308.4 [M]$^+$, 310.5 [M+2]$^+$.

D. 4-(Tetrahydro-2H-pyran-2-yl)-3-(4-(4,4,5,5-tetramethyl-1,3,2-dioxaborolan-2-yl)phenyl)-4H-1,2,4-triazole. 3-(4-Bromophenyl)-4-(tetrahydro-2H-pyran-2-yl)-4H-1,2,4-triazole (8.1 g, 26.3 mmol), bis(pinacolato)diboron (6.67 g, 26.3 mmol) and potassium acetate (10.32 g, 105 mmol) were combined in dimethylformamide (100 mL). The solution was purged with nitrogen gas for 2 minutes. Dichloro[1,1'-bis(diphenylphosphino)ferrocene]palladium (II) dichloromethane (1.07 g, 1.31 mmol) was then added and the solution heated to 100° C. for 16 h. The solution was filtered through celite and the filtrate condensed under reduced pressure to afford a dark oil. The oil was purified via Biotage chromatography (0-70% ethyl acetate in hexanes) to afford a solid upon drying. The solid was diluted with hexanes, sonicated, filtered and dried to afford the title compound (7.1 g, 20.0 mmol, 71% yield). MS (ESI) m/z 356.5 [M+1]$^+$.

5-Bromo-2-(1-(tetrahydro-2H-pyran-2-yl)-1H-1,2,4-triazol-3-yl)pyridine

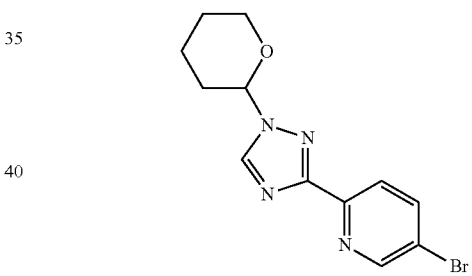

A. (E)-5-bromo-N-((dimethylamino)methylene)picolinamide. A solution of 5-bromopicolinamide (0.500 g, 2.49 mmol) and dimethylformamide dimethylacetal (20 mL), were heated to 85° C. for 3 h. The reaction was concentrated and the product was used directly in the next step (0.604 g, 95% yield). MS (ESI) m/z 257.1 [M+1]$^+$.

B. 5-Bromo-2-(1H-1,2,4-triazol-3-yl)pyridine. A solution of (E) -5-bromo-N-((dimethylamino)methylene)picolinamide (0.604 mg, 2.36 mmol) and hydrazine (2.12 g, 66.1 mmol) was stirred at 25° C. for 3 h. The reaction was concentrated and diluted with water. The resulting precipitate was collected by filtration and dried under vacuum to give the title compound (0.442 g, 83% yield). MS (ESI) m/z 226.1 [M+1]$^+$.

C. 5-Bromo-2-(1-(tetrahydro-2H-pyran-2-yl)-1H-1,2,4-triazol-3-yl)pyridine. A solution of 5-bromo-2-(1H-1,2,4-triazol-3-yl)pyridine (0.342 mg, 1.52 mmol), 3,4-dihydro-2H-pyran (0.256 g, 3.04 mmol) and 4-methylbenzenesulfonic acid (0.058 g, 0.30 mmol) in tetrahydrofuran was heated to 75° C. for 6 h. The reaction was concentrated and purified using Biotage column chromatography (0-20% methanol in dichloromethane) to provide semi-clean product as an oil (0.614 g, 1.9 mmol, >100% yield).

This material was used without further purification. MS (ESI) m/z 309.4 [M]+, 311.1 [M+2]+.

tert-Butyl 6-bromo-4-methyl-2-(methylamino)-1H-benzo[d]imidazole-1-carboxylate

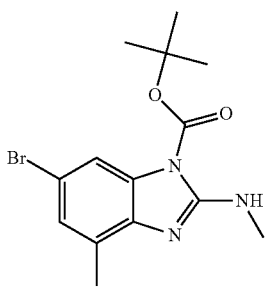 [SMILES: CNc1nc2c(C)cc(Br)cc2n1C(=O)OC(C)(C)C]

A. (6-Bromo-4-methylbenzimidazol-2-yl)-N-methylamine. Isothiocyanatomethane (0.055 g, 0.746 mmol) in N,N-dimethylformamide (1.0 mL) was added dropwise slowly to a stirred solution of 5-bromo-3-methylbenzene-1,2-diamine (0.150 g, 0.746 mmol) in N,N-dimethylformamide (1.5 mL) at 0° C. The cold bath was removed, the reaction mixture was capped and stirred at room temperature for 48 h. N-(3-Dimethylaminopropyl)-N'-ethylcarbodiimide hydrochloride (0.157 g, 0.821 mmol) was added and the reaction mixture capped and heated at 40° C. overnight. The resulting mixture was diluted with methanol, filtered and purified using reverse-phase preparatory HPLC (10-50% acetonitrile+0.1% TFA in H2O+0.1% TFA, over 30 min). Fractions containing the desired product were combined and most of the solvent removed under reduced pressure. Acetonitrile was added and the resulting mixture loaded on a Strata ion exchange column. The column was washed successively with water, acetonitrile, methanol and 5% ammonium hydroxide in methanol. The product eluted with the 5% ammonium hydroxide in methanol and was concentrated under reduced pressure and dried under high vacuum to give the desired product (0.128 g, 0.53 mmol, 72% yield) as a slightly yellow waxy solid. MS (ESI) m/z 240 [M]+, 242 [M+2]+.

B. tert-Butyl 6-bromo-4-methyl-2-(methylamino)-1H-benzo[d]imidazole-1-carboxylate (6-Bromo-4-methylbenzimidazol-2-yl)-N-methylamine (0.128 g, 0.533 mmol), diisopropylethylamine (0.464 mL, 2.67 mmol), di-tert-butyl dicarbonate (0.349 g, 1.599 mmol) and N,N-dimethylformamide (5 mL) were combined in a 100 mL round bottom flask, capped and stirred at room temperature for 21 h. The resulting mixture was partitioned between water and ethyl acetate. The layers were separated and the organics were washed with water and brine. The organics were dried over magnesium sulfate, filtered, concentrated under reduced pressure and purified using flash chromatography (10-30% ethyl acetate in hexanes) to give the desired product (0.092 g, 0.27 mmol, 51% yield) as a yellow waxy solid. MS (ESI) m/z 340 [M]+, 342 [M+2]+.

7-Methyl-5-(4,4,5,5-tetramethyl-1,3,2-dioxaborolan-2-yl)-1H-benzo[d]imidazol-2-amine

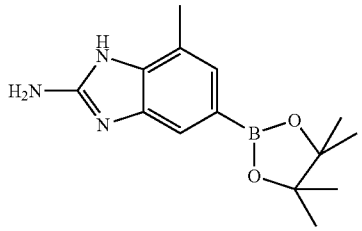 [SMILES: Cc1cc(B2OC(C)(C)C(C)(C)O2)cc2nc(N)[nH]c12]

A. 7-Methyl-5-(4,4,5,5-tetramethyl-1,3,2-dioxaborolan-2-yl)-1H-benzo[d]imidazol-2-amine 3-Methyl-5-(4,4,5,5-tetramethyl-1,3,2-dioxaborolan-2-yl)benzene-1,2-diamine (See Example 1.G) (500 mg, 2.015 mmol) and cyanic bromide (0.484 mL, 2.418 mmol) were added to a round bottom flask at room temperature, suspended in methanol (10.0 mL) and allowed to stir for 1.5 h. Volatiles were removed under reduced pressure followed by the addition of saturated sodium bicarbonate. The precipitate was collected via filtration, washed with ethyl acetate and dried under reduced pressure to afford the title compound (557 mg, 2.039 mmol, quant. yield). Compound was carried forward without further purification or characterization. MS (ESI) m/z 273.8 [M+1]+.

4-Methyl-1-(tetrahydro-2H-pyran-2-yl)-6-(4,4,5,5-tetramethyl-1,3,2-dioxaborolan-2-yl)-1H-benzo[d]imidazole

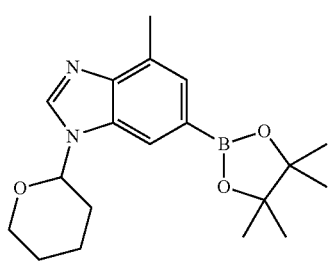 [SMILES: Cc1cc(B2OC(C)(C)C(C)(C)O2)cc2c1ncn2C1CCCCO1]

A. 6-Bromo-4-methyl-1-(tetrahydro-2H-pyran-2-yl)-1H-benzo[d]imidazole. 6-Bromo-4-methyl-1H-benzo[d]imidazole (1.02 g, 4.83 mmol) was dissolved in tetrahydrofuran (10 mL) at room temperature with stirring under nitrogen. 3,4-Dihydro-2H-pyran (3.5 mL, 38.4 mmol) and methanesulfonic acid (0.032 mL, 0.48 mmol) were added and the resulting mixture heated at 75° C. for 49 h. The resulting mixture was cooled to room temperature, diluted with ethyl acetate and washed with saturated aqueous sodium bicarbonate and brine. The organics were dried over magnesium sulfate, filtered and concentrated under reduced pressure. Flash chromatography (50-100% ethyl acetate in hexanes) gave the desired product (1.32 g, 4.47 mmol, 93% yield) as a light yellow solid. MS (ESI) m/z 295.1 [M]+, 297.3 [M+2]+.

B. 4-Methyl-1-(tetrahydro-2H-pyran-2-yl)-6-(4,4,5,5-tetramethyl-1,3,2-dioxaborolan-2-yl)-1H-benzo[d]imidazole. 6-Bromo-4-methyl-1-(tetrahydro-2H-pyran-2-yl)-1H-benzo[d]imidazole (1.320 g, 4.47 mmol), bis(pinacolato)diboron (1.192 g, 4.70 mmol), [1,1'-bis(diphenylphosphino)ferrocene]dichloropalladium(II), complex with dichloromethane (1:1) (183 mg, 0.22 mmol), potassium acetate (1.317 g, 13.4 mmol) and dimethyl sulfoxide (9 mL) were combined in a round bottom flask and stirred. The atmosphere in the flask was removed under vacuum and replaced with nitrogen three times. The resulting mixture was heated at 90° C. under nitrogen for 1.5 h. The resulting mixture was diluted with ethyl acetate and filtered through Celite. The filter cake was washed thoroughly with ethyl acetate. The filtrate was washed twice with water, once with brine, dried over magnesium sulfate, filtered and concentrated on a under reduced pressure. Flash chromatography (50-100% ethyl acetate in hexanes) gave the desired product at ~90% purity (1.31 g, 3.83 mmol, 77% yield) as a yellow tan foam-solid. MS (ESI) m/z 343.2 [M+1]$^+$.

5.2 Biological Examples

5.2.1 Biochemical Assays

TOR HTR-FRET Assay. The following is an example of an assay that can be used to determine the TOR kinase inhibitory activity of a test compound. TOR kinase inhibitors were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen recombinant TOR enzyme (cat# PV4753) was diluted in this buffer to an assay concentration of 0.200 μg/mL.

ATP/Substrate solution: 0.075 mM ATP, 12.5 mM MnCl$_2$, 50 mM Hepes, pH 7.4, 50 mM β-GOP, 250 nM Microcystin LR, 0.25 mM EDTA, 5 mM DTT, and 3.5 μg/mL GST-p70S6.

Detection reagent solution: 50 mM HEPES, pH 7.4, 0.01% Triton X-100, 0.01% BSA, 0.1 mM EDTA, 12.7 μg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 μL of the Simple TOR buffer is added 0.5 μL of test compound in DMSO. To initiate the reaction 5 μL of ATP/Substrate solution was added to 20 μL of the Simple TOR buffer solution (control) and to the compound solution prepared above. The assay was stopped after 60 min by adding 5 μL of a 60 mM EDTA solution; 10 μL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

5.3 Heteroaryl Compound Activity

Heteroaryl Compounds as described herein were tested in the TOR HTR-FRET assay and were found to have activity therein, with all of the compounds having an IC$_{50}$ below 10 μM in the assay, with some compounds having an IC$_{50}$ between and 0.005 nM and 250 nM, others having an IC$_{50}$ between 250 nM and 500 nM, others having an IC$_{50}$ between 500 nM and 1 μM, and others having an IC$_{50}$ between 1 μM and 10 μM. IC$_{50}$ values for compounds of Formula (I) and (II) can be found in U.S. patent application Ser. No. 12/605,791, filed on Oct. 26, 2009 (see Table 1 at pages 141-187), which is incorporated by reference herein in its entirety The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A compound having formula (VIII):

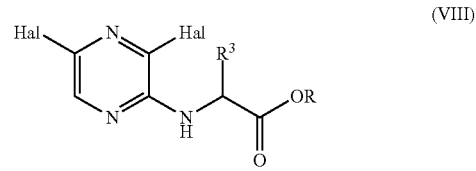

(VIII)

or a salt, tautomer or stereoisomer thereof, wherein:
each Hal is bromine;
R is the alkali metal salt of the carboxylate; and
R$^3$ is H, or a substituted or unsubstituted C$_{1-8}$ alkyl.

2. A method of preparing a compound having formula (VII):

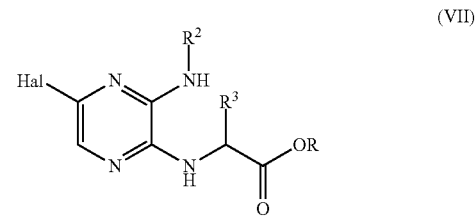

(VII)

wherein:
R$^2$ is H, substituted or unsubstituted C$_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;
R$^3$ is H, or a substituted or unsubstituted C$_{1-8}$ alkyl;
Hal is a halogen; and
R is the alkali metal salt of the carboxylate,
the method comprising contacting an alkyl ester of a compound of formula (VII) with a metallic base in a solvent under conditions suitable to provide a compound of formula (VII).

3. The method of claim 2, wherein the metallic base is sodium hydroxide.

4. The method of claim 2, wherein Hal is Br.

5. A method of preparing a compound having formula (VI):

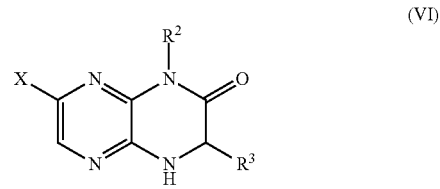

(VI)

the method comprising cyclizing a compound of formula (VII)

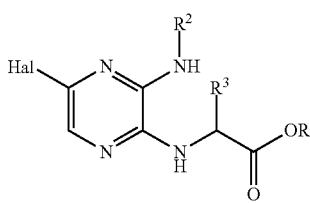

(VII)

in the presence of a base or an acid, wherein said cyclization occurs under conditions suitable to provide a compound of formula (VI), wherein:
X is halogen, $B(OR^+)_2$ or $Sn(R^{++})_3$;
Y is halogen, triflate, $B(OR^+)_2$ or $Sn(R^{++})_3$;
a) when X is halogen, then Y is $B(OR^+)_2$ or $Sn(R^{++})_3$;
b) when Y is halogen or triflate, then X is $B(OR^+)_2$ or $Sn(R^{++})_3$;
$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;
$R^3$ is H, or a substituted or unsubstituted $C_{1-8}$ alkyl;
Hal is a halogen;
and R is the alkali metal salt of the carboxylate.

6. The method of claim 5, wherein R is the sodium salt of the carboxylate.

7. The method of claim 5, wherein Hal is Br.

8. The method of claim 5, wherein the cyclization is performed in a solvent.

9. The method of claim 8, wherein the solvent is methanol or water.

10. The method of claim 5, further comprising preparing a compound having formula (II):

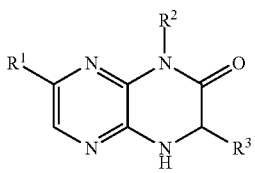

(II)

the method comprising contacting a compound of formula (VI)

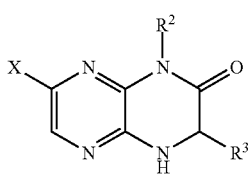

(VI)

with $R^1$—Y in a solvent, in the presence of a palladium catalyst, wherein said contacting occurs under conditions suitable to provide a compound of formula (I), wherein X is halogen, $B(OR^+)_2$ or $Sn(R^{++})_3$;
Y is halogen, triflate, $B(OR^+)_2$ or $Sn(R^{++})_3$;
a) when X is halogen, then Y is $B(OR^+)_2$ or $Sn(R^{++})_3$; or
b) when Y is halogen or triflate, then X is $B(OR^+)_2$ or $Sn(R^{++})_3$;
wherein each $R^+$ is independently hydrogen or substituted or unsubstituted $C_{1-3}$ alkyl, or each $R^+$, together with the boron atom and the atoms to which they are attached, form a cyclic boronate; and each $R^{++}$ is a $C_{1-3}$ alkyl; and
wherein:
$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;
$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;
$R^3$ is H, or a substituted or unsubstituted $C_{1-8}$ alkyl.

11. The method of claim 10, wherein when X or Y is a halogen, the halogen is Br.

12. The method of claim 10, wherein the solvent is dimethylformamide, isopropanol, dioxane, toluene, dimethylacetamide, tetrahydrofuran, or a combination thereof, with or without the presence of water.

13. The method of claim 10, wherein the palladium catalyst is dichloro[1,1'-bis(diphenylphosphino)ferrocene]palladium (II)dichloro-methane), palladium(dba)$_2$/tri-o-tolylphosphine, dichloro[1,1'-bis(ditert-butylphosphino)ferrocene] palladium, tetrakis(triphenylphosphine)palladium(0), dichlorobis(p-dimethylamino phenylditbutylphosphine)palladium(II) or palladium (II) acetate/4,5-bis(diphenylphosphino)-9,9-dimethylxanthene.

14. The method of claim 10, wherein the palladium catalyst is dichloro[1,1'-bis(diphenylphosphino)ferrocene]palladium (II)dichloro-methane), palladium(dba)$_2$/tri-o-tolylphosphine, tetrakis(triphenylphosphine)palladium(0) or palladium (II) acetate/4,5-bis(diphenylphosphino)-9,9-dimethylxanthene.

15. The method of claim 10, wherein when X or Y is $B(OR^+)_2$, the contacting occurs in the presence of a base.

16. The method of claim 15, wherein the base is sodium carbonate.

17. The method of claim 15, wherein $B(OR^+)_2$ is $B(OH)_2$ or $B(—OC(CH_3)_2C(CH_3)_2O—)$.

18. The method of claim 10, wherein when X or Y is $Sn(R^{++})_3$, the contacting optionally occurs in the presence of a base.

19. The method of claim 18, wherein the base is triethylamine.

20. The method of claim 18, wherein $R^{++}$ is methyl or n-butyl.

21. The method of claim 10, wherein the base is potassium butoxide.

22. The method of claim 10, wherein the acid is acetic acid, TFA, HCl, or phosphoric acid.

23. The method of claim 2, further comprising preparing a compound of formula (VII),

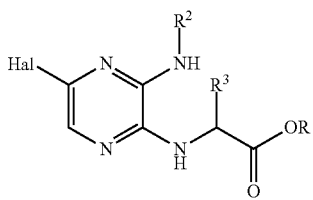

(VII)

the method comprising contacting a compound of formula (VIII)

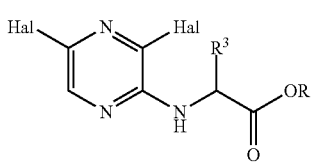

(VIII)

with R²—NH₂ in a solvent, optionally in the presence of a base, wherein said contacting occurs under conditions suitable to provide a compound of formula (VII), wherein Hal is a halogen.

24. The method of claim 23, wherein the solvent is dimethylsulfoxide or N-methylpyrrolidinone.

25. The method of claim 23, wherein the base is triethylamine or Diisopropylethylamine.

26. The method of claim 23, wherein the halogen is Br.

27. The method of claim 10, wherein the compound is
7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;
  7-(6-(1H-1,2,4-triazol-3-yl)pyridin-3-yl)-1-(cis-4-methoxycyclohexyl)-3,4-dihydropyrazino[2,3-b]pyrazin-2(1H)-one;
  7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;
  7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;
  1-ethyl-7-(1H-pyrrolo[3,2-b]pyridin-5-yl)-3,4-dihydropyrazino[2,3-b]pyrazin-2(1H)-one;
  7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;
  7-(1H-benzo[d]imidazol-4-yl)-1-(2-(tetrahydro-2H-pyran-4-yl)ethyl)-3,4-dihydropyrazino[2,3-b]pyrazin-2(1H)-one;
  7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;
  7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;
  7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;
  7-(6-(1H-1,2,4-triazol-3-yl)pyridin-3-yl)-1-(cis-4-hydroxycyclohexyl)-3,4-dihydropyrazino[2,3-b]pyrazin-2(1H)-one;
  7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;
  7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;
  7-(6-(1H-1,2,4-triazol-3-yl)pyridin-3-yl)-1-(2-methoxyethyl)-3,4-dihydropyrazino[2,3-b]pyrazin-2(1H)-one;
  7-(6-(1H-1,2,4-triazol-3-yl)pyridin-3-yl)-1-ethyl-3,4-dihydropyrazino[2,3-b]pyrazin-2(1H)-one;
  7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;
  7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;
  7-(1H-indol-4-yl)-1-(2-(tetrahydro-2H-pyran-4-yl)ethyl)-3,4-dihydropyrazino[2,3-b]pyrazin-2(1H)-one;
  7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;
  7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;
  7-(6-(1H-1,2,4-triazol-3-yl)pyridin-3-yl)-1-(trans-4-hydroxycyclohexyl)-3,4-dihydropyrazino[2,3-b]pyrazin-2(1H)-one;
  7-(6-(1H-1,2,4-triazol-3-yl)pyridin-3-yl)-1-(trans-4-methoxycyclohexyl)-3,4-dihydropyrazino[2,3-b]pyrazin-2(1H)-one;
  7-(6-(1H-1,2,4-triazol-3-yl)pyridin-3-yl)-1-isopropyl-3,4-dihydropyrazino[2,3-b]pyrazin-2(1H)-one;
  7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;
  7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;
  7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;
  7-(5-fluoro-2-methyl-4-(1H-1,2,4-triazol-3-yl)phenyl)-1-isopropyl-3,4-dihydropyrazino[2,3-b]pyrazin-2(1H)-one;
  1-ethyl-7-(5-fluoro-2-methyl-4-(1H-1,2,4-triazol-3-yl)phenyl)-3,4-dihydropyrazino[2,3-b]pyrazin-2(1H)-one;
  7-(2-hydroxypyridin-4-yl)-1-(2-(tetrahydro-2H-pyran-4-yl)ethyl)-3,4-dihydropyrazino[2,3-b]pyrazin-2(1H)-one;
  1-isopropyl-7-(4-methyl-6-(1H-1,2,4-triazol-3-yl)pyridin-3-yl)-3,4-dihydropyrazino[2,3-b]pyrazin-2(1H)-one;
  5-(8-isopropyl-7-oxo-5,6,7,8-tetrahydropyrazino[2,3-b]pyrazin-2-yl)-4-methylpicolinamide;
  7-(1H-indazol-4-yl)-1-(2-(tetrahydro-2H-pyran-4-yl)ethyl)-3,4-dihydropyrazino[2,3-b]pyrazin-2(1H)-one;
  7-(2-aminopyrimidin-5-yl)-1-(2-(tetrahydro-2H-pyran-4-yl)ethyl)-3,4-dihydropyrazino[2,3-b]pyrazin-2(1H)-one;
  7-(2-aminopyridin-4-yl)-1-(2-(tetrahydro-2H-pyran-4-yl)ethyl)-3,4-dihydropyrazino[2,3-b]pyrazin-2(1H)-one;
  7-(6-(methylamino)pyridin-3-yl)-1-(2-(tetrahydro-2H-pyran-4-yl)ethyl)-3,4-dihydropyrazino[2,3-b]pyrazin-2(1H)-one;
  7-(6-hydroxypyridin-3-yl)-1-(2-(tetrahydro-2H-pyran-4-yl)ethyl)-3,4-dihydropyrazino[2,3-b]pyrazin-2(1H)-one;
  7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3, 4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3, 4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3, 4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-(((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7- oxo-8-(2-(tetrahydro-2H-pyran-4-yl)ethyl)-5,6,7,8-tetrahydropyrazino[2,3-b]pyrazin-2-yl)benzamide;

5-(8-(((trans-4-methoxycyclohexyl)methyl)-7-oxo-5,6,7, 8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1(2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3S)-3-methoxycyclopentyl)-3,4-dihydropyrazino[2,3-b]pyrazin-2(1H)-one;

7-(6-(2-hydroxypropan-2-yl)pyridin-3-yl)-1-((1R,3S)-3-methoxycyclopentyl)-3,4-dihydropyrazino[2,3-b]pyrazin-2(1H)-one;

7-(1H-indazol-6-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(2-morpholinoethyl)-3,4-dihydropyrazino[2,3-b]pyrazin-2(1H)-one;

1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(2-morpholinoethyl)-3,4-dihydropyrazino[2,3-b]pyrazin-2(1H)-one;

1-isopropyl-7-(2-methyl-6-(4H-1,2,4-triazol-3-yl)pyridin-3-yl)-3,4-dihydropyrazino[2,3-b]pyrazin-2(1H)-one;

7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;

1((cis-4-methoxycyclohexyl)methyl)-7-(2-methyl-6-(1H-1,2,4-triazol-3-yl)pyridin-3-yl)-3,4-dihydropyrazino[2, 3-b]pyrazin-2(1H)-one;

1-(trans-4-hydroxycyclohexyl)-7-(6-(2-hydroxypropan-2-yl)pyridin-3-yl)-3,4-dihydropyrazino[2,3-b]pyrazin-2(1H)-one;

1-(cis-4-hydroxycyclohexyl)-7-(6-(2-hydroxypropan-2-yl)pyridin-3-yl)-3,4-dihydropyrazino[2,3-b]pyrazin-2(1H)-one;

4-(7-oxo-8-(2-(tetrahydro-2H-pyran-4-yl)ethyl)-5,6,7,8-tetrahydropyrazino[2,3-b]pyrazin-2-yl)benzamide;

7-(1H-indazol-5-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;

1-((1S,3R)-3-methoxycyclopentyl)-7-(2-methyl-6-(4H-1, 2,4-triazol-3-yl)pyridin-3-yl)-3,4-dihydropyrazino[2,3-b]pyrazin-2(1H)-one;

1-((1R,3R)-3-methoxycyclopentyl)-7-(2-methyl-6-(4H-1, 2,4-triazol-3-yl)pyridin-3-yl)-3,4-dihydropyrazino[2,3-b]pyrazin-2(1H)-one;

1-((1R,3S)-3-methoxycyclopentyl)-7-(2-methyl-6-(4H-1, 2,4-triazol-3-yl)pyridin-3-yl)-3,4-dihydropyrazino[2,3-b]pyrazin-2(1H)-one;

1-((1S,3S)-3-methoxycyclopentyl)-7-(2-methyl-6-(4H-1, 2,4-triazol-3-yl)pyridin-3-yl)-3,4-dihydropyrazino[2,3-b]pyrazin-2(1H)-one;

7-(1H-indol-5-yl)-1-(2-(tetrahydro-2H-pyran-4-yl)ethyl)-3,4-dihydropyrazino[2,3-b]pyrazin-2(1H)-one;

1-ethyl-7-(2-methyl-6-(4H-1,2,4-triazol-3-yl)pyridin-3-yl)-3,4-dihydropyrazino[2,3-b]pyrazin-2(1H)-one;

7-(1H-indol-6-yl)-1-(2-(tetrahydro-2H-pyran-4-yl)ethyl)-3,4-dihydropyrazino[2,3-b]pyrazin-2(1H)-one;

7-(4-(2-hydroxypropan-2-yl)phenyl)-1-(trans-4-methoxycyclohexyl)-3,4-dihydropyrazino[2,3-b]pyrazin-2(1H)-one;

7-(6-(2-hydroxypropan-2-yl)pyridin-3-yl)-1-(tetrahydro-2H-pyran-4-yl)-3,4-dihydropyrazino[2,3-b]pyrazin-2(1H)-one;

1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((cis-4-methoxycyclohexyl)methyl)-3,4-dihydropyrazino[2,3-b]pyrazin-2(1H)-one;

1-(2-methoxyethyl)-7-(4-methyl-2-(methylamino)-1H-benzo[d]imidazol-6-yl)-3,4-dihydropyrazino[2,3-b]pyrazin-2(1H)-one;

7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;

7-(2-methyl-4-(4H-1,2,4-triazol-3-yl)phenyl)-3,4-dihydropyrazino[2,3-b]pyrazin-2(1H)-one;

1-(2-methoxyethyl)-7-(4-methyl-6-(1H-1,2,4-triazol-3-yl)pyridin-3-yl)-3,4-dihydropyrazino[2,3-b]pyrazin-2(1H)-one;

1-benzyl-7-(2-methyl-4-(4H-1,2,4-triazol-3-yl)phenyl)-3,4-dihydropyrazino[2,3-b]pyrazin-2(1H)-one;

7-(3-fluoro-4-(4H-1,2,4-triazol-3-yl)phenyl)-1-(2-methoxyethyl)-3,4-dihydropyrazino[2,3-b]pyrazin-2(1H)-one;

7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;

1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(trans-4-methoxycyclohexyl)-3,4-dihydropyrazino[2,3-b]pyrazin-2(1H)-one;

7(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

1-(2-methoxyethyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((trans-4-methoxycyclohexyl)methyl)-3,4-dihydropyrazino[2,3-b]pyrazin-2(1H)-one;

1-(cyclopentylmethyl)-7-(6-(2-hydroxypropan-2-yl)pyridin-3-yl)-3,4-dihydropyrazino[2,3-b]pyrazin-2(1H)-one;

7-(4-(2-hydroxypropan-2-yl)phenyl)-1-(2-methoxyethyl)-3,4-dihydropyrazino[2,3-b]pyrazin-2(1H)-one;

(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;

7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(4-(trifluoromethyl)benzyl)-3,4-dihydropyrazino[2,3-b]pyrazin-2(1H)-one;

7-(6-(2-hydroxypropan-2-yl)pyridin-3-yl)-1-(3-(trifluoromethyl)benzyl)-3,4-dihydropyrazino[2,3-b]pyrazin-2(1H)-one;

7-(6-(2-hydroxypropan-2-yl)pyridin-3-yl)-1-(3-methoxypropyl)-3,4-dihydropyrazino[2,3-b]pyrazin-2(1H)-one;

7-(4-methyl-6-(4H-1,2,4-triazol-3-yl)pyridin-3-yl)-1-(2-(tetrahydro-2H-pyran-4-yl)methyl)-3,4-dihydropyrazino[2,3-b]pyrazin-2(1H)-one;

7-(6-(2-hydroxypropan-2-yl)pyridin-3-yl)-1-(2-methoxyethyl)-3,4-dihydropyrazino[2,3-b]pyrazin-2(1H)-one;

7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;

7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;

7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;

7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-3,3-dimethyl-1-(2-(tetrahydro-2H-pyran-4-yl)ethyl)-3,4-dihydropyrazino[2,3-b]pyrazin-2(1H)-one;

7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;

7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;

1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; or 1-(2-hydroxyethyl)-7-(2-methyl-6-(1H-1,2,4-triazol-3-yl)pyridin-3-yl)-3,4-dihydropyrazino[2,3-b]pyrazin-2(1H) one.

\* \* \* \* \*